United States Patent [19]

Bernotas et al.

[11] Patent Number: 5,436,246
[45] Date of Patent: Jul. 25, 1995

[54] SEROTONIN RECEPTOR AGENTS

[75] Inventors: Ronald C. Bernotas, Cincinnati, Ohio; Jeffrey S. Sprouse, Stonington, Conn.; Hsien C. Cheng, Cincinnati, Ohio

[73] Assignee: Merrell Dow Pharmaceuticals Inc.

[21] Appl. No.: 119,791

[22] Filed: Sep. 15, 1993

Related U.S. Application Data

[63] Continuation-in-part of Ser. No. 79,692, Jun. 16, 1993, abandoned, which is a continuation of Ser. No. 947,007, Sep. 17, 1992, abandoned.

[51] Int. Cl.⁶ .......................................... A61K 31/495
[52] U.S. Cl. ...................................... 514/255
[58] Field of Search ............................... 514/255

[56] References Cited

U.S. PATENT DOCUMENTS

| | | |
|---|---|---|
| 4,833,142 | 5/1989 | Hartog et al. . |
| 5,032,598 | 7/1991 | Baldwin et al. . |
| 5,051,421 | 9/1991 | Ferrini . |
| 5,143,916 | 9/1992 | Lavielle et al. ............... 514/255 |
| 5,246,935 | 9/1993 | Jeppesen et al. ............... 514/255 |

FOREIGN PATENT DOCUMENTS

| | | |
|---|---|---|
| 0158380 | 10/1985 | European Pat. Off. . |
| 0185429 | 12/1985 | European Pat. Off. . |
| 0189612 | 12/1985 | European Pat. Off. . |
| 0372637 | 12/1989 | European Pat. Off. . |

*Primary Examiner*—Johann Richter
*Assistant Examiner*—John Peabody
*Attorney, Agent, or Firm*—Michael J. Sayles

[57] ABSTRACT

The present invention is directed to a new class of 2-optionally substituted-4-piperazine-benzothiophene derivatives of the formula

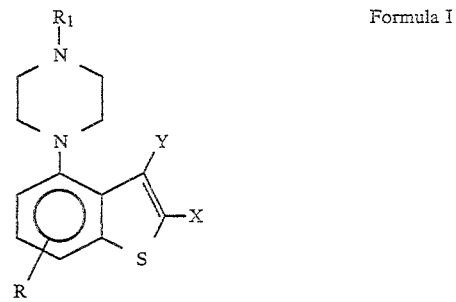

Formula I in which Y is represented by hydrogen or $C_{1-3}$ alkyl; R is represented by a substituent selected from the group consisting of hydrogen, $C_{1-4}$ alkyl, $C_{1-4}$ alkoxy, halogen, $-CF_3$, $-OCF_3$, and $-OH$; $R_1$ is represented by hydrogen, cycloalkyl, $C_{1-6}$ alkyl, phenyl optionally substituted, phenylalkyl, or phenylamidoalkyl; X is represented by hydrogen, $-(CH_2)_n X_1$, $CH=CHX_1$ or $CHX_2-(CH_2)_q -CH_3$; n is an integer from 0-2; q is either the integer 0 or 1; $X_1$ is represented by $-OH-$,$-OR_2$, $-NR_2R_3$, $-CO_2R_2$, $-CONR_2R_3$, $-CN$, or $-COR_2$; $R_2$ and $R_3$ are each independently represented by hydrogen, $C_{1-4}$ alkyl, phenyl optionally substituted, phenylalkyl, or $R_2$ and $R_3$ together form a $(CH_2)_m$ cycloalkyl, where m=2-6; $X_2$ is $-OR_4$ or $-NR_4R_5$ in which $R_4$ and $R_5$ are each independently hydrogen or $C_{1-4}$ alkyl; and the pharmaceutically acceptable addition salts thereof; with the proviso that when n is O or X is $-CH=CHX_1$, then $X_1$ is not OH, $OR_2$, or $NR_2R_3$; that are serotonin $5HT_{1A}$ and $5HT_{1D}$ receptor agents.

2 Claims, 1 Drawing Sheet

SEROTONIN RECEPTOR AGENTS

This is a Continuation-in-part of U.S. Ser. No. 08/079,692 filed Jun. 16, 1993 now abandoned; which was a continuation of U.S. Ser. No 07/947,007, filed Sep. 17, 1992, now abandoned.

The present invention is directed to a new class of serotonin $5HT_{1A}$ and $5HT_{1D}$ receptor agents, both agonists and antagonists, their use in the treatment of anxiety, depression, migraine, stroke, angina and hypertension as well as pharmaceutical and diagnostic compositions containing them.

In accordance with the present invention a new class of serotonin $5HT_{1A}$ and $5HT_{1D}$ receptor agents have been discovered which can be described by the following formula:

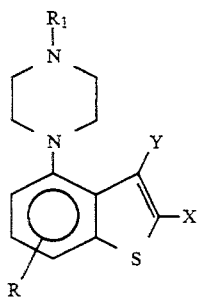

Formula I in which Y is represented by hydrogen or $C_{1-3}$ alkyl; R is represented by a substituent selected from the group consisting of hydrogen, $C_{1-4}$ alkyl, $C_{1-4}$ alkoxy, halogen, $-CF_3$, $-OCF_3$, and $-OH$; $R_1$ is represented by hydrogen, cycloalkyl, $C_{1-6}$ alkyl, phenyl optionally substituted, phenylalkyl, or phenylamidoalkyl; X is represented by hydrogen, $-(CH_2)_nX_1$, $-CH=CHX_1$ or $-CHX_2-(CH_2)_q-CH_3$; n is an integer from 0-2; q is either the integer 0 or 1; $X_1$ is represented by $-OH$, $-OR_2$, $-NR_2R_3$, $-CO_2R_2$, $-CONR_2R_3$, $-CN$, $CH_2OH$ or $-COR_2$; $R_2$ and $R_3$ are each independently represented by hydrogen, $C_{1-4}$ alkyl, phenyl optionally substituted, phenylalkyl, or $R_2$ and $R_3$ together form a $(CH_2)_m$ cycloalkyl, where $m=2-6$; $X_2$ is $-OR_4$ or $-NR_4R_5$ in which $R_4$ and $R_5$ are each independently hydrogen or $C_{1-4}$ alkyl; and the pharmaceutically acceptable addition salts thereof; with the proviso that when n is O or X is $-CH=CHX_1$, then $X_1$ is not OH, $OR_2$, or $NR_2R_3$.

These benzothiophene derivatives mimic or block the effects of serotonin at the $5HT_{1A}$ and $_{1D}$ receptors. They are useful in the treatment of anxiety, depression, migraine, stroke, angina and hypertension.

As used in this application:
a) the term "halogen" refers to a fluorine, chlorine, or bromine atom.
b) the terms "lower alkyl group and $C_{1-4}$ alkyl" refer to a branched or straight chained alkyl group containing from 1-4 carbon atoms, such as methyl, ethyl, n-propyl, isopropyl, n-butyl, isobutyl, etc.
c) the terms "lower alkoxy group and $C_{1-4}$ alkoxy" refer to a straight or branched alkoxy group containing from 1-4 carbon atoms, such as methoxy, ethoxy, n-propoxy, isopropoxy, n-butoxy, isobutoxy, etc.
d) the term "phenyl optionally substituted" refers to a phenyl moiety ($C_6H_5$) which may be substituted with up to 3 substituents, each substituent is independently selected from the group consisting of halogens, $C_{1-4}$ alkyl, $C_{1-4}$ alkoxy, $CF_3$, $OCF_3$, OH, CN, $NH_2$ and $NO_2$. These substituents may be the same or different and may be located at any of the ortho, meta, or para positions.
e) the term "phenylalkyl substituent" refers to the following structure, $-(CH_2)_b-C_6H_5$, in which b is an integer from 1-4. This phenyl ring may be substituted in the manner described immediately above.
f) the term "pharmaceutically acceptable salt" refers to either a basic addition salt or an acid addition salt.
g) the term "$C_{1-3}$ alkyl" refers to a branched or straight chained alkyl group containing from 1-3 carbon atoms, such as methyl, ethyl, n-propyl, or isopropyl.
h) the term "cycloalkyl" refers to cycloalkyl substituent containing from 3-7 carbon atoms such as cyclopropyl, cyclobutyl, cyclopentyl, cyclohexyl or cycloheptyl.
i) the term "$C_{1-6}$ alkyl" refers to a branched or straight chained alkyl group containing from 1-6 carbon atoms, such as methyl, ethyl, n-propyl, isopropyl, n-butyl, isobutyl, n-pentyl, n-hexyl, etc.
j) the term "phenylamidoalkyl" refers to the following structure, $-(CH_2)_i-CONH-C_6H_5$, in which i is an integer from 1-6. This phenyl ring may be substituted in the manner described immediately above.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methanesulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Figure 1:
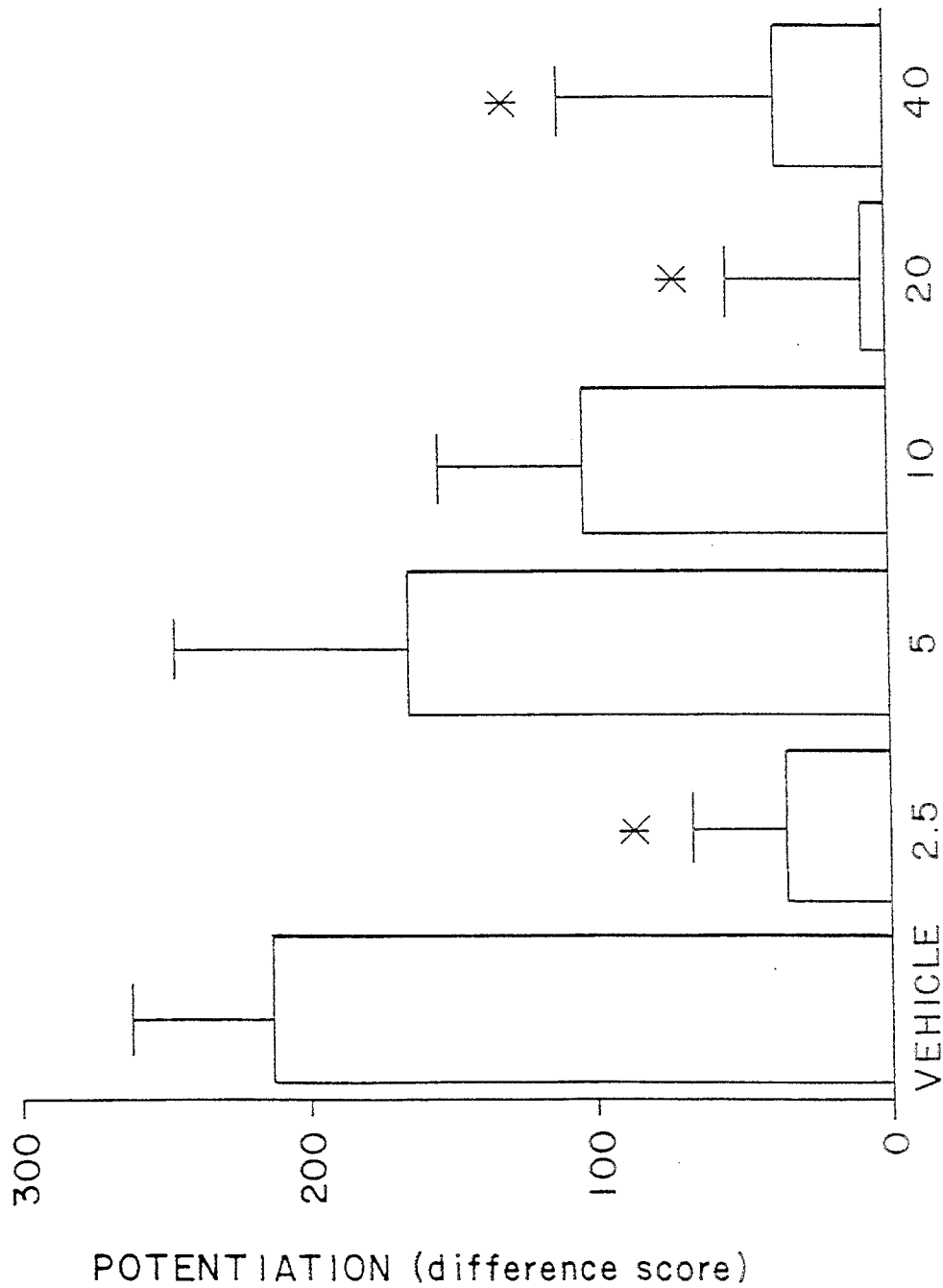
FIG. 1 Graphs the effect of compound on fear-potential startle. Graph shows mean potentiation (difference between Light-Noise and Noise-Alone mean startle amplitudes) after treatment with vehicle or various doses of compound.

S.C. * Significantly differ (p<.05) form vehicle group by Fisher PLSD.

Some of the compounds of Formula I contain an asymmetric center and will therefore exist as enantiomers Any reference in this application to one of the compounds represented by Formula I, or any intermediate thereof, should be construed as covering a specific optical isomer or a racemic mixture. The specific optical isomers can be separated and recovered by techniques known in the art such as chromatography on chiral stationary phases, resolution via chiral salt formation and subsequent separation by selective crystallization, or enzymatic hydrolysis using stereoselective esterases as is known in the art. Alternatively, a chirally pure starting material may be utilized.

All of the compounds of Formula I contain a benzothiophene ring which may be optionally substituted as indicated by the R and Y substituents. In order to further illustrate the present invention, the numbering system is present below for this ring system:

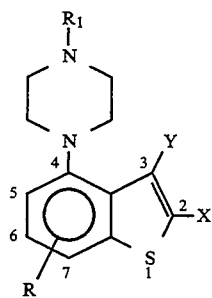

Formula I

R may be represented by up to 2 substituents. These substituents may be the same or different and may be located at positions 5, 6 or 7 of the benzothiophene ring.

Examples of compounds encompassed by Formula I include:

a) 4-[4-(2-phenylethyl)-1-piperazinyl]-benzo[b]thiophene-2-methanol monohydrochloride;
b) 4-[4-(2-phenylethyl)-1-piperazinyl]-benzo[b]thiophene-2-carboxamide;
c) 4-[4-(2-phenylethyl)-1-piperazinyl]-benzo[b]thiophene-2-nitrile;
d) 4-[4-(3-phenylpropyl )-1-piperazinyl ]-benzo[b ]thiophene-2-methanol;
e) 4-[4-(3-phenylpropyl)-1-piperazinyl]-benzo[b]thiophene-2-carboxamide;
f) 4-[4-[2-(4-methoxyphenyl )ethyl ]-1-piperazinyl]-benzo [b ]thiophene-2-methanol;
g) 4-[4-[2-(4-chlorophenyl)ethyl]-1-piperazinyl]-benzo[b]thiophene-2-carboxamide;
h) 4-[4-[2-(4-chlorophenyl)ethyl]-1-piperazinyl]-benzo [b ]thiophene-2-methanol;
i) 4-[4-[2-(4-methylphenyl)ethyl]-1-piperazinyl]-benzo[b]thiophene-2-methanol;
j) 4- [4- (2-phenylethyl) -1-piperazinyl]-benzo[b ]thiophene-2-(N-methyl) -carboxamide;
k) 4-[4-(2-phenylethyl)-1-piperazinyl]-benzo[b]thiophene-2-(N,N-dimethyl)-carboxamide;
l) 4-[4-[2-(4-methylphenyl)ethyl]-1-piperazinyl]-benzo[b]thiophene-2-carboxamide;
m) 4-[4-[2-(4-fluorophenyl)ethyl]-1-piperazinyl]-benzo [b ]thiophene-2-methanol;
n) 4-[4-[2-(4-fluorophenyl)ethyl]-1-piperazinyl]-benzo[b]thiophene-2-carboxamide;
o) Ethyl 4-[(4-propyl)-1-piperazinyl]benzo[b]thiophene-2-carboxylate hydrochloride;
p) 4-[(4-propyl)-1-piperazinyl]benzo[b]thiophene-2-methanol hydrochloride;
q) 4-[4-(2-phenylethyl)-1-piperazinyl ]-benzo[b]thiophene-2-(N-ethyl)carboxamide hydrochloride;
r) 4-[4-(2-phenylethyl)-1-piperazinyl]-benzo[b]thiophene-2-(O-methyl)-methanol hydrochloride;
s) 4-[4-propyl-1-piperazinyl]-benzo[b]thiophene-2-[N-methyl]carboxamide hydrochloride; 0.4 hydrate;;
t) 4-[4-methyl-1-piperazinyl]-benzo[b]thiophene-2-methanol hydrochloride;
u) 4-[4-( 2-phenylethyl )-1-piperazinyl]-benzo[b]thiophene-2-(N- methyl-N-methoxy)-carboxamide hydrochloride;
v) 2-[4-[4-( 2-phenylethyl )-1-piperazinyl]benzo[b]thiophene-2-]-(2-propanol) hydrochloride; hemihydrate;
w) 1-[4-(4-phenethyl-piperazin-1-yl)-benzo[b]thiophen-2-yl]-ethanone hydrochloride;
x) 1-[4-(4-phenethyl-piperazin-1-yl)-benzo[b]thiophen-2-yl]-ethanol hydrochloride;
y) 4-[4-phenylmethyl-1-piperazinyl]-benzo[b]thiophene-2-methoxymethyl hydrochloride;
z) 4- (1-piperazinyl)-benzo[b]thiophene-2-methoxymethyl hydrochloride;
aa) 4-[4-(2-(4-fluorophenyl)-ethyl)-1-piperazinyl]benzo [b]thiophene 2-methoxymethyl hydrochloride;
bb) 4-[4-(2-phenylethyl)-1-piperazinly]-benzo[b]thiopene-2-carboxaldehyde;
cc) 4-[4-(4-phenylcarbomoyl-butyl)-piperazin-1-yl]-benzo [b]thiopen-2-carboxylic acid ethyl ester hydrochloride;
dd) 4-(1-piperazinyl)benzo[b]thiophene-2-( N-methyl)-carboxamide:
ee) 4- 4-[2-(4-nitrophenyl)ethyl]-1-piperazinyl]-benzo [b]thiophene-2-methanol hydrochloride dihydrochloride;
ff) 4-(1-piperazinyl)benzo[b]thiophene-2-methanol hydrochloride;
gg) Ethyl 4-[4-[2-(4-nitrophenyl)ethyl]-1-piperazinyl benzo [b]thiophene-2-carboxylate hydrochloride;
hh) 5-[4-(2- Hydroxymethyl-benzo[b]thiophen-4-yl)-piperazin-1-yl)-pentanoic acid phenyl amide hydrochloride;
ii) 2-[4-(4-phenethyl-piperazin-1-yl)-benzo[b]thiophen-2-ylmethyl]-isoindole-1,3-dione hydrochloride;
jj) 4-[4-(2-phenylethyl)-1-piperazinyl]-benzo[b]thiophene-2-methanamine dihydrochloride;
kk) [4-(4-phenthyl-piperazin-1-yl)-benzo[b]thiophen-2-yl]-piperidin-1- yl methanone hydrochloride;
ll) [4-(4-phenethyl-piperazin-1-yl)-benzo[b]thiophen-2-yl]pyrrolidin-1-yl methanone hydrochloride;
mm) 3-[4-(4-phenethyl-piperazin-1-yl)-benzo[b]thiophen-2-yl]-acrylic acid ethyl ester hydrochloride: yl]-acrylic acid ethyl ester hydrochloride;
nn) 3-[4-(4-phenethyl-piperazin-1-yl)-benzo[b]thiophen-2-yl]-prop-2-en-1-ol hydrochloride;
oo) 3-[4-(4-phenethyl-piperazin-1-yl)-benzo[b]thiophen-2-yl]-acrylonitrile hydrochloride;
pp) 3-[4-(4-phenethyl-piperazin-1-yl)-benzo[b]thiophen-2-yl]-acrylamide hydrochloride;
qq) 3-[4-(4-phenethyl-piperazin-1-yl)-benzo[b]thiophen-2-yl]-propionic acid ethyl ester hydrochloride;
rr) 3-[4-(4-phenethyl-piperazin-1-yl)-benzo[b]thiophen-2-yl]-propan-1-ol hydrochloride;
ss) 3-[4-(4-phenethyl-piperazin-1-yl)-benzo[b]thiophen-2-yl]-propionitrile hydrochloride;

tt) 3-[4-(4-phenethyl-piperazin-1-yl)-benzo[b]thiophen-2-yl]-propionamide hydrochloride;

The compounds of Formula I can be prepared using techniques known in the art. One suitable method is disclosed below in Reaction Scheme I for preparing those compounds in which Y is represented by —(CH$_2$)$_n$X$_1$, in which n is O. All the substituents, unless otherwise indicated, are previously defined. The reagents and starting materials for use in this process are readily available to one of ordinary skill in the art.

to provide the substitution product described by structure (2).

For example, in step A, the appropriately substituted 2,6-difluorobenzaldehyde of structure (1) is combined with a slight excess of the appropriate piperazine, such as 1-benzylpiperazine, in a suitable organic solvent, such as N,N-dimethylformamide. A slight excess of a suitable weak base, such as potassium carbonate, is added and the reaction is heated to about 80° C. for approximately 4 hours. After cooling, the substitution product de-

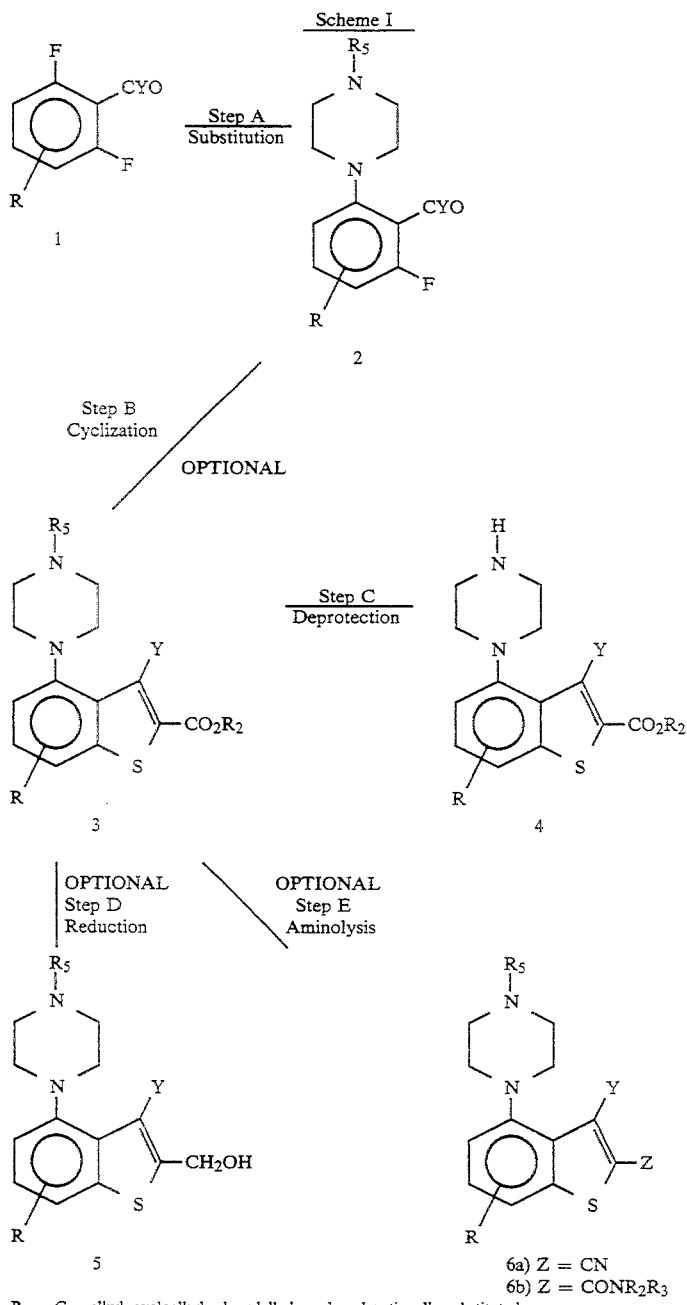

R$_5$ = C$_{1-4}$ alkyl, cycloalkyl, phenylalkyl or phenyl optionally substituted In step A, the substitution reaction is performed following generally the procedure of Nijhuis et al. *Synthesis-Stuttgart* 1987, 7, 641, by treating the appropriately substituted 2,6-difluorobenzaldehyde or 2,6-difluoroacetophenone described by structure (1) (i.e., R and Y as desired in the final product) with the appropriately substituted piperazine under mild basic conditions scribed by structure (2) is then isolated by extraction. It is then purified by flash chromatography with a suitable eluent, such as a 30:70 mixture of ethyl acetate:hexane and recrystallized from a suitable solvent, such as hot ethyl acetate.

In step B, the cyclization is performed following generally the procedure of Scroweton et al. *J. Chem. Soc. Perkin Trans. I* 1976, 749, by treating structure (2) with the appropriately substituted alkyl 2-mercaptoacetate under strongly basic conditions to provide the cyclized product of Formula I in which X is an ester derivative, hereinafter structure (3). Examples of an appropriately substituted alkyl mercaptan are ethyl-2-mercaptoacetate, methyl-2-mercaptoacetate and the like.

For example, in step B, the substitution product described by structure (2) is dissolved in a suitable anhydrous organic solvent, such as N,N-dimethylformamide under a suitable inert atmosphere, such as nitrogen. A slight excess of an appropriate alkyl 2-mercaptoacetate, such as ethyl-2-mercaptoacetate is added followed by a slight excess of a suitable strong base, such as sodium hydride. The reaction is allowed to stir at room temperature for about 6 hours. The cyclization product of structure (3) is then isolated by extraction as the free base. It is then purified by flash chromatography with a suitable eluent, such as a 50:50 mixture of ethyl acetate:hexane and recrystallized from a suitable solvent, such as acetonitrile. The free base is then converted to the acid addition salt of structure (3) by treatment with a suitable acid, such as hydrochloric acid and recrystallization from a suitable solvent, such as acetonitrile.

Depending upon the desired product of Formula I, it may be necessary to carry out the functionalization reactions depicted in optional steps C through E above. The particular substituent that X or $R_5$ will be represented by is depicted in each reaction.

In step C, the deprotection is performed following generally the procedure of Senet et al., *J. Org. Chem.* 1984, 49, 2081, by treating the cyclization product (3) with 1-chloroethyl chloroformate to provide the compounds of Formula I in which $R_5$ is H (hereinafter structure 4).

For example, in step C, the cyclization product (3) is dissolved in a suitable organic solvent, such as 1,2-dichloroethane, under an atmosphere of nitrogen and cooled to approximately 0° C. One to three molar equivalents of 1-chloroethyl chloroformate are added and the reaction is warmed to room temperature. After stirring for about 30 minutes, the reaction is heated at reflux for about 4.5 hours. After cooling and removal of solvent under vacuum, a volume of ethanol equivalent to the original organic solvent volume is added and the reaction again is heated at reflux for about 1.5 hours. It is then stirred at room temperature for about 15 hours. The solvent is then removed under vacuum and structure 4 is purified as the acid addition salt by recrystallization from a suitable solvent, such as warm ethanol.

In step D, the optional reduction is performed by treating the cyclization product (3) with a suitable reducing agent to provide the compounds of Formula I in which X contains an alcohol, hereinafter structure (5).

For example, in step D, the cyclization product (3) is dissolved in a suitable anhydrous organic solvent, such as tetrahydrofuran, under an atmosphere of an inert gas, such as nitrogen. To the solution, 2 equivalents of a suitable reducing agent, such as lithium aluminum hydride is added and the reaction is allowed to stir at room temperature for about 1 to 4 hours. The reaction is quenched by sequential addition of water, 10% sodium hydroxide and then additional water in a ratio of 1.0:1.5:3.0 by volume where the first addition of water is equivalent to the amount of lithium aluminum hydride used by weight. For example, 1 g of lithium aluminum hydride requires 1 mL of water. The resulting structure 5 is then isolated by extraction as the free base. It is then purified by flash chromatography with a suitable eluent, such as a 40:60 to 100:0 mixture of ethyl acetate:hexane. The free base is then converted to the acid addition salt of structure (5) by treatment with a suitable acid, such as hydrochloric acid and recrystallized from a suitable solvent, such as acetonitrile/ethanol.

The optional aminolysis of Step E is carried out if X is to be represented by a nitrile or amido function. In step E, the aminolysis is performed following generally the procedure of Weinreb et al. *Tetrahedron Lett.* 1977, 4171 and *Syn. Comm.* 1982, 12, 989. Treatment of the cyclization product described by structure 3 with an appropriate amine source in the presence of trimethyl aluminum provides the amide or nitrile depicted above as structure 6a or 6b. Examples of an appropriate amine source are ammonium chloride, aniline, benzylamine, methylamine, dimethylamine, ethylamine, cyclopropylamine, cyclohexylamine and the like.

For example, in step E, an appropriate amine source, such as ammonium chloride is treated with an equivalent of trimethyl aluminum in a suitable anhydrous organic solvent, such as dichloromethane. After gas evolution subsides (about 5 to 30 minutes), 0.2 to 1.0 molar equivalents of the cyclization product described by (3) are added and the reaction is refluxed for approximately 10 to 20 hours. After cooling, the reaction is cautiously quenched with water. The nitrile and the amide described by structures (6a) and (6b) are isolated by extraction. They are then separated and purified as free bases by flash chromatography with a suitable eluent, such as 40:60 to 100:0 mixture of ethyl actetate:hexane. They are then converted to the acid addition salts of structures (6a) and (6b) by treatment with a suitable acid, such as hydrochloric acid and triturated with a suitable solvent, such as ether.

The substituents at the 4-position of the piperazine ring can be readily modified as depicted below in Reaction Scheme II.

Scheme II

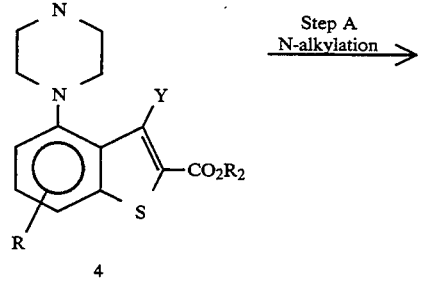

Step A
N-alkylation

-continued
Scheme II

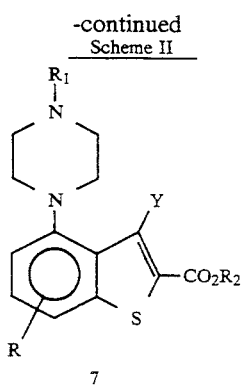
7

Scheme I
Steps D or E → isolated by extraction as the free base. It is then purified by flash chromatography with a suitable eluent, such as a 20:80 to 100:0 mixture of ethyl acetate:hexane. The free base is then converted to the acid addition salt of structure (7) by treatment with a suitable acid, such as hydrochloric acid and recrystallized from a suitable solvent, such as methanol or methanol:acetonitrile.

The N-alkylated product described by structure (7) can then be converted to the alcohol of structure (5), the amide of structure (6b) or the nitrile of structure (6a) following steps D or E of Scheme I which was previously described, wherein $R_5$ is replaced by $R_1$.

Following the procedure described in Scheme III, the compounds of Formula I wherein $n=1$ and $X_1=CO_2R_2$ can be prepared.

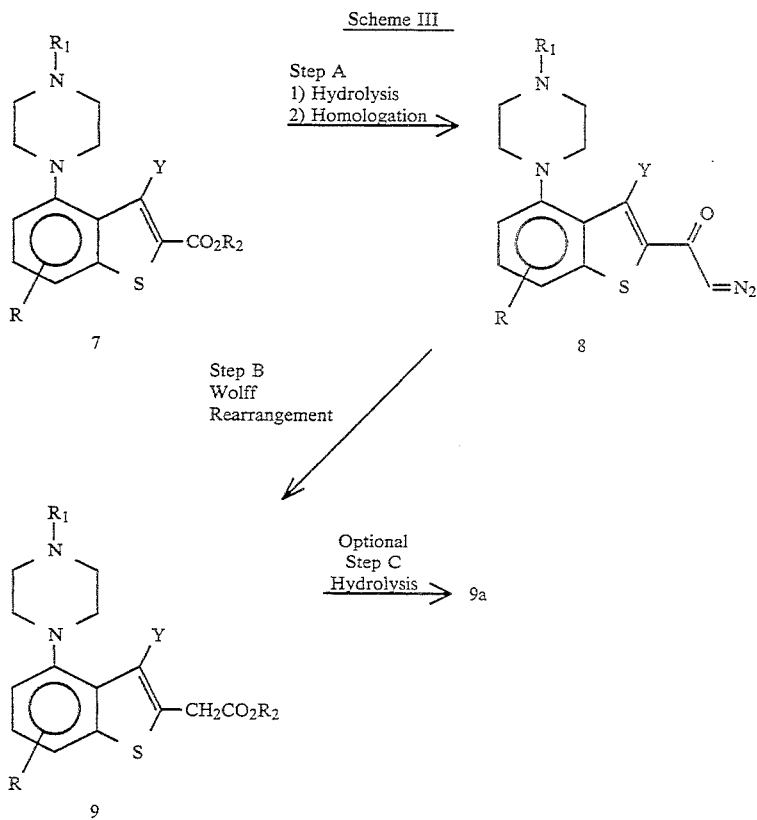

In step A, the deprotected product described by structure (4) prepared in Scheme I can be treated with an appropriately substituted alkyl halide under mild basic conditions to provide the N-alkylated product of Formula I hereinafter structure (7). Examples of appropriately substituted alkyl halides are 1-bromo-3-phenylpropane, (2-bromoethyl)-benzene, 1-bromo-4-butylbenzene, 4-methoxyphenethyl bromide, 6-bromo-N-phenyl-1-hexanamide, 7-bromo-N-(4-methylphenyl)-1-heptanamide and the like.

For example, in step A the acid addition salt of the deprotected product described by structure (4) is dissolved in a suitable anhydrous organic solvent, such as dimethyl sulfoxide or dimethylformamide. An equivalent of an appropriately substituted alkyl halide, such as 1-bromo-3-phenylpropane is added followed by two equivalents of a suitable mild base, such as sodium bicarbonate. The reaction is heated to about 80° C. for approximately 15 to 20 hours. After cooling, the N-alkylated product described by structure (7) is then In step A1, the ester in structure (7) can be hydrolyzed to the carboxylic acid by techniques well known to one skilled in the art. For example, the ester (7) can be treated with 1 equivalent of a suitable base, such as lithium hydroxide in a suitable water miscible solvent, such as methanol or tetrahydrofuran. After 12 to 48 hours the reaction is treated with 1 equivalent of a suitable aqueous acid, such as hydrochloric acid and then concentrated under vacuum. The residue can be purified by chromatography with a suitable eluent such as 5:95 acetic acid:acetonitrile to provide the carboxylic acid derivative of structure (7) wherein $R_2=H$.

In step A2, a one carbon homologation of the acid can then be performed by first dissolving the carboxylic acid of structure (7) in a suitable organic solvent, such as dichloromethane at a concentration of 0.2 to 1.0M. This solution can then be treated with one equivalent of thionyl chloride and a catalytic amount of dimethylformamide to provide the acid chloride of structure (7)

wherein $R_2$=Cl. The organic solvent is removed under vacuum and the crude acid chloride is dissolved in anhydrous ether (0.1 to 1.0M) and treated with a solution of diazomethane in ether until diazomethane is no longer absorbed. The alpha-diazoketone described by structure (8) is then isolated by techniques well known to one skilled in the art.

In step B, the alpha-diazoketone (8) can undergo a Wolff Rearrangement by treatment with ethanol and silver benzoate as described by V. Lee and M. S. Newman, *Organic Syntheses* 1970, 50, 77 to provide the one carbon homologated ester described by structure (9).

In optional step C, the one carbon homologated ester described by structure (9) can be converted to the carboxylic acid (9a) wherein $R_2$=H following generally the procedure previously described in Scheme III, step A1.

Following the procedure described in Scheme IV, the compounds of Formula I in which n=2 and $X_1$=$CO_2R_2$ can be prepared.

furan and treated with N-methyl-O-methylhydroxylamine to provide the amide of structure (10).

In step B, the amide of structure (10) can then be reduced to the aldehyde described by structure (11) by treatment with 1–3 equivalents of diisobutyl aluminum hydride as described in *Tetrahedron Lett.* 1984, 25(15), 1561 or by treatment with 1–3 equivalents of lithium aluminum hydride in tetrahydrofuran as described in *Tetrahedron Lett.* 1989, 30(29), 3779.

In step C, the aldehyde of structure (11) can undergo a two carbon homologation through a modified Wittig Reaction as described by W. S. Wadsworth, *Organic Synthesis* 1977, 25, 73 or alternatively by the procedure of A. Suzuki et al. *Tetrahedron Lett.* 1989, 30(38), 5153. Treatment of the aldehyde (11) with an appropriately substituted phosphonate anion provides the $\gamma,\beta$-unsaturated ester. This can be reduced by treatment with a suitable reducing agent, such as nickel borohydride as described in *J. Chem. Soc., Perkin Transactions I* 1982, 2405 to provide the saturated ester described by

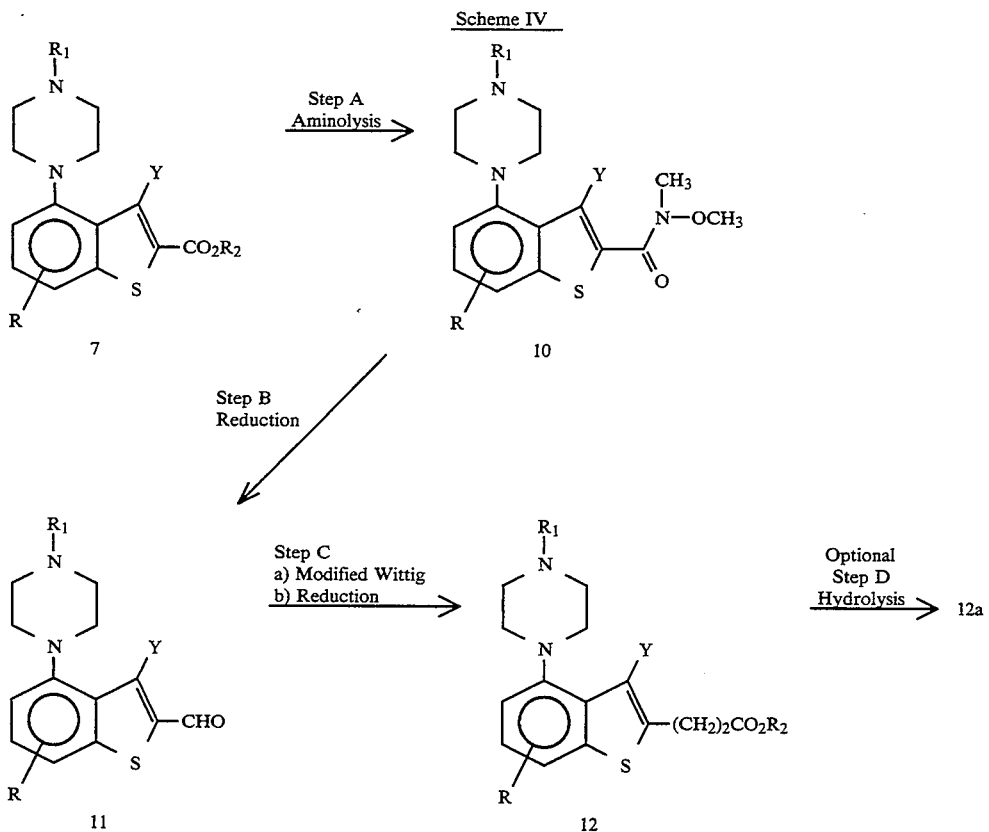

structure (12).

In optional step D, the saturated ester (12) can be converted to the saturated carboxylic acid (12a) wherein $R_2$=H following generally the procedure previously described in Scheme III, step A1.

Following the procedure described in Scheme V, the compounds of Formula I wherein X=$CHX_2$-$(CH_2)_q$-$CH_3$ can be prepared.

In step A, aminolysis of structure (7) following generally the procedure previously described in Scheme I, step E in which the amine used is N-methyl-O-methyl hydroxlyamine, provides the amide of structure (10). Alternatively, the acid chloride intermediate described in Scheme III, step A2 in which $R_2$=Cl can be dissolved in a suitable organic solvent, such as tetrahydro-

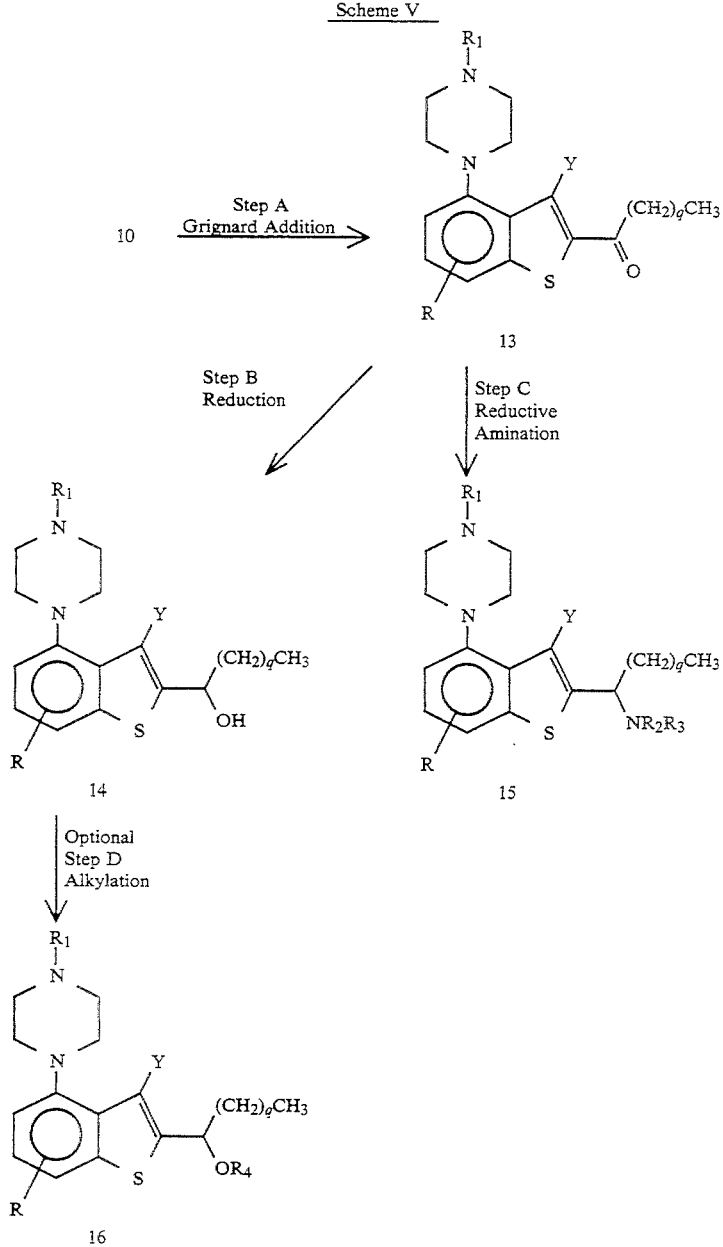

Scheme V

In step A, the amide of structure (10) can be treated with a Grignard reagent to provide the ketone described by structure (13). For example, the amide (10) is dissolved in a suitable organic solvent, such as ether or tetrahydrofuran at 0° C. and treated with the appropriately substituted Grignard Reagent of formula $CH_3(CH_2)_qMgX$ wherein $X=Br$ or $Cl$. After about 1–4 hours the product is isolated by treatment with water and extraction into a suitable organic solvent, such as ether. This is then purified by flash chromatography using a suitable eluent, such as 50:50 ethyl acetate:hexane to provide the ketone of structure (13).

In step B, the ketone of structure (13) can be treated with a reducing agent to provide the alcohol described by structure (14). For example, the ketone (13) is dissolved in a suitable organic solvent, such as ethanol or isopropanol at room temperature. The reaction is then treated with one to two equivalents of a suitable reducing agent, such as sodium borohydride. After 1–4 hours, the reaction is diluted with water and extracted with a suitable organic solvent, such as dichloromethane. The crude material can be purified as previously described in step A by flash chromatography to provide the alcohol of structure (14).

In step C, the ketone of structure (13) can also be reductively aminated following generally the procedure described by Borch et al. *J. Am. Chem. Soc.* 1971, 93, 2897 to provide the amine described by structure (15). For example, the ketone (13) is dissolved in a suitable organic solvent, such as methanol in a concentration of 0.5 to 1.0M. The reaction is then treated with five to ten equivalents of the appropriately substituted amine hydrochloride of formula $NHR_2R_3 \cdot HCl$ at room temperature. The reaction is then treated with one to two equivalents of a suitable reducing agent, such as sodium cyanoborohydride and allowed to stir for 12–72 hours. The reaction is then treated with aqueous sodium hydroxide, stirred 1-2 hours, diluted with water and extracted with a suitable organic solvent, such as dichloromethane. The crude product can then be purified by flash chromatography using a suitable eluent, such as triethylamine:ethanaol:ethyl acetate, 5:10:90. In cases where a secondary amine hydrochloride is utilized, the reaction may be heated to 40°-65° C. or the reaction modified by addition of titanium isopropoxide as described in *J. Org. Chem.* 1990, 55, 2552 to provide the amine of structure (15).

In optional step D, the alcohol (14) can be alkylated to provide the ether described by structure (16). For example, the alcohol (14) is dissolved in a suitable polar, aprotic organic solvent, such as dimethylformamide and treated with an equivalent of a suitable strong base, such as sodium hydride at room temperature. After the gas evolution subsides, the rearion is treated with one equivalent of an appropriate alkylating agent of formula $R_2X$ in which $X=Br$, Cl or I. Examples of appropriate alkylating agents are methyl iodide, n-propyl bromide, benzyl bromide and the like. After 2-24 hours the reaction is diluted with water and extracted with a suitable organic solvent, such as ether. The crude product is purified by techniques well known to one skilled in the art, such as flash chromatography or recrystallization of the acid addition salt to provide the ether of structure (16).

Following the procedure in Scheme VI, the compounds of Formula I in which $X=-(CH_2)_nX_1$ can be prepared.

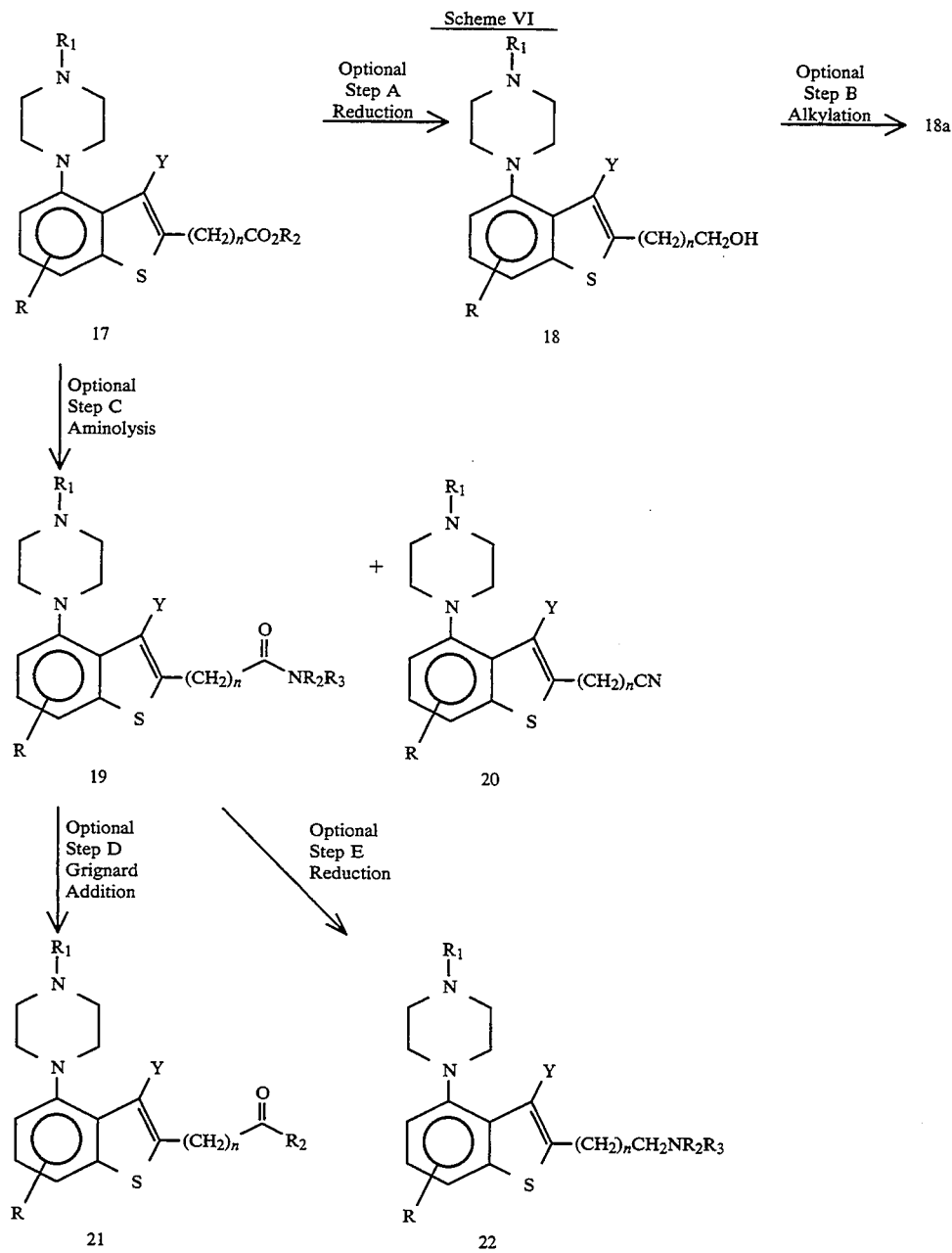

Scheme VI

In optional step A, the ester described by structure (17) in which $n=0-2$, which can be prepared as described in Schemes I-III, can be reduced to the alcohol described by structure (18) following generally the procedure described in Scheme I, step D.

In optional step B, the alcohol (18) can be alkylated following generally the procedure described in Scheme V, step D to provide the corresponding ether (18a).

In optional step C, the ester described by structure (17) can undergo an aminolysis following generally the procedure described in Scheme I, step E to provide the amide of structure (19) and the nitrile of structure (20).

In optional step D, the amide (19), in which $R_2=OCH_3$ and $R_3=CH_3$, can undergo a Grignard addition following generally the procedure described in Scheme V, step A to provide the ketone of structure (21).

In optional step E, the amide (19) can be reduced to the amine of structure (22). For example, the amide (19) is dissolved in a suitable organic solvent, such as tetrahydrofuran at a concentration of 0.2–1.0M and treated with 2–4 equivalents of a suitable reducing agent. Examples of a suitable reducing agent are lithium aluminum hydride, diisobutyl aluminum hydride and the like. The reaction is heated under an inert atomosphere, such as nitrogen at 40° C. to reflux for 4–48 hours. The reaction is quenched and the crude product isolated following generally the procedure described in Scheme I, step D. The crude product is purified by flash chromatography using a suitable eluent, such as diethylamine:ethanol:ethyl acetate, 10:50:50 to provide the amine of structure (22).

The starting materials and reagents for use in Schemes I through VI are readily available to one of ordinary skill in the art.

The following examples present typical syntheses as described by Scheme I and Scheme II. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "°C." refers to degrees Celsius, "TLC" refers to thin layer chromatography, "$R_f$" refers to retention factor, "μL" refers to microliters, "δ" refers to parts per million down field from tetramethylsilane, and "Ph" refers to a phenyl ring when depicted in a structure.

In the following examples, the compounds binding affinity for both the $5HT_{1A}$ receptor and $5HT_{1D}$ receptors is reported. The compounds affinity for the $5HT_{1D}$ site was determined by the binding procedure of Peroutka et al as reported in *European Journal of Pharmacology*, Vol. 163 at pages 133–166 (1989). The compounds affinity for the $5HT_{1A}$ receptor was determined by the procedure of Gozlan et al., as reported in *Nature*, Volume 305, at pages 140–142 (1983). Where multiple determinations of the binding affinity have been performed, the average is given followed by the number of determinations in parentheses. Also, the $PA_2$ value for the saphenous vein preparation as described in this application is given, followed by the intrinsic (agonist) activity in parentheses, expressed as a percentage.

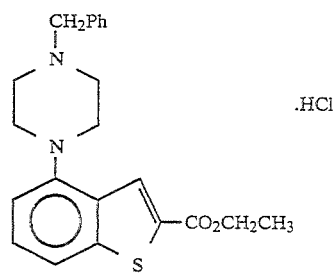

Preparation of ethyl-4-[4-(phenylmethyl)-1-piperazinyl]benzo[b]thiophene-2-carboxylate monohydrochloride Scheme I, step A; Combine 2,6-difluorobenzaldehyde (5.00 g, 35.2 mmol), 1-benzylpiperazine (7.30 mL, 42.2 mmol) and potassium carbonate (5.83 g, 42.2 mmol) in dry N,N-dimethylformamide (10 mL) under an atmosphere of nitrogen. Heat the reaction to 80° C. for 4 hours. Cool the reaction to room temperature (20° C.) and stir overnight. Quench the reaction with water (100 mL) and extract with ethyl acetate (3×100 mL). Combine the organic extracts, wash with saturated ammonium chloride (4×100 mL), dry over anhydrous magnesium sulfate/sodium sulfate, filter and concentrate under vacuum to provide the crude product as a yellow oil. Purify the crude material by flash chromatography (ethyl acetate:hexane, 30:70, TLC $R_f$=0.40) followed by recrystallization from hot ethyl acetate (50 mL). Collect the crystals by suction filtration and rinse with hexane to yield 5.16 g. Concentrate the mother liquor and recrystallize the solid from ethyl acetate (15 mL). Isolate the crystals as above to yield 1.71 g. Repeat the above process to yield an additional 0.95 g. This provides the 2-fluoro-6-[4-benzylpiperazin-1-yl]-benzaldehyde (7.82 g) as yellow crystals, mp 94°–95° C.; $^1H$ NMR (CDCl₃) δ 10.26 (1H,-s), 7.44 (1H, td, J=8.1, 6.3 Hz), 7.34 (4H, m), 7.29 (1H, m), 6.84 (1H, d, J=8.3 Hz), 6.74 (1H, dd, J=8.3, 8.0 Hz), 3.59 (2H, s), 3.12 (4H, m), 2.66 (4H, m); $^{13}C$ NMR (CDCl₃) δ 187.63, 187.56, 165.73, 162.27, 155.82, 137.82, 135.62, 135.46, 129.20, 128.27, 127.18, 116.91, 116.82, 114.26, 114.22, 109.38, 109.09, 62.95, 53.51, 52.96; $^{19}F$ NMR CDCl3) δ −115.94 (m); IR (KBr) 2825, 1690, 1607, 1462, 1005 cm$^{-1}$; EI/MS (70eV) 298(80%), 91(100%).

Anal. Calc. for $C_{18}H_{19}FN_2O$: C, 72.45; H, 6.43; N, 9.38. Found: C, 72.31; H, 6.58; N, 9.27.

Scheme I, step B; Dissolve 2-fluoro-6-[4-benzylpiperazin-1-yl]-benzaldehyde (7.73 g, 25.9 mmol) in dry N,N-dimethylformamide (130 mL) under an atmosphere of nitrogen. Add ethyl-2-mercaptoacetate (4.30 mL, 38.9 mmol) and sodium hydride (1.55 g of a 60% mineral oil dispersion, 38.9 mmol) and stir at room temperature for 6 hours. Add 10% sodium hydroxide (60 mL) and extract the reaction with ether (4×100 mL). Combine the organic extracts, rinse with water (2×200 mL), brine (100 mL), dry over anhydrous magnesium sulfate/sodium sulfate, filter and concentrate under vacuum to provide the crude product as a yellow oil. Purify the crude material by flash chromatography (ethyl acetate:hexane, 20:80, TLC $R_f$=0.60) and recrystallize from acetonitrile (25 mL). Collect the crystals by suction filtration to yield 8.12 g. Concentrate the mother liquor and recrystallize the residue as above to yield an additional 0.60 g. This provides the free base of the title compound (8.72 g) as orange crystals, mp 81°–83° C.; $^1$H NMR (CDCl$_3$) δ 8.11 (1H, s), 7.48 (1H, d, J=8.2 Hz), 7.32 (6H, m), 6.88 (1H, d, J=7.7 Hz), 4.40 (2H, q, J=7.2 Hz), 3.63 (2H, s), 3.19 (4H, t, J=4.75 Hz), 2.72 (4H, t, J=4.75 Hz), 1.42 (3H, t, J=7.2 Hz); $^{13}$C NMR (CDCl$_3$) δ 162.93, 150.22, 143.77, 137.98, 133.37, 131.90, 129.27, 128.62, 128.29, 127.88, 128.17, 116.81, 112.68, 63.14, 61.52, 53.37, 52.38, 14.36; IR (KBr) 2937, 1709, 1257, 1243, 1243, 1230 cm$^{-1}$; EI/MS(70Ev) 380(90%), 91(100%).

Anal. Calc. for $C_{22}H_{24}N_2O_2S$: C, 69.45; H, 6.37; N, 7.36. Found: C, 69.27; H, 6.47; N, 7.41.

Dissolve the free base of the above compound (2.00 g, 5.3 mmol) in ethanol (50 mL) and add 1.0M hydrochloric acid (5.5 mL) to the solution. Concentrate under vacuum and recrystallize the residue with acetonitrile to provide the title compound (1.89 g) as a white solid, mp 232°–234° C.; $^1$H NMR (DMSO-d$_6$) δ 11.42 (1H, bs), 8.09 (1H, s), 7.74 (3H, m), 7.49 (4H, m), 7.04 (1H, d, J=7.7 Hz), 4.43 (2H, d, J=4.94 Hz), 4.37 (2H, q, J=7.1 Hz), 3.54 (2H, bd), 3.34 (4H, m), 2.51 (2H, m), 1.35 (3H, t, J=7.1 Hz); 13C NMR (DMSO-d$_6$) δ 161.93, 148.33, 142.85, 132.64, 131.98, 131.60, 129.71, 129.54, 128.82, 128.40, 127.92, 118.05, 113.71, 61.58, 58.70, 50.86, 14.25; IR (KBr) 1718, 1246, 753 cm$^{-1}$; CI/MS (CH$_4$) 380 (100%).

IC$_{50}$= >1000 nM (5HT$_{1A}$ Binding Affinity)
IC$_{50}$= >1000 nM (5HT$_{1D}$ Binding Affinity)

Anal. Calc. for $C_{22}H_{24}N_2O_2S \cdot HCl$: C, 63.37; H, 6.06; N, 6.72.

Found: C, 63.23; H, 6.12; N, 6.57.

EXAMPLE 2

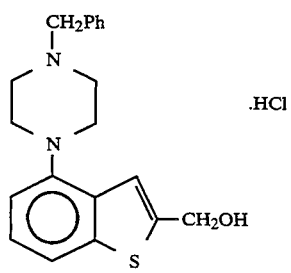

Preparation of
4-[4-(phenylmethyl)-1-piperazinyl]-benzo[b]thiophene-
2-methanol monohydrochloride Scheme I, step D; Dissolve ethyl-4-[4-(phenylmethyl)-1-piperazinyl]-benzo[b]thiophene-2-carboxylate (1.50 g, 3.94 mmol, prepared in example 1), in dry tetrahydrofuran (40 mL). Add lithium aluminum hydride (0.30 g, 7.89 mmol) and stir the reaction at 20° C. under an atmosphere of nitrogen for 26 hours. Heat the reaction to reflux for 3 hours. After cooling to room temperature, add water (0.3 mL), 10% sodium hydroxide (0.45 mL) and an additional amount of water (1.8 mL). Dilute the reaction with water (50 mL) and extract with ether (3×50 mL). Combine the organic extracts, wash with brine (50 mL), dry over anhydrous magnesium sulfate/sodium sulfate, filter and concentrate under vacuum. Purify the crude yellow residue by flash chromatography (ethyl acetate:hexane, 40:60, TLC R$_f$=0.30, then 100:0) to yield the free base as a pale yellow solid. Dissolve in warm ethanol (50 mL), add 1M hydrochloric acid (4 mL) and concentrate under vacuum. Recrystallize the residue from acetonitrile (15 mL) and ethanol (20 mL) to provide the title compound (1.08 g) as yellow crystals, mp 229–231° C.; $^1$H NMR (CD$_3$OD) δ 7.60 (3H, m), 7.53 (3H, m), 7.34 (1H, s), 7.25 (1H, t, J=7.9 Hz), 6.96 (1H, dd, J=0.7, 7.7 Hz), 4.86 (2H, d, J=0.9 Hz), 3.53 (6H, bm), 3.31 (2H, bm); $^{13}$C NMR (CD$_3$OD) δ 147.41, 146.92, 142.80, 135.35, 132.55, 131.39, 130.43, 130.18, 125.92, 119.38, 113.91, 61.63, 60.74, 53.35, 50.25; IR (KBr) 3386, 1456, 951 cm$^{-1}$; CI/MS (CH$_4$) 321(100%), 339(95%). IC$_{50}$=35 nM (5HT$_{1A}$ Binding Affinity) IC$_{50}$=760 nM (5HT$_{1D}$ Binding Affinity)

Anal. Calc. for $C_{20}H_{22}N_2OS \cdot HCl \cdot 0.05\ CH_3CH_2OH$: C, 64.01; H, 6.24; N, 7.43. Found: C, 64.06; H, 6.30; N, 7.03.

EXAMPLE 3

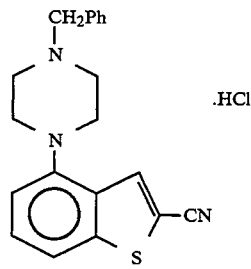

Preparation of
4-[4-(phenylmethyl)-1-piperazinyl]-benzo[b]thiophene-
2-nitrile monohydrochloride Scheme I, step E; Add trimethyl aluminum (11.8 mL of a 2M solution in toluene, 23.7 mmol) to dry ammonium chloride (1.27 g, 23.7 mmol) in anhydrous dichloromethane (155 mL) at room temperature. After 33 minutes, add ethyl-4-[4-(phenylmethyl)-1-piperazinyl]-benzo[b]thiophene-2-carboxylate (3.00 g in 27 mL of dichloromethane, 7.89 mmol, prepared in example 1) and heat at reflux under nitrogen for 21 hours. Cool the reaction, cautiously pour into water (250 mL) and extract with dichloromethane (3×100 mL). Combine the organic extracts and wash with brine (100 mL), dry over anhydrous magnesium sulfate/sodium sulfate, filter and concentrate under vacuum. Separate the free base from the resulting mixture by flash chromatography (ethyl acetate:hexane, 40:60, TLC R$_f$=0.4, then 100:0) to yield 0.62 g. Dissolve the free base in ethanol (25 mL), treat with 1M hydrochloric acid (2 mL) and concentrate under vacuum. Triturate the solid with ether (20 mL) and heat at 150° C. for 3 days under vacuum to provide the title compound (0.68 g) as a tan solid, mp 256°–259° C. dec.; $^1$H NMR (DMSO-d$_6$) δ 11.56 (1H, bs), 8.49 (1H, s), 7.80 (1H, d, J=8.1 Hz), 7.71 (2H, bs), 7.57–7.49 (4H, m), 7.06 (1H, d, J=7.6 Hz), 4.43 (2H, bs), 3.57 (2H, bm), 3.37 (6H, bm); $^{13}$C NMR (DMSO-d$_6$) δ 148.05, 142.50, 134.81, 131.60, 131.43, 131.33, 129.51, 129.26, 128.73, 117.49, 114.74, 113.85, 107.07, 58.51, 50.74, 48.27; IR (KBr) 1564, 1456, 953, 699 cm−1; EI/MS (70 eV) 333(54%), 91(100%). IC$_{50}$=180 nM (5HT$_{1A}$ Binding Affinity) IC$_{50}$= >1000 nM (5HT$_{1D}$ Binding Affinity)

Anal. Calc. for $C_{20}H_{19}N_3S \cdot HCl$: C, 64.95; H, 5.46; N, 11.36. Found: C, 65.06; H, 5.52; N, 11.11.

EXAMPLE 4

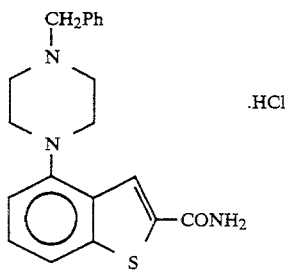

Preparation of 4-[4-(phenylmethyl)-1-piperazinyl]-benzo[b]thiophene-2-carboxamide monohydrochloride Scheme I, step E; The free base of the title compound is also produced from the reaction in example 3 and is separated from the mixture by flash chromatography (ethyl acetate:hexane, 40:60, TLC $R_f$=0.1, then 100:0) to yield 2.26 g. Dissolve the free base in ethanol (100 mL), treat with 1M hydrochloric acid (6.5 mL) and concentrate under vacuum. Triturate the solid with ether (40 mL) to provide the title compound (2.28 g) as a pale yellow powder, mp 192–195° C., $^1$H NMR (DMSO-$d_6$) δ 11.51 (1H, bs), 8.40 (1H, s), 8.15 (1H, s), 7.69 (4H, m), 7.49 (3H, m), 7.38 (1H, t, J=7.9 Hz), 6.95 (1H, d, J=7.6 Hz), 4.46 (2H, d, J=5.1 Hz), 3.43 (8H, m); $^{13}$C NMR (DMSO-$d_6$) δ 163.20, 147.57, 141.97, 139.13, 133.04, 131.54, 129.58, 129.59, 128.77, 126.95, 123.06, 117.46, 112.69, 58.47, 55.98, 50.86, 48.14; IR (KBr) 1658, 1604, 1567, 1458, 1390, 953 cm$^{-1}$; CI/MS (CH$_4$) 352(100%). IC$_{50}$=1.6 (2) nM (5-HT$_{1A}$ Binding Affinity) IC$_{50}$=52 nM (5-HT$_{1D}$ Binding Affinity) Anal. Calc. for C$_{20}$H$_{21}$N$_3$OS•HCl•0.5CH$_3$CH$_2$OH: C, 61.38; H, 6.15; N, 10.22. Found: C, 61.09; H, 6.09; N, 10.29.

EXAMPLE 5

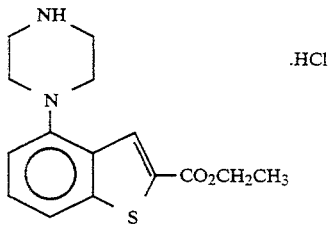

Preparation of ethyl 4-(1-piperazinyl)-benzo[b]thiophene-2-carboxylate monohydrochloride Scheme I, step C; Dissolve ethyl-4-[4-(phenylmethyl)-1-piperazinyl]-benzo[b]thiophene-2-carboxylate (2.00 g, 5.26 mmol, prepared in example 1) in 1,2-dichloroethane (40 mL) under an atmosphere of nitrogen and cool the solution with an ice bath. Add 1-chloroethyl chloroformate (1.40 mL, 13.1 mmol) and warm the reaction to room temperature (20° C.). Stir for 30 minutes and then heat the reaction to reflux for 4.5 hours. After cooling, concentrate under vacuum, add ethanol (40 mL) to the residue, reflux for 1.5 hours under nitrogen and then stir at room temperature for 15 hours. Concentrate under vacuum and recrystallize the residue from warm ethanol (50 mL). Collect the product by suction filtration and wash with ether to provide the title compound (1.14 g) as a white solid, mp 238°–240° C.; $^1$H NMR (DMSO-$d_6$) δ 9.43 (2H, bs), 8.13 (1H, s), 7.75 (1H, d, J=8.2 Hz), 7.49 (1H, t, J=7.9 Hz), 7.06 (1H, d, J=7.5 Hz), 4.37 (2H, q, J=7.1 Hz), 3.34 (8H, bs), 1.35 (3H, t, J=7.1 Hz); $^{13}$C NMR (DMSO-$d_6$) δ 161.90, 148.81, 142.84, 132.69, 131.91, 128.35, 128.01, 117.91, 113.64, 61.50, 48.88, 43.01, 14.17; IR (KBr) 1711, 1281, 1246, 756 cm$^{-1}$; EI/MS (70eV) 290(55%), 248(100%). IC$_{50}$=89 nM (5HT$_{1A}$ Binding Affinity) IC$_{50}$=47 nM (5HT$_{1D}$ Binding Affinity)

Anal. Calc. for C$_{15}$H$_{18}$N$_2$O$_2$S•HCl•0.75H$_2$O: C, 52.94; H, 6.08; N, 8.23. Found: C, 53.00; H, 6.15; N, 8.01.

EXAMPLE 6

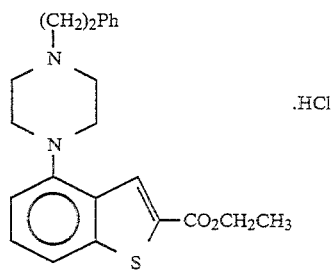

Preparation of ethyl-4-[4-(2-phenylethyl)-1-piperazinyl]-benzo[b]thiophene-2-carboxylate monohydrochloride Scheme I, step A; Combine 2,6-difluorobenzenaldehyde (7.48 g, 52.3 mmol) and 1-(2-phenylethyl)-piperazine (10.94 g, 57.5 mmol)[evolution of heat]. Add dry dimethylformamide (55 mL) and potassium carbonate (7.95 g, 57.5 mmol). With stirring, heat the reaction at 75°–85° C. for 7 hours under nitrogen. Add ice water (200 mL) and extract the reaction with ether (250 mL). Wash the organic extract with brine (2×50 mL), dry over anhydrous magnesium sulfate, filter and concentrate under vacuum to yield a brown oil which solidifies on standing. Purify by flash chromatography (ethyl acetate:hexane, 50:50, TLC $R_f$=0.3, then 100:0) to provide 4-(2-phenylethyl)-1-(3-carboxy-2-fluorophenyl)-piperazine (10.24 g) as a yellow solid, mp 85.5°–87.5° C.; $^1$H NMR (CDCl$_3$) δ 10.28 (1H, s), 7.45 (1H, dt, J=6.4, 8.2 Hz), 7.33–7.21 (5H), 6.86 (1H, d, J=8.1 Hz), 6.75 (1H, dd, J=8.2, 10.4 Hz), 3.16 (4H, m), 2.85 (2H, m), 2.76–2.66 (6H); $^{13}$C NMR (CDCl$_3$) δ 187.48, 187.41, 165.96, 162.51, 155.62, 155.57, 140.10, 135.66, 135.50, 128.74, 128.67, 128.49, 128.41, 126.11, 116.98, 116.88, 114.28, 114.24, 109.45, 109.16, 77.20, 60.28, 53.53, 53.43, 53.06, 52.97, 33.57; $^{19}$F NMR (CDCl$_3$) δ -115.980 (dd, J=32, 51 Hz); IR (CHCl$_3$ solution) 2832, 1688, 1609, 1472, 1450, 1236, 1005, 754 cm$^{-1}$; CI/MS (CH$_4$) 313(100%), 221(52%).

Anal. Calc. for C$_{19}$H$_{21}$FN$_2$O: C, 73.05; H, 6.78; N, 8.97. Found: C, 72.76; H, 6.79; N, 8.74.

Scheme I, step B; Add ethylmercaptoacetate (4.93 mL, 45.0 mmol) to a stirred solution of 4-(2-phenylethyl)-1-(3- carboxy-2-fluorophenyl)-piperazine (9.97 g, 30.0 mmol) in dry dimethylformamide (100 mL) under nitrogen. Cool the reaction with an ice bath and treat with sodium hydride (1.80 g of a 60% oil dispersion, 45.0 mmol) over 3 minutes (gas evolution). Remove the cooling bath after 20 minutes. After 6 hours add an additional amount of sodium hydride (0.18 g) and ethylmercaptoacetate (0.5 mL) to the yellow, cloudy reaction. Stir for 24 hours and pour into water (300 mL). Extract with ether (500 mL), wash the extract with water (100 mL), brine (100 mL), dry over anhydrous magnesium sulfate, filter and concentrate under vacuum. Purify the residue by flash chromatography (ethyl acetate:hexane, 50:50, TLC $R_f=0.6$) to provide the free base (10.15 g) of the title compound as a yellow solid, mp 97.5°–100.0° C.; $^1$H NMR (CDCl$_3$) δ 8.13 (1H, s), 7.49 (1H, d, J=8.2 Hz), 7.38 (1H, d, J=7.8 Hz), 7.34–7.31 (6H), 6.91 (1H, d, J=7.5 Hz), 4.40 (2H, q, J=7.1 Hz), 3.22 (4H, m), 2.89–2.72 (8H), 1.42 (3H, t, J=7.1 Hz); $^{13}$C NMR (CDCl$_3$) δ 162.86, 150.09, 143.76, 140.21, 133.34, 131.95, 128.67, 128.53, 128.38, 127.84, 126.06, 116.86, 112.67, 61.47, 60.44, 53.42, 52.34, 33.62, 14.31; IR (CHCl$_3$ solution) 2824, 1707, 1456, 1283, 1258, 1238 cm$^{-1}$; CI/MS (CH$_4$) 395(100%), 303(70%). IC$_{50}$=37 nM (5HT$_{1A}$ Binding Affinity) IC$_{50}$=108 nM (5HT$_{1D}$ Binding Affinity)

Anal. Calc. for C$_{23}$H$_{26}$N$_2$O$_2$S: C, 70.02; H, 6.64; N, 7.10. Found: C, 69.82; H, 6.73; N, 7.11.

Alternative method for preparation of the title compound

Scheme II, step A; Dissolve ethyl-4-(1-piperazinyl)-benzo[b]thiophene-2-carboxylate monohydrochloride (2.50 g, 8.61 mmol, prepared in example 5) in dimethyl sulfoxide (45 mL), add (2-bromoethyl)-benzene (1.20 mL, 8.61 mmol) and sodium bicarbonate (0.72 g, 8.6 mmol). Stir the reaction overnight at room temperature and then at 80° C. for 4 hours. After cooling, add saturated sodium bicarbonate (50 mL), water (150 mL) and extract with ether (4×100 mL). Combine the ether extracts, wash with water (100 mL), brine (100mL), dry over anhydrous magnesium sulfate/sodium sulfate, filter and concentrate under vacuum. Purify the residue by flash chromatography (ethyl acetate:hexane, 20:80, TLC $R_f=0.5$, then 40:60) to yield the free base (2.20 g) as orange crystals. Dissolve the free base (0.95 g) in dichloromethane (2 mL) and ethanol (50 mL), add 1M hydrochloric acid (2.5 mL) and concentrate under vacuum. Triturate the solid with ether (20 mL) to yield the title compound (0.96 g) as a white solid, mp 237°–240° C.; $^1$H NMR (DMSO-d$_6$) δ 11.42 (1H, bs), 8.11 (1H, s), 7.77 (1H, d, 8.2 Hz), 7.47 (1H, t, J=7.9 Hz), 7.33 (5H, m), 7.08 (1H, d, J=7.6 Hz), 4.37 (2H, q, J=7.2 Hz), 3.66 (2H, bd), 3.57 (2H, bd), 3.39 (6H, m), 3.16 (2H, m), 1.35 (3H, t, J=7.0 Hz); $^{13}$C NMR (DMSO-d$_6$) δ 161.88, 148.25, 142.82, 137.08, 132.63, 131.98, 128.66, 128.34, 127.83, 126.79, 118.00, 113.70, 1.50, 56.22, 51.05, 48.83, 29.26, 14.18; IR (KBr) 1709, 1245, 755, cm$^{-1}$; CI/MS (CH$_4$) 395(100%), 303(85%).

Anal. Calc. for C$_{23}$H$_{26}$N$_2$O$_2$S•HCl: C, 64.10; H, 6.33; N, 6.50. Found: C, 64.08; H, 6.30; N, 6.72.

EXAMPLE 7

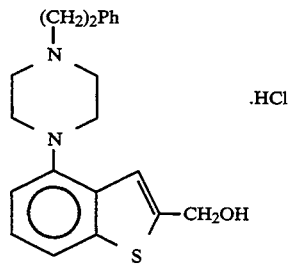

Preparation of 4[4(2-phenylethyl)-1-piperazinyl]-benzo[b]thiophene-2-methanol monohydrochloride Scheme I, step D; In an analogous manner to example 2, the title compound (1.05 g) as a tan solid is prepared from ethyl-4-[4-(2-phenylethyl)-1-piperazinyl]benzo[b]thiophene-2-carboxylate (1.20 g, 3.04 mmol, prepared in example 7) and lithium aluminum hydride (0.23 g, 6.08 mmol); mp 230°–232° C. $^1$H NMR (DMSO-d$_6$) δ 11.31 (1H, bs), 7.62 (1H, d, J=8.1 Hz), 7.32 (7H, m), 6.95 (1H, d J=7.3 Hz), 4.76 (2H, s), 3.69 (2H, bd) , 3.55 (2H, bd), 3.40 (6H, m), 3.21 (2H, m); $^{13}$C NMR (DMSO-d$_6$) δ 146.68, 146.08, 140.27 , 137.07, 133.24, 128.67, 126.80, 124.60, 117.73, 112.59, 58.91, 56.19, 51.21, 48.36, 29.30; IR (KBr) 3282, 2545, 1447, 959 cm$^{-1}$; CI/MS (CH$_4$) 335(100%), 353(95%). IC$_{50}$=0.6(2) nM (5HT$_{1A}$ Binding Affinity) IC$_{50}$=2.4(2) nM (5HT$_{1D}$ Binding Affinity)

Anal. Calc. for C$_{21}$H$_{24}$N$_2$OS•HCl: C, 64.85; H, 6.49; N, 7.20. Found: C, 64.59; H, 6.46; N, 7.23.

EXAMPLE 8

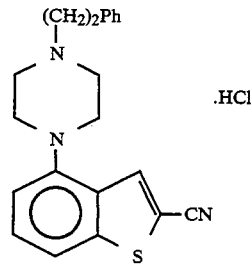

Preparation of 4-[4-(2-phenylethy-1-piperazinyl]-benzo[b]thiophene-2-nitrile monohydrochloride Scheme I, step E; In an analogous manner to example 3, the title compound (0.60 g) as a white solid, mp 252°–255° C., is prepared from ethyl-4-[4-(2-phenylethyl)-1-piperazinyl]benzo[b]thiophene-2-carboxylate (1.73 g, 4.39 mmol, prepared in example 6), dry ammonium chloride (0.70 g, 13.2 mmol) and 2M trimethyl aluminum in toluene (6.6 mL, 13.2 mmol) . The free base is isolated by flash chromatography (ethyl acetate:hexane, 40:60, TLC $R_f=0.4$, then ethanol:ethyl acetate, 50:50); $^1$H NMR (DMSO-d$_6$) δ 11.39 (1H, bs), 8.51 (1H, s), 7.82 (1H, d, J=8.2 Hz), 7.57 (1H, t, J=8.0 Hz), 7.34 (5H, m), 7.11 (1H, d, J=7.6 Hz), 3.65 (4H, m), 3.38 (6H, m), 3.16 (2H, m); $^{13}$C NMR (DMSO-d$_6$) δ 148.03, 142.48, 137.05, 134.78, 131.42, 129.21, 128.65, 126.78, 117.53, 114.7 2, 113.99, 107 . 11, 56.09, 51.06, 48.49, 29.26; IR (KBr) 2215, 1564, 1456, 960 cm$^{-1}$; CI/MS (CH$_4$) 348(88%), 256(100%). IC$_{50}$=4 nM (5HT$_{1A}$ Binding Affinity) IC$_{50}$=18(2) nM (5HT$_{1D}$ Binding Affinity)

Anal. Calc. for C$_{21}$H$_{21}$N$_3$S•HCl: C, 65.70; H, 5.79; N, 10.94. Found: C, 65.44; H, 5.80; N, 10.92.

EXAMPLE 9

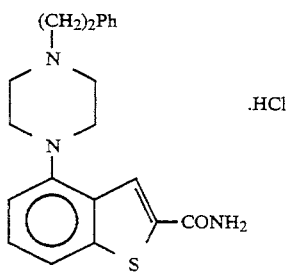

Preparation of 4-[4-(2-phenylethyl)-1-piperazinyl]-benzo[b]thiophene-2-carboxamide monohydrochloride Scheme I, step E; The free base of the title compound is isolated during the separation step in example 8 by flash chromatography(ethyl acetate:hexane, 40:60, $R_f=0.1$, then ethanol:ethyl acetate, 50:50) to yield 0.96 g. Dissolve the free base in dichloromethane (10 mL) and ethanol (50 mL). Add 1M hydrochloric acid (3 mL) and concentrate under vacuum. Triturate the solid with ether (50 mL) and collect by suction filtration to provide the title compound (0.91 g) after drying under vacuum at 120° C. for 2 days; mp>280° C. $^1$H NMR (DMSO-d$_6$) δ 11.44 (1H, bs), 8.42 (1H, s), 8.20 (1H, s), 7.67 (2H, t, J=4.0 Hz), 7.34 (6H, m), 6.99 (1H, d, J=7.6 Hz), 3.73 (2H, bd), 3.64 (2H, bd), 3.39 (6H, m), 3.17 (2H, m); $^{13}$C NMR (DMSO-d$_6$) δ 163.21, 147.59, 141.98, 139.15, 137.05, 133.13, 128.77, 128.66, 126.96, 126.79, 123.13, 117.50, 112.77, 56.07, 51.22, 48.33, 29.36; IR (KBr) 1653, 1598, 1455, 1394 cm$^{-1}$; CI/MS (CH$_4$) 366(100%). IC$_{50}$=0.5 nM (5HT$_{1A}$ Binding Affinity) IC$_{50}$=1.6(2) nM (5HT$_{1D}$ Binding Affinity) pA$_2$=7.99 (blocking of 5-HT1-like-mediated contraction in canine saphenous vein)

Anal. Calc. for C$_{21}$H$_{23}$N$_3$OS•HCl: C,62.75; H, 6.03; N, 10.45. Found: C, 62.47; H, 6.10; N, 10.26.

EXAMPLE 10

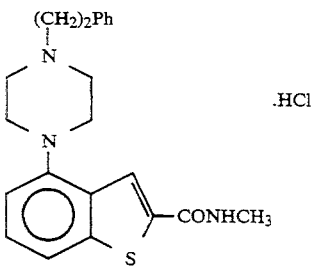

Preparation of 4-[4-(2-phenylethyl)-1-piperazinyl]-benzo[b]thiophene-2-(N-methyl)-carboxamide monohydrochloride Scheme I, step E; To a suspension of methylamine hydrochloride (0.42 g, 6.0 mmol) in dry toluene (10 mL), add trimethyl aluminum (2M solution in toluene, 3.0 mL, 6.0 mmol) over 5 minutes (vigorous gas evolution). After 10 minutes add ethyl-4-[4-(2-phenylethyl)-1-piperazinyl]-benzo[b]thiophene-2-carboxylate (1.24 g, 3.0 mmol, prepared in example 6). Stir the reaction at 20° C. for 18 hours and then 60° C. for 6 hours. After cooling, cautiously add water (30 mL) and extract with dichloromethane (4×50 mL). Combine the organic extracts, dry over anhydrous sodium sulfate, filter and concentrate under vacuum. Purify the residue by flash chromatography (ethanol:ethyl acetate, 0:100, TLC $R_f$=0.4, then 20:80). Dissolve the free base in hot ethanol (50 mL), add 1M hydrochloric acid (3.0 mL) and concentrate under vacuum. Recrystallize from hot acetonitrile (50 mL) and a small amount of ether to provide the title compound (1.10 g) as a tan solid, mp 256°–258° C.; $^1$H NMR (DMSO-d$_6$) δ 11.36 (1H, bs), 8.98 (1H, m), 8.20 (1H, s), 7.68 (1H, d, J=8.1 Hz), 7.42–7.28 (7H), 7.00 (1H, d, J=7.6 Hz), 3.75 (2H, m), 3.64 (2H, m), 3.40 (m), 3.18 (2H, m), 2.84 (3H, d, J=4.5 Hz); $^{13}$C NMR (DMSO-d$_6$) δ 6 161.81, 147.52, 141.58, 138.89, 137.03, 133.10, 128.68, 128.66, 126.87, 126.80, 122.26, 117.52, 112.86, 56.10, 51.27, 48.36, 29.37, 26.01; IR (KBr) 3271, 1651, 1547, 1456, 1251, 970 cm$^{-1}$; CI/MS (CH$_4$) 380(100%), 288(60%). IC$_{50}$=1 nM (5HT$_{1A}$ Binding Affinity) IC$_{50}$=1 nM (5HT$_{1D}$ Binding Affinity) pA$_2$=10.6 (25%) (blocking of 5-HT1-like-mediated contraction in canine saphenous vein)

Anal. Calc. for C$_{22}$H$_{25}$N$_3$OS•HCl: C, 63.53; H, 6.31; N, 10.10. Found: C, 63.45; H, 6.36; N, 10.40.

EXAMPLE 11

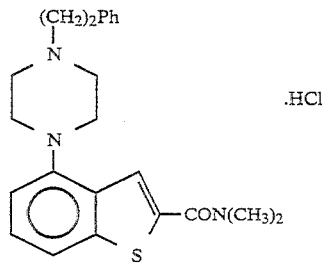

Preparation of 4-[4-(2-phenylethyl)-1-piperazinyl]-benzo[b]thiophene-2-(N,N-dimethyl)-carboxamide monohydrochloride Scheme I, step E; In an analogous manner to example 10, the title compound (1.10 g) as a white solid, mp 253°–255° C., is prepared from ethyl-4-[4-(2-phenylethyl)-1-piperazinyl]benzo[b]thiophene-2-carboxylate (1.24 g, 3.0 mmol, prepared in example 6), dimethylamine hydrochloride (0.489 g, 6.0 mmol) and trimethyl aluminum (2M solution in toluene, 3.0 mL, 6.0 mmol). The reaction time is 1.5 hours at 20° C. and then 20 hours at 60° C.; 1H NMR (DMSO-d$_6$) δ 11.48 (1H, bs), 7.74 (1H, s), 7.70 (1H, d, J=8.1 Hz), 7.43–7.28 (7H), 7.03 (1H, d, J=7.6 Hz), 3.75 (2H, bd), 3.64 (2H, bd), 3.42–3.23 (m), 3.35 (6H, s), 3.23–3.03 (broad multiplet); $^{13}$C NMR (DMSO-d$_6$) δ 163.36, 147.44, 140.75, 137.08, 136.67, 132.56, 128.65, 126.77, 126.73, 123.16, 117.41, 113.18, 56.15, 51.07, 48.54, 29.25; IR (KBr) 1616, 1454, 1392, 752 cm$^{-1}$; CI/MS (CH$_4$) 394(100%), 302(55%). IC$_{50}$=2.3 nM (5HT$_{1A}$ Binding Affinity) IC$^{50}$=3 nM (5HT$_{1D}$ Binding Affinity) pA$_2$=9.01 (2%) (blocking of 5-HT1-like-mediated contraction in canine saphenous vein)

Anal. Calc. for C$_{23}$H$_{27}$N$_3$OS•HCl: C, 64.25; H, 6.56; N, 9.77. Found: C, 64.21; H, 6.60; N, 9.79.

EXAMPLE 12

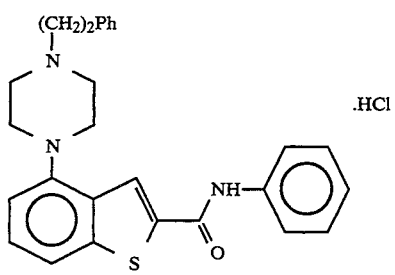

Preparation of 4-[4-(2-phenylethyl)-1-piperazinyl]-benzo[b]thiophene2-(N-phenyl)-carboxamide monohydrochloride Scheme I, step E; To a solution of aniline (0.41 mL, 4.5 mmol) in dry dichloromethane (10 mL) under nitrogen, add trimethyl aluminum (2M solution in toluene, 2.25 mL, 4.5 mmol) over 5 minutes (slow gas evolution). After 10 minutes add ethyl-4-[4-(2-phenylethyl)-1-piperazinyl]benzo[b]thiophene-2-carboxylate (1.24 g, 3.0 mmol, prepared in example 6). Stir the reaction for 20 hours at 20° C., then reflux for 8 hours and stir for an additional 18 hours at 20° C. Pour the reaction into water (100 mL), add propanol:dichloromethane (20:80, 50 mL) and stir for 30 minutes. Separate the organic phase and again extract the aqueous with propanol:dichloromethane (20:80, 50 mL).

Combine the organic extracts, dry over anhydrous magnesium sulfate, filter and concentrate under vacuum. Purify the residue by flash chromatography (ethyl acetate:hexane, 40:60, TLC $R_f=0.3$, then 50:50 followed by 100:0) to yield the free base of the title compound (1.26 g) as a yellow solid. Dissolve the free base in acetonitrile (50 mL), add 1M hydrochloric acid (3.0 mL) and concentrate under vacuum. Triturate the residue with ether (30 mL) to provide the title compound (1.36 g) as a white solid, mp 160°–166° C.; $^1$H NMR (DMSO-$d_6$) 11.22 (1H, bs), 10.92 (1H, s), 8.62 (1H, s), 7.87 (2H, d, J=7.5 Hz), 7.73 (1H, d, J=8.2 Hz), 7.46–7.28 (8H), 7.16 (1H, t, J=7.3 Hz), 7.04 (1H, d, J=7.6 Hz), 3.76–3.66 (4H), 3.30 (2H, m), 3.19–3.13 (2H, m); $^{13}$C NMR (DMSO-$d_6$) 160.31, 147.88, 142.00, 138.87, 138.59, 136.99, 133.19, 128.67, 128.59, 127.28, 126.80, 123.93, 123.92, 120.74, 117.57, 113.09, 56.10, 51.33, 48.48, 29.35; IR (KBr) 3431, 1649, 1599, 1539, 1440, 1319, 1246, 754 cm$^{-1}$; CI/MS (CH$_4$) 442(100%), 350(40%). IC$_{50}$=85 nM (5HT$_{1A}$ Binding Affinity) IC$_{50}$=220 nM (5HT$_{1D}$ Binding Affinity) pA$_2$=7.74 (0%) (blocking of 5-HT1-like-mediated contraction in canine saphenous vein)

Anal. Calc. for C$_{27}$H$_{27}$N$_3$OS•HCl•0.8H$_2$O: C, 65.85; H, 6.05; N, 8.53. Found: C, 65.81; H, 6.06; N, 8.51.

EXAMPLE 13

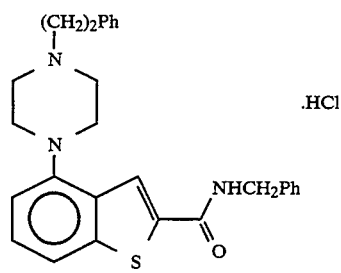

Preparation of 4-[4-(2-phenylethyl)-1-piperazinyl]-benzo[b]thiophene-2-(N-phenylmethyl)-carboxamide monohydrochloride Scheme I, step E; In an analogous manner to example 12, the title compound (1.26 g) as a white solid, mp slowly softens 190°–220° C. to a liquid 230° C., is prepared from ethyl-4-[4-(2-phenylethyl)-1-piperazinyl]-benzo[b]thiophene-2-carboxylate (1.24 g, 3.0 mmol, prepared in example 6), benzylamine (4.5 mmol) and trimethyl aluminum (2M solution in toluene, 2.25 mL, 4.5 mmol). The reaction is heated to reflux for 18 hours and extracted with dichloromethane. The free base is purified by flash chromatography ( ethyl acetate:hexane, 50:50, TLC $R_f=0.2$, then 100:0); $^1$H NMR (DMSO-$d_6$) δ 11.62 (1H, bs), 9.73 (1H, bt, J=6.1 Hz), 8.38 (1H, s), 8.33 (2H, bs), 7.69 (1H, d, J=8.2 Hz), 7.43–7.25 (12H), 7.00 (1H, d, J=7.6), 4.53 (2H, d, J=6.0 Hz), 3.73–3.62 (4H), 3.45–3.34 (6H), 3.20–3.15 ( 2H, m); $^{13}$C NMR ( DMSO-$d_6$) δ 161.49, 147.65, 141.75, 139.37, 138.78, 137.07, 133.16, 128.66, 128.30, 127.31, 126.99, 126.83, 126.78, 122.73, 117.52, 112.90, 56.07, 51.22, 48.34, 42.51, 29.30; IR (KBr) 3429, 3317, 2430, 1643, 1547, 1446, 1427, 1271, 754 cm$^{-1}$; CI/MS (CH$_4$) 456(100%), 364(35%). IC$_{50}$=27 nM (5HT$_{1A}$ Binding Affinity) IC$_{50}$=31 nM (5HT$_{1D}$ Binding Affinity) pA$_2$=8.76 (0%) (blocking of 5-HT1-like-mediated contraction in canine saphenous vein)

Anal. Calc. for C$_{28}$H$_{29}$N$_3$OS•2HCl: C, 63.63; H, 5.91; N, 7.95. Found: C, 63.53; H, 5.99; N, 7.95.

EXAMPLE 14

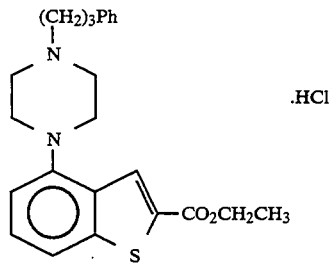

Preparation of ethyl-4-[4-(3-phenylpropyl)-1-piperazinyl]-benzo[b]thiophene-2-carboxylate monohydrochloride Scheme II, step A; In an analogous manner to example 6, the title compound (0.99 g) as a tan solid, mp 210.5°–213° C., is prepared from ethyl-4-(1-piperazinyl)-benzo[b]thiophene-2-carboxylate monohydrochloride (2.40 g, 8.27 mmol, prepared in example 5), dry dimethyl sulfoxide (45 mL), 1-bromo-3-phenylpropane (1.20 mL, 8.27 mmol) and sodium bicarbonate (0.69 g, 8.27 mmol). Recrystallize the title compound from warm methanol (10 mL); 1H NMR (DMSO-d$_6$) δ 11.05 (bs), 7.76 (1H, d, J=8.2 Hz), 7.49 (1H, t, J=7.9 Hz), 7.28 (5H, m), 7.06 (1H, d, J=7.6 Hz), 4.37 (2H, q, J=7.2 Hz) 3.62 (2H, bd), 3.53 (2H, bd), 3.32 (4H, m), 3.18 (2H, m), 2.69 (2H, m), 1.34 (3H, t, J=7.1 Hz); $^{13}$C NMR (DMSO-d$_6$) δ 161.86, 148.25, 142.82, 140.49, 132.62, 131.96, 128.41, 128.33, 128.23, 127.86, 126.11, 117.96, 113.65, 61.49, 55.24, 51.03, 48.76, 32.07, 24.71, 14.16; IR (KBr) 2970, 1709, 1284, 1258 cm$^{-1}$; CI/MS (CH$_4$) 409(100%), 408(75%). IC$_{50}$=239 nM (5HT$_{1A}$ Binding Affinity) IC$_{50}$=551 nM (5HT$_{1D}$ Binding Affinity)

Anal. Calc. for C$_{24}$H$_{28}$N$_2$O$_2$S•HCl: C, 64.78; H, 6.58; N, 6.29. Found: C, 64.71; H, 6.51; N, 6.02.

EXAMPLE 15

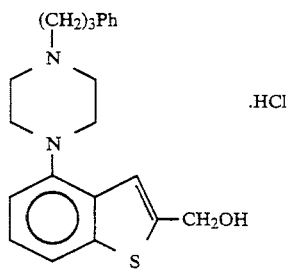

Preparation of
4-[4-(3,phenylpropyl)-1-piperazinyl]-benzo[b]thiophene-2-methanol monohydrochloride Scheme I, step D; In an analogous manner to example 2, the title compound (1.29 g) as a tan solid, mp 166°–169° C., is prepared from ethyl-4-[4-(3-phenylpropyl)-1-piperazinyl]-benzo[b]thiophene-2-carboxylate (1.60 g, 9.92 mmol, prepared in example 14), dry tetrahydrofuran (40 mL) and lithium aluminum hydride (0.30 g, 7.83 mmol); $^1$H NMR (DMSO-d$_6$) δ 11.02 (1H bs), 7.61 (1H, d, J=7.9 Hz), 7.29 (7H, m), 6.93 (1H, d, J=7.5 Hz), 5.62 (1H, bs), 4.75 (2H, s), 3.61 (2H, bd), 3.49 (2H, bd), 3.25 (4H, m), 2.68 (2H, t, J=7.7 Hz), 2.10 (2H, m); $^{13}$C NMR (DMSO-d$_6$) δ 146.62, 146.06, 140.48, 140.24, 133.23, 128.40, 128.21, 126.09, 124.58, 117.73, 117.56, 112.52, 58.89, 55.19, 51.19, 48.29, 32.05, 24.71; IR (KBr) 1454, 1014, 959, 699 cm$^{-1}$; CI/MS (CH$_4$) 349(100%), 367(98%). IC$_{50}$=1.8 nM (5HT$_{1A}$ Binding Affinity) IC$_{50}$=23(2) nM (5HT$_{1D}$ Binding Affinity)

Anal. Calc. for C$_{22}$H$_{26}$N$_2$OS•HCl: C, 65.57; H, 6.77; N, 6.95. Found: C, 65.48; H, 6.84; N, 6.80.

EXAMPLE 16

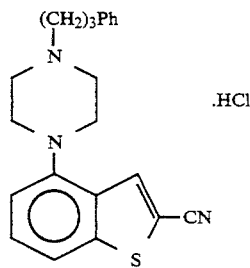

Preparation of
4-[4-(3-phenylpropyl)-1-piperazinyl]-benzo[b]thiophene-2-nitrile monohydrochloride Scheme I, step E; Add dry dichloromethane (100 mL) to dry ammonium chloride (0.820 g, 15.3 mmol) and treat with trimethyl aluminum (7.8 mL of a 2M solution in toluene, 15.3 mmol). After 30 minutes, add a solution of ethyl-4-[4-(3-phenylpropyl)-1-piperazinyl]-benzo[b]thiophene-2-carboxylate (2.09 g, 5.12 mmol, prepared in example 14) in dry dichloromethane (19 mL) to the reaction and heat at reflux for 19 hours. After cooling, cautiously pour the reaction into water (200 mL) and extract with dichloromethane (4×100 mL). Combine the organic extracts and wash with brine (100 mL), dry over anhydrous magnesium sulfate/sodium sulfate, filter and concentrate under vacuum. The free base is separated from the resulting mixture by flash chromatography (ethyl acetate:hexane, 40:60, TLC R$_f$=0.4) to yield 0.69 g. Dissolve the free base in ethanol (25 mL) and treat with 1M hydrochloric acid (2 mL) and concentrate under vacuum. Triturate the solid with ether (30 mL) and collect by suction filtration to provide the title compound (0.73 g) as an off white solid, 241°–245° C. dec; $^1$H NMR (DMSO-d$_6$) δ 11.19 (1H, bs), 8.48 (1H, s), 7.81 (1H, d, J=8.2 Hz), 7.55 (1H, t, J=7.9 Hz) 7.28 (5H, m), 7.08 (1H, d, J=7.6 Hz), 3.55 (4H, m), 3.21 (6H, m), 2.69 (2H, t, J=7.8 Hz), 2.10 (2H, m); $^{13}$C NMR (DMSO-d$_6$) δ 6 148.07, 142.47, 140.53, 134.77, 131.46, 129.22, 128.40, 128.22, 126.09, 117.50, 114.73, 113.95, 107.08, 55.19, 51.06, 48.52, 32.06, 24.72; IR (KBr) 2969, 2231, 2220, 1461, 1455 cm$^{-1}$; CI/MS (CH$_4$) 362(100%). IC$_{50}$=21 nM (5HT$_{1A}$ Binding Affinity) IC$_{50}$=173 nM (5HT$_{1D}$ Binding Affinity)

Anal. Calc. for C$_{22}$H$_{23}$N$_3$S•HCl: C, 66.40; H, 6.09; N, 10.56. Found: C, 66.35; H, 6.14; N, 10.60.

EXAMPLE 17

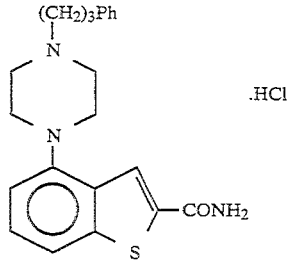

Preparation of
4-[4-(3-phenylpropyl)-1-piperazinyl]-benzo[b]thiophene-2-carboxamide monohydrochloride Scheme I, step E; The free base of the title compound is also produced from the reaction in example 16 and is separated from the mixture by flash chromatography (ethyl acetate:hexane, 40:60, TLC R$_f$=0.1) to yield 1.10 g. Dissolve the free base in ethanol (50 mL), treat with 1M hydrochloric acid (3 mL) and concentrate under vacuum. Triturate the solid with ether (50 mL) and collect by suction filtration to provide the title compound (1.08 g) as a white solid, mp 194°–196° C. dec; $^1$H NMR (DMSO-d$_6$) δ 11.12 (1H, bs), 8.37 (1H, s), 8.17 (1H, s), 7.67 (2H, d, J=8.2 Hz), 7.31 (5H, m), 6.97 (1H, d, J=7.6 Hz), 3.64 (2H, bd), 3.57 (2H, bd), 3.27 (6H, m), 2.69 (2H, t, J=7.7 Hz), 2.12 (2H, m); $^{13}$C NMR (DMSO-d$_6$) δ 163.18, 147.58, 141.98, 140.49, 139.14, 133.15, 128.42, 128.23, 126.97, 126.12, 123.13, 117.50, 112.75, 55.16, 51.24, 48.32, 32.07, 24.79; IR (KBr) 1658, 1605, 1390 cm$^{-1}$; CI/MS (CH$_4$) 380 (100%). IC$_{50}$=1 nM (5HT$_{1A}$ Binding Affinity) IC$_{50}$=4.5(2) nM (5HT$_{1D}$ Binding Affinity) pA$_2$=7.78 (blocking of 5-HT1-like-mediated contraction in canine saphenous vein)

Anal. Calc. for C$_{22}$H$_{25}$N$_3$OS•HCl•0.25H$_2$O: C, 62.84; H, 6.37; N, 9.99. Found: C, 62.62; H, 6.33; N, 9.95.

EXAMPLE 18

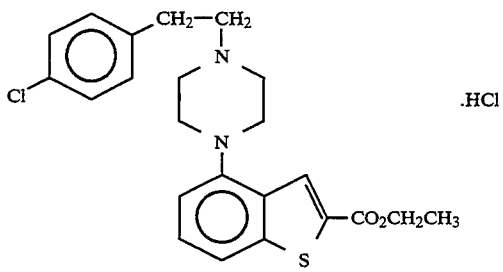

Preparation of ethyl-4-[4-[2-(4-chlorophenyl)ethyl]-1-piperazinyl]-benzo[b]thiophene-2-carboxylate monohydrochloride Scheme II, step A; In an analogous manner to example 6, the title compound (0.56 g) as a white solid, mp 263°–266° C. dec. is prepared from ethyl-4-(1-piperazinyl)benzo[b]thiophene-2-carboxylate monohydrochloride (4.63 g, 14.2 mmol, prepared in example 5), 4-chlorophenethyl bromide (3.27 g, 14.9 mmol), sodium bicarbonate (2.44 g, 29.1 mmol) and anhydrous dimethyl sulfoxide (75 mL). The title compound is recrystallized from methanol (35 mL) and acetonitrile (35 mL); $^1$H NMR (DMSO-d$_6$) δ 10.76 (1H, s), 8.10 (1H, s), 7.77 (1H, d, J=8.0 Hz), 7.44 (5H, m), 7.08 (1H, d, J=7.8 Hz), 4.37 (2H, q, J=7.0 Hz), 3.64 (4H, m), 3.56 (8H, m), 3.13 (2H, m), 1.34 (3H, t, J=7.1 Hz); $^{13}$C NMR (DMSO-d$_6$) δ 162.42, 151.71, 143.15, 132.82, 130.94, 128.95, 128.86, 128.63, 128.34, 117.59, 113.66, 113.59, 61.97, 52.66, 51.40, 31.20, 24.06, 14.47; IR (KBr) 1714, 1448, 1282, 1246, 754 cm$^{-1}$; CI/MS (CH$_4$) 429(100%). IC$_{50}$=53 nM (5HT$_{1A}$ Binding Affinity) IC$_{50}$=411 nM (5HT$_{1D}$ Binding Affinity) pA$_2$=6.51 (blocking of 5-HT1-like-mediated contraction in canine saphenous vein)

Anal. Calc. for C$_{23}$H$_{25}$ClN$_2$O$_2$S•HCl: C, 59.36; H, 5.64; N, 6.02. Found: C, 59.02; H, 5.59; N, 5.96.

EXAMPLE 19

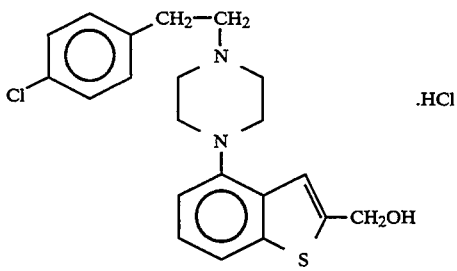

Preparation of 4-[4-[2-(4-chlorophenyl)ethyl]-1-piperazinyl]-benzo[b]thiophene-2-methanol monohydrochloride Scheme I, step D; In an analogous manner to example 2, the title compound (0.89 g) as a white solid, mp 248°–249° C. dec., is prepared from ethyl-4-[4-[2-(4-chlorophenyl)ethyl]-1-piperazinyl]-benzo[b]thiophene-2-carboxylate (1.20 g, 2.80 mmol, prepared in example 18) and lithium aluminum hydride (0.21 g, 5.6 mmol). The title compound is recrystallized from methanol (25 mL) and acetonitrile (10 mL); $^1$H NMR (CD$_3$OD) δ 7.58 (1H, d, J=8.8 Hz), 7.37 (5H, m), 7.28 (1H, t, J=7.9 Hz), 7.00 (1H, d, J=7.8 Hz), 4.87 (2H, s), 4.07 (9H, m), 3.15 (3H, m); $^{13}$C NMR (CD$_3$OD) δ 147.91, 147.51, 143.38, 136.81, 135.92, 134.81, 132.01, 130.62, 126.45, 119.92, 119.85, 114.46, 61.25, 59.20, 54.33, 51.01, 31.17; IR (KBr) 3319, 2584, 1462, 1446, 958, 779 cm$^{-1}$; CI/MS 387(100%). IC$_{50}$=2 nM (5HT$_{1A}$ Binding Affinity) IC$_{50}$=10 nM (5HT$_{1D}$ Binding Affinity)

Anal. Calc. for C$_{21}$H$_{23}$ClN$_2$OS•HCl: C, 59.58; H, 5.73; N, 6.61. Found: C, 59.59; H, 5.76; N, 6.58.

EXAMPLE 20

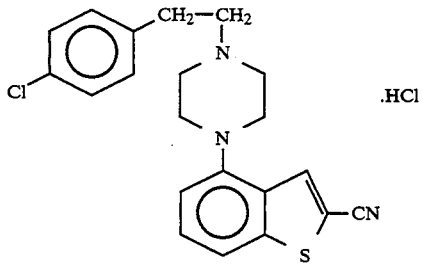

Preparation of 4-[4-[2-(4-chlorophenyl)ethyl]-1-piperazinyl]-benzo[b]thiophene-2-nitrile monohydrochloride.

Scheme I, step E; In an analogous manner to example 3, the title compound (0.39 g) as a white solid, mp 267°–269° C., is prepared from ethyl-4-[4-[2-(4-chlorophenyl)ethyl]-1-piperazinyl]-benzo[b]thiophene-2-carboxylate (1.60 g, 3.73 mmol, prepared in example 18), dry ammonium chloride (0.60 g, 11.2 mmol) and 2M trimethyl aluminum in toluene (5.6 mL, 11.2 mmol). The free base of the title compound is isolated by flash chromatography (ethyl acetate:hexane, 50:50, then ethyl acetate followed by ethanol:ethyl acetate, 50:50, R$_f$=0.4 in ethyl acetate:hexane, 40:60); $^1$H NMR (DMSO-d$_6$) δ 11.35 (1H, bs), 8.50 (1H, s), 7.82 (1H, d, J=8.2 Hz), 7.57 (1H, t, J=8.0 Hz), 7.45 (2H, d, J=8.4 Hz), 7.36 (2H, d, J=8.4 Hz), 7.10 (1H, d, J=7.6 Hz), 3.63 (4H, m), 3.37 (6H, m), 3.17 (2H, m); $^{13}$C NMR (DMSO-d$_6$) δ 148.02, 142.47, 136.12, 134.77, 131.45, 131.41, 130.58, 129.21, 128.58, 117.53, 114.72, 113.99, 107.10, 55.75, 51.10, 48.53, 28.61; IR (KBr) 2430, 2218, 1458, 958 cm$^{-1}$; CI/MS (CH$_4$) 382(100%). IC$_{50}$=13 nM (5HT$_{1A}$ Binding Affinity) IC$_{50}$=31 nM (5HT$_{1D}$ Binding Affinity) pA$_2$=7.37 (34%) (blocking of 5-HT1-like-mediated contraction in canine saphenous vein)

Anal. Calc. for C$_{21}$H$_{20}$ClN$_3$S•HCl: C, 60.29; H, 5.07; N, 10.04. Found: C, 60.14; H, 5.05; N, 9.80.

EXAMPLE 21

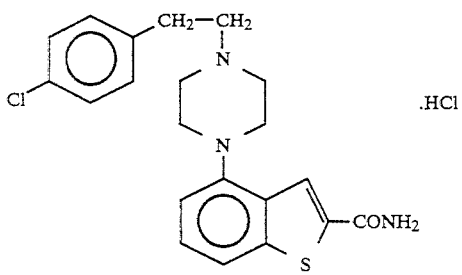

4-[4-[2-(4-chlorophenyl)ethyl]-1-piperazinyl]-benzo[b]-thiophene-2-carboxamide monohydrochloride.

Scheme I, step E; The free base of the title compound is isolated during the separation step in example 20 by flash chromatography (ethyl acetate:hexane, 40:60, TLC $R_f$=0.1, then ethanol:ethyl acetate, 50:50) to yield 0.86 g. Dissolve the free base in dichloromethane (15 mL) and ethanol (50 mL). Add 1M hydrochloric acid (2.1 mL) and concentrate under vacuum. Recrystallize the solid from warm acetonitrile (30 mL) and methanol (25 mL) to provide the title compound (0.84 g) as a tan solid, mp 263.5°–264.5° C.; $^1$H NMR (DMSO-$d_6$) δ 11.36 (1H, bs), 8.39 (1H, bs), 8.19 (1H, s), 7.68 (2H, d, J=8.1 Hz), 7.40 (5H, m), 6.99 (1H, d, J=7.5 Hz), 3.65 (4H, m), 3.38 (6H, m), 3.17 (2H, m); $^{13}$C NMR (DMSO-$d_6$) δ 163.19, 147.56, 141.97, 139.13, 136.09, 133.11, 131.47, 130.58, 128.59, 126.95, 123.10, 117.51, 112.78, 55.72, 51.24, 48.30, 28.66; IR (KBr) 3340, 1655, 1604, 1462, 1388 cm$^{-1}$; CI/MS (CH$_4$) 400(100%). IC$_{50}$=2 nM (5HT$_{1A}$ Binding Affinity) IC$_{50}$=14 nM (5HT$_{1D}$ Binding Affinity)

Anal. Calc. for C$_{21}$H$_{22}$ClN$_3$OS•HCl: C,57.80; H, 5.32; N, 9.63. Found: C, 57.64; H, 5.31; N, 9.58.

EXAMPLE 22

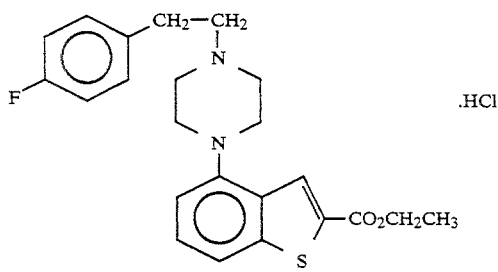

Preparation of ethyl-4-[4-[2-(4-fluorophenyl)ethyl]-1-piperazinyl]-benzo[b]thiophene-2-carboxylate monohydrochloride.

Scheme II, step A; In an analogous manner to example 6, the title compound (0.83 g, recrystallized from 27 mL methanol and 15 mL acetonitrile) as a white solid, mp 265°–270° C. dec., is prepared from ethyl-4-(1-piperazinyl)benzo[b]thiophene-2-carboxylate monohydrochloride (5.5 g, 16.8 mmol, prepared in example 5), 4-fluorophenethyl bromide (3.42 g, 16.8 mmol), sodium bicarbonate (2.83 g, 33.7 mmol) and N,N-dimethylformamide (85 mL); $^1$H NMR (DMSO-$d_6$) δ 11.33 (1H, bs), 8.10 (1H, s), 7.76 (1H, d, J=8.2 Hz), 7.50 (1H, t, J=7.9 Hz), 7.37 (2H, m), 7.20 (2H, m), 7.08 (1H, d, J=7.6 Hz), 4.37 (2H, q, J=7.1 Hz), 3.69 (2H, m), 3.58 (2H, m), 3.37 (6H, bm), 3.15 (2H, m), 1.34 (3H, t, J=7.1 Hz); $^{13}$C NMR (DMSO-$d_6$) δ 162.77, 161.87, 148.21, 142.83, 132.63, 132.00, 130.59, 128.34, 127.83, 118.04, 115.56, 115.27, 113.73, 61.51, 56.16, 51.14, 48.82, 28.46, 14.17; $^{19}$F NMR (DMSO-$d_6$) δ-115.65; IR (KBr) 1716, 1512, 1446, 1282, 1246, 754 cm$^{-1}$; CI/MS (CH$_4$) 413(100%). IC$_{50}$=7.4 nM (5-HT$_{1A}$ Binding Affinity) IC$_{50}$=120 nM (5-HT$_{1D}$ Binding Affinity) pA$_2$=7.53 (0% ) (blocking of 5-HT1-like-mediated contraction in canine saphenous vein )

Anal. Calc. for C$_{23}$H$_{25}$FN$_2$O$_2$S•HCl: C, 61.53; H, 5.85; N, 6.24. Found: C, 61.40; H, 5.82; N, 6.18.

EXAMPLE 23

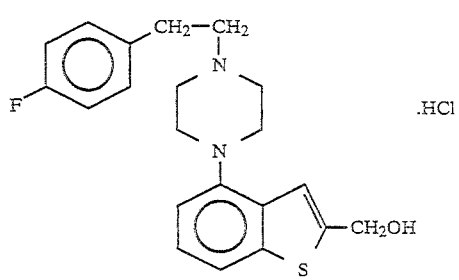

Preparation of 4-[4-[2-(4-fluorophenyl)ethyl]-1-piperazinyl]-benzo[b]-thiophene-2-methanol monohydrochloride.

Scheme I, step; In an analogous manner to example 2, the title compound (1.67 g, recrystallized from 20 mL methanol and 8 mL acetonitrile) as a white solid, mp 238°–240° C. dec., is prepared from ethyl-4-[4-[2-(4-fluorophenyl)ethyl]-1-piperazinyl]-benzo[b]thiophene-2-carboxylate (2.00 g, 4.85 mmol, prepared in example 22) and lithium aluminum hydride (0.37 g, 9.7 mmol); $^1$H NMR (DMSO-$d_6$) δ 11.38 (1H, bs), 7.62 (1H, d, J=7.9 Hz), 7.37–7.17 (2H, s), 3.66 (2H, bm), 3.51 (2H, bm), 3.34 (6H, bm), 3.16 (2H, bm); $^{13}$C NMR (DMSO-$d_6$ ) δ 162.76, 159.54, 146.67, 146.10, 140.28, 133.25, 130.59, 124.61, 117.67, 11 5.55, 115.27, 112.58, 58.92, 56.18, 51.24, 48.36, 28.48; $^{19}$F NMR (DMSO-$d_6$) δ-115.65; IR (KBr) 3313, 1510, 1462, 1219, 958 cm$^{-1}$; CI/MS (CH$_4$) 371 (100%), 353(96%), 261(85%). IC$_{50}$=3 (2) nM (5-HT$_{1A}$ Binding Affinity) IC$_{50}$=3 nM (5-HT$_{1D}$ Binding Affinity)

Anal. Calc. for C$_{21}$H$_{23}$FN$_2$OS·HCl: C, 61.98; H, 5.96; N, 6.88. Found: C, 62.04; H, 6.02; N, 6.86.

Example 24

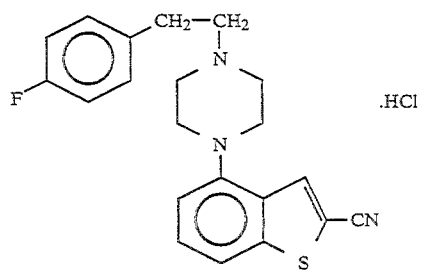

Preparation of 4-[4-[2-(4-fluorophenyl)ethyl]-1-piperazinyl]-benzo[b]-thiophene-2-nitrile monohydrochloride Scheme I, step E; In an analogous manner to example 3, the title compound (0.64 g, recrystallized from 15 mL methanol and 6 mL acetonitrile) as a white solid, mp ca.]b 265° C. dec., is prepared from ethyl-4-[4-[2-(4-fluorophenyl)ethyl]-[b 1-piperazinyl]-benzo[b]thiophene-2-carboxylate (3.00 g, 7.27 mmol, prepared in example 22), trimethyl aluminum (11.0 mL of a 2M solution in toluene, 21.8 mmol), ammonium chloride (1.17 g, 21.8 mmol) and anhydrous dichloromethane (142 mL). The free base is isolated by flash chromatography (ethyl acetate:hexane, 40:60 , TLC Rf=0.4); $^1$H NMR (DMSO-d$_6$) δ11.54 (1H, bs), 8.51 (1H, s), 7.82 (1H, d, J=8.2 Hz), 7.57 (1H, t, J=8.0 Hz), 7.37 (2H, m), 7.21 (2H, m), 7.10 (1H, d, J=7.6 Hz), 3.64 (4H, bm), 3.67 (6H, bm), 3.16 (2H, bm); $^{13}$C NMR (DMSO-d$_6$) δ 162.73, 159.51, 148.03, 142.46, 134.77, 133.24, 131.41, 130.55, 129.20, 117.51, 115.52, 115.23, 114.72, 113.96, 107.09, 56.02, 51.04, 48.45, 28.40; $^{19}$F NMR (DMSO-d6) δ−115.65; IR (KBr) 2551, 1510, 1454, 1446 cm$^1$; CI/MS (CH$_4$) 366(100%).

IC$_{50}$=10 nM (5HT1A Binding Affinity)
IC$_{50}$=21 nM (5HT1D Binding Affinity)
pA2=8.17 ( 9% ) ( blocking of 5-HT1-like-mediated contraction in canine saphenous vein)

Anal. Calc. for C$_{21}$H$_{20}$FN$_3$S.HCl: C, 62.76; H, 5.28; N, 10.45. Found: C, 62.61; H, 5.38; N, 10.39.

Example 25

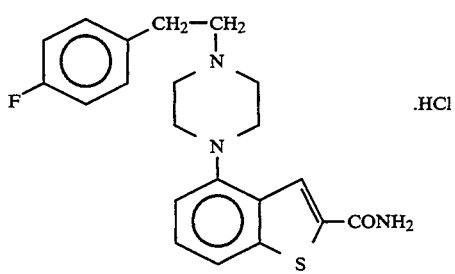

Preparation of 4-[4-[2-(4-fluorophenyl)ethyl]-piperazinyl]-benzo[b]-thiophene-2-carboxamide monohydrochloride Scheme I, step E; The free base of the title compound is isolated during the separation step in example 24 by flash chromatography (ethyl acetate:hexane, 40:60 , TLC R$_f$=0.1) to yield 1.90 g. Dissolve the free base in ethanol (50 mL), treat with 1M hydrochloric acid (5 mL) and concentrate under vacuum. Recrystallize the solid from methanol (35 mL) and acetonitrile (20 mL) to provide the title compound (1.83 g) as a white solid, mp 286°-292° C. dec.; $^1$H NMR (DMSO-d$_6$) δ11.43 (1H, bs), 8.42 (1H, s), 8.20 (1H, s), 7.68 (2H, d, J=8.1 Hz), 7.42-7.34 (3H, m), 7.24-7.18 (2H, m), 6.99 (1H, d, J=7.6 Hz), 3.67 (4H, bm), 3.38 (6H, bm), 3.17 (2H, bm); $^{13}$C NMR (DMSO-d$_6$) δ163.21, 162.77, 159.54, 147.59, 141.99, 139.15, 133.19, 130.59, 126.97, 123.15, 117.53, 115.56, 115.27, 112.79, 55.98, 51.24, 48.33, 28.53; $^{19}$F NMR (DMSO-d$_6$) δ−115.61; IR (KBr) 3331, 1653, 1601, 1510, 1458, 1392, 1222 cm$^{-1}$; CI/MS (CH$_4$) 384(100%).

IC$_{50}$=0.8 (2) nM (5HT$_{1A}$ Binding Affinity)
IC$_{50}$=6 nM (5HT$_{1D}$ Binding Affinity)

Anal. Calc. for C$_{21}$H$_{23}$FN$_3$OS•HCl: C, 60.07; 5.53; 10.00. Found: C, 60.18; H, 5.58; N, 10.01.

Example 26

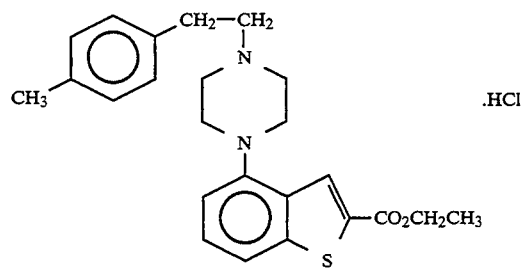

Preparation of ethyl-4-[4-[2-(4-methylphenyl)ethyl]-1-piperazinyl]-benzo[b]thioPhene-2-carboxylate monohydrochloride.

Scheme II, step A; In an analogous manner to example 6, the title compound (0.97 g), mp 267°-270° C. dec., is prepared from ethyl-4-(1-piperazinyl)-benzo[b]thiophene-2-carboxylate monohydrochloride (4.63 g, 14.2 mmol, prepared in example 5 4-methylphenethyl bromide (0.77 g, 3.9 mmol) and sodium bicarbonate (0.65 g, 7.7 mmol). The title compound was recrystallized from acetonitrile:methanol; $^1$H NMR (DMSO-d$_6$) δ10.70(1H, bs), 8.10 (1H, s), 7.76 (1H, d, J=7.9 Hz), 7.50 (1H, t, J=7.9 Hz), 7.19 (4H, m 7.08 (1H, d, J=7.8 Hz), 4.18 (2H, q, J=7.0 Hz), 3.69-3.56 (4H, bm), 3.07 (2H, bm), 2.29 (3H, s), 1.34 (3H, t, J=7. 0 Hz); $^{13}$C NMR (DMSO-d$_6$) δ161.89, 148.20, 142.83, 135.89, 133.80, 132.62, 132.00, 129.20, 128.54, 128.34, 127.84, 118.06, 113.73, 61.50, 56.33, 51.19, 48.92, 28.93, 20.61, 14.18; IR (KBr) 1711, 1282, 1246, 754 cm$^{-1}$; CI/MS (CH$_4$) 409(100%).

Anal. Calc. for C$_{24}$H$_{28}$N$_2$O$_2$S•HCl: C, 64.78; 6.58; 6.29. Found: C, 64.68; H, 6.66; N, 6.20.

Example 27

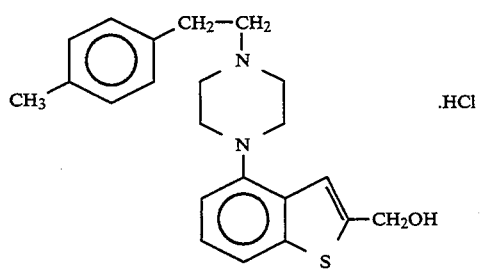

Preparation of 4-[4-[2-(4-methylphenyl)-ethyl]-1-piperazinyl]-benzo[b]thiophene-2-methanol monohydrochloride.

Scheme I, step D; In an analogous manner to example 2, the title compound (1.02 g) as white needles, mp 243°-245° C. dec., is prepared from ethyl-4-[4-[2-(4-methylphenyl)ethyl]-1-piperazinyl]-benzo[b]thiophene-2-carboxylate (1.20 g, 2.80 mmol, prepared in example 26) and lithium aluminum hydride (0.24 g, 6.4 mmol). The title compound is recrystallized from methanol (25 mL) and acetonitrile (5 mL); $^1$H NMR (DMSO-d$_6$) δ10.76 (1H, bs), 7.62 (1H, d, J=7.8 Hz), 7.23 (6H, m), 6.95 (1H, d, J=7.8 Hz), 5.66 1H, bs), 4.76 (2H, d, J=4.5

Hz), 3.69 (2H, m), 3.54 (2H, m), 3.37 (4H, m), 3.21 (2H, m), 3.07 (2H, m), 2.29 (3H, s); $^{13}$C NMR (DMSO-d$_6$) δ146.64, 146.04, 140.23, 135.87, 133.23, 129.18, 128.53, 124.59, 7.71, 117.61, 117.63, 112.58, 58.90, 56.30, 51.26, 48.42, 28.95, 20.59; IR (KBr) 2578, 1462, 959,777 cm$^{-1}$; CI/MS (CH$_4$) 367(100%), 349(83%).

IC$_{50}$=3 nM (5HT$_{1A}$ Binding Affinity)
IC$_{50}$=1 nM (5HT$_{1D}$ Binding Affinity)

Anal. Calc. for C$_{22}$H$_{26}$N$_2$OS•HCl: C, 65.57; H, 6.77; N, 6.95. Found: C, 65.31; H, 6.72; N, 7.03.

Example 28

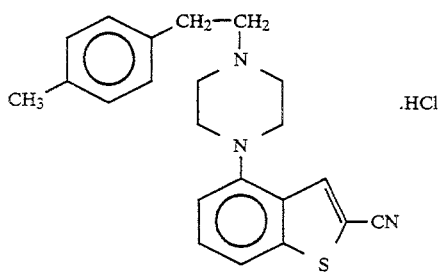

Preparation of 4-[4-[2-(4-methylphenyl)ethyl]-1-piperazinyl]-benzo[b]thiophene-2-nitrile monohydrochloride.

Scheme I, step E; In an analogous manner to example 3, the title compound (0.28 g) as a white solid, mp 260.5°–264.0° C., is prepared from ethyl-4-[4-[2-(4-methylphenyl)ethyl]-1-piperazinyl]-benzo[b]thiophene-2-carboxylate (1.30 g, 3.18 mmol, prepared in example 26), dry ammonium chloride (0.51 g, 9.6 mmol) and trimethyl aluminum (4.8 mL of a 2M solution in toluene, 9.6 mmol). The free base of the title compound is isolated by flash chromatography (ethyl acetate:hexane, 40:60, TLC R$_f$=0.4); $^1$H NMR (DMSO-d$_6$) δ11.48 (1H, bs), 8.51 (1H, s), 7.82 (1H, d, J=8.2 Hz), 7.56 (1H, t, J=7.9 Hz), 7.19 (4H, m), 7.10 (1H, d, J=7.6 Hz), 3.65 (4H, m), 3.45 (6H, m), 3.11 (2H, m), 2.29 (3H, s),; $^{13}$C NMR (DMSO-d$_6$) δ148.03, 142.47, 135.82, 134.78, 133.93, 131.41, 129.17, 128.52, 117.51, 114.72, 113.96, 107.09, 56.20, 51.03, 48.47, 28.83, 20.59; IR (KBr) 2539, 2448, 1564, 1458, 959 cm$^{-1}$; CI/MS (CH$_4$) 362(100%).

IC$_{50}$=4 nM (5HT$_{1A}$ Binding Affinity)
IC$_{50}$=56 nM (5HT$_{1D}$ Binding Affinity)

Anal. Calc. for C$_{22}$H$_{23}$N$_3$S-HCl: C, 66.40; H, 6.09; N, 10.56. Found: C, 66.15; H, 6.06; N, 10.58.

Example 29

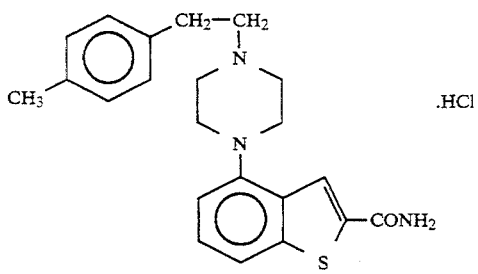

Preparation of 4-[4-[2-(4-methylphenyl)ethyl]-1-perazinyl]-benzo[b]-thiophene-2-carboxamide monohydrochloride.

Scheme I, step E; The free base of the title compound is isolated during the separation step in example 28 by flash chromatography (ethyl acetate:hexane, 40:60 , TLC R$_f$0.4) to yield 0.63 g. Dissolve the free base in dichloromethane (10 mL) and ethanol (50 mL), treat with 1M hydrochloric acid (1.1 mL) and concentrate under vacuum. Triturate the solid with ether to provide the title compound (0.77 g) as a tan solid, mp >260° C. dec.; $^1$H NMR (DMSO-d$_6$) δ11.32 (1H, bs), 8.40 (1H, bs), 8.19 (1H, s), 7.67 (2H, d, J=8.2 Hz), 7.39 (1H, t, J=7.9 Hz), 7.19 (4H, m), 6.99 (1H, d, J=7.5 Hz), 3.67 (4H, m), 3.37 (6H, m), 3.11 (2H, m), 2.29 (3H, s); $^{13}$C NMR (DMSO-d$_6$) δ163.18, 147.56, 141.96, 139.13, 135.85, 133.86, 133.11, 129.19, 128.52, 126.95, 123.10, 117.49, 112.76, 56.17, 51.20, 48.32, 28.93, 20.59; IR (KBr) 3162, 1661, 1605, 1395 cm$^{-1}$; CI/MS (CH$_4$) 380(100%).

IC$_{50}$=1 nM (5HT$_{1A}$ Binding Affinity)
IC$_{50}$=3 nM (5HT$_{1D}$ Binding Affinity)

Anal. Calc. for C$_{22}$H$_{25}$N$_3$OS•HCl•0.32C-H$_3$OH•0.57H$_2$O: C, 61.42; H, 6.56; N, 9.63. Found: C, 61.72; H, 6.53; N, 9.72.

Example 30

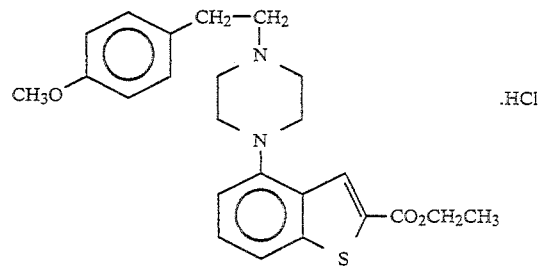

Preparation of ethyl-4-[4-[2-(4-methoxyphenyl)ethyl]-1-pierazinyl]-benzo-[b]thiophene-2-carboxylate monohydrochloride.

Scheme II, step A; In an analogous manner to example 6, the title compound (0.56 g, recrystallized from 10 mL methanol and 50 mL acetonitrile) as a white solid, mp 249°–251° C., is prepared from ethyl-4-(1-piperazinyl)benzo[b]thiophene-2-carboxylate monohydrochloride (5.04 g, 15.4 mmol, prepared in example 5), 4-methoxyphenethyl bromide (3.45 g, 16.2 mmol) and sodium bicarbonate (2.59 g, 30.8 mmol); $^1$H NMR (DMSO-d$_6$) δ11.26 (1H,bs), 8.11 (1H, s), 7.76 (1H, d, J=8.1 Hz), 7.50 (1H, t, J=7.9 Hz), 7.23 (1H, d, J=8.5 Hz), 7.08 (1H, d, J=7.6 Hz), 6.93 (1H, d, J=8.7 Hz), 4.37 (2H, q, J=7.1 Hz), 3.75 (3H, s), 3.62 (4H, m), 3.36 (6H, m), 3.09 (2H, m), 1.35 (3H, t, J=7.1 Hz); $^{13}$C NMR (DMSO-d$_6$): 161.86, 158.11, 148.24, 142.80, 132.59, 131.95, 129.67, 128.76, 128.32, 127.80, 117.96, 114.06, 113.66, 61.47, 56.48, 55.02, 51. 05, 48.79, 28.41, 14.14; IR (KBr) 1709, 1515, 1449, 1284, 1246 cm$^{-1}$; CI/MS (CH$_4$) 425(100%).

IC$_{50}$=74 nM (5HT$_{1A}$ Binding Affinity)
IC$_{50}$=73 nM (5HT$_{1D}$ Binding Affinity)

Anal. Calc. for C$_{24}$H$_{28}$N$_2$O$_3$S-HCl•0.25 H$_2$O: C, 61.92; H, 6.40; N, 6.02. Found: C, 62.07; H, 6.37; N, 6.15.

Example 31

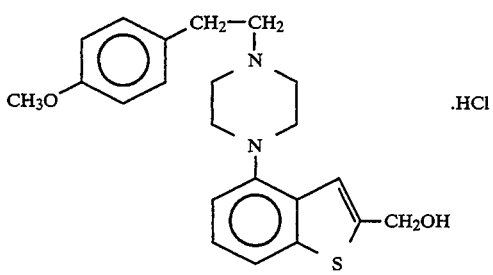

Preparation of 4-[4-[2-(4-methoxyphenyl)ethyl]-1-piperazinyl]-benzo[b]thiophene-2-methanol monohydrochloride.

Scheme I, step D; In an analogous manner to example 2, the title compound (0.69 g, recrystallized from 25 mL methanol and 5 mL acetonitrile) as faintly blue-green crystals, mp 236.5°–238° C., is prepared from ethyl-4-[4-[2-(4methoxyphenyl)ethyl]-1-piperazinyl]-benzo[b]thiophene-2-carboxylate (1.30 g, 3.06 mmol, prepared in example 30) and lithium aluminum hydride (0.23 g, 6.12 mmol); $^1$H NMR (DMSO-d$_6$) δ11.01 (1H, bs), 7.62 (1H, d, J=7.9 Hz), 7.27 (4H, m), 6.90 (3H, m), 5.67 (1H, m) 4.76 (2H, s), 3.75 (3H, s), 3.68 (2H, m), 3.58 (2H, m), 3.31 (6H, m), 3.07 (2H, m); $^{13}$C NMR (DMSO-d$_6$) δ158.14, 146.66, 146.09, 140.26, 133.24, 129.71, 124.60, 117.12, 117.61, 114.09, 112.58, 58.91, 56.49, 55.06, 51.28, 48.38, 28.49; IR (KBr) 1514, 1463, 1258, 1250, 1033 cm$^{-1}$; CI/MS (CH$_4$) 383(95%), 365(100%).

IC$_{50}$=1 nM (5HT$_{1A}$ Binding Affinity)
IC$_{50}$=2 nM (5HT$_{1D}$ Binding Affinity)

Anal. Calc. for C$_{22}$H$_{26}$N$_2$O$_2$S•HCl: C, 63.07; H, 6.51; N, 6.68. Found: C, 62.84; H, 6.52; N, 6.79.

Example 32

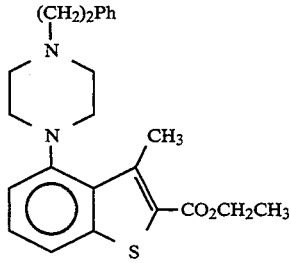

Preparation of ethyl-4-[4-(2-phenylethyl)-1-piperazinyl]-benzo[b]thiophene-3-methyl-2-carboxylate Scheme I, step A; In an analogous manner to example 1, step A, 4-(2-phenylethyl)-1-(3-fluoro-2-acetyl-1-phenyl)piperazine (4.60 g) as yellow crystals, mp 89°–90° C., is prepared from 2,6-difluoroacetophenone (6.91 g, 32.0 mmol), 1-benzylpiperazine (6.63 mL, 38.4 mmol), potassium carbonate (5.3 g, 38.4 mmol) and N,N-dimethylformamide (9 mL); $^1$H NMR (CDCl$_3$) δ7.34–7.19 (6H, m), 6.87 (1H, d, J=8.2 Hz), 6.78 (1H, t, J=8.0 Hz), 3.04 (4H, m), 2.86–2.80 (2H, m), 2.68–2.62 (6H, m), 2.58 (3H, s); $^{13}$C NMR (CDCl$_3$) δ201.31, 160.43, 157.14, 151.67, 151.58, 140.12, 131.11, 130.97, 128.66, 128.40, 126.10, 114.97, 114.92, 110.63, 110.33, 60.32, 53.36, 52.89, 33.59, 31.53; $^{19}$F NMR (CDCl$_3$) −117.139 (bt, J=37 Hz); IR (KBr) 2812, 1690, 1607, 1455, 1257, 1133, 992,795, 758, 708 cm$^{-1}$; CI/MS (CH$_4$) 327(100%), 235(67%)

Anal. Calc. for C$_{20}$H$_{23}$FN$_2$O: C, 73.59; H, 7.10; N, 8.58. Found: C, 73.46; H, 7.19; N, 8.61.

Scheme I, step B: In an analogous manner to example 1, step B, the title compound (1.01 g) as a yellow solid, mp 92.5°–94.5° C., is prepared from 4-(2-phenylethyl)-1-(3-fluoro-2-acetyl-1-phenyl)piperazine (4.83 g, 14.8 mmol), dry N,N-dimethylformamide (50 mL), ethyl 2-mercaptoacetate (2.76 mL, 23.0 mmol) and sodium hydride (0.92 g of a 60% oil dispersion, 23 mmol); $^1$H NMR (CDCl$_3$) δ7.52 (1H, dd, J=1.0, 7.9 Hz), 7.38–7.19 (6H), 7.08 (1H, dd, J=0.7, 7.7 Hz), 4.38 (2H, q, J=7.1 Hz), 3.15 (2H, m), 3.12 (3H, s), 3.02 (4H, m), 2.51 (2H, m), 1.41 (3H, t, J=7.1 Hz); $^{13}$C NMR (CDCl$_3$) δ163.59, 152.29, 142.66, 142.61, 140.25, 134.09, 128.78, 128.76, 128.71, 128.42, 127.43, 126.09, 125.94, 118.36, 115.07, 60.97, 60.53, 53.69, 53.11, 33.71, 15.99, 14.34; CI/MS (CH$_4$) 409(100%), 317(62%).

Anal. Calc. for C$_{24}$H$_{28}$N$_2$O$_2$S$_2$: C, 70.56; H, 6.91; N, 6.86. Found: C, 70.75; H, 7.18; N, 6.56.

Example 33

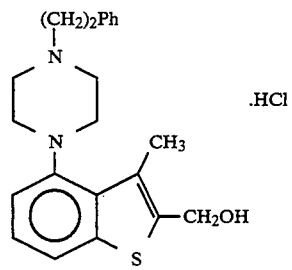

Preparation of 4-[4-(2,phenylethyl)-1-piperazinyl]-benzo[b]-thiophene-3-methyl-2-methanol monhydrochloride 0.5 hydrate Scheme I, step D; In an analogous manner to example 2, the title compound (0.75 g) as a white solid, mp 254°–256° C., is prepared from ethyl-4-[4-(2-phenylethyl)-1-piperazinyl]-benzo[b]thiophene-3-methyl-2-carboxylate (950 mg, 2.33 mmol, prepared in example 32) and lithium aluminum hydride (177 mg, 4.6 mmol); $^1$H NMR (DMSO-d$_6$) δ11.42 (1H, bs), 7.67 (1H, d, J=7.8 Hz), 7.39–7.23 (6H), 7.09 (1H, d, J=7.5 Hz), 5.62 (1H, bs), 4.73 (2H, s), 3.65 (2H, m), 3.43–3.20 (10H), 3.18–3.12 (2H, m), 2.61 (3H, s); $^{13}$C NMR (DMSO-d$_6$) δ148.03, 140.85, 139.89, 137.14, 134.30, 128.62, 126.74, 126.12, 124.04, 119.27, 115.03, 57.13, 56.35, 51.02, 29.29, 13.72; IR (KBr) 3376, 1456, 1153, 957, 746, 702 cm$^{-1}$; CI/MS (CH$_4$) 367(85%), 349(100%), 275(60%). IC$_{50}$=9 nM (5-HT$_{1A}$ Binding Affinity) IC$_{50}$=31 nM (5-HT$_{1D}$ Binding Affinity)

Anal. Calc. for C$_{22}$H$_{26}$N$_2$OS•HCl•0.5H$_2$O: C, 64.15; H, 6.87; N, 6.80. Found: C, 63.81; H, 6.85; N, 6.68.

EXAMPLE 34

Ethyl 4-[(4-propyl)-1-piperazinyl]benzo[b]thiophene-2-carboxylate hydrochloride

To a stirred solution of ethyl 4-(1-piperazinyl)benzo[b]thiophene-2-carboxylate hydrochloride (3.27 g, 10.0 mmol) in dry dimethylformamide under a nitrogen atmosphere is added sodium bicarbonate (1.68 g, 20.0 mmol) and 1-bromopropane (1.36 mL, 15 mmol). After 24 h at 20° C., the reaction is heated at 60° C. for 4 h, then cooled, treated with water (75 mL), and extracted with ether (2×100 mL). The combined extracts are washed with water (50 mL), then brine (50 mL), dried with magnesium sulfate/sodium sulfate, and concentrated in vacuo. Chromatography (ethyl acetate) gives a component with $R_f=0.2$ as a yellow-orange oil solidifying on standing (2.85 g). $^1$H NMR (CDCl$_3$): 8.12 (1H, d, J=0.7 Hz), 7.48 (1H, dd, J=0.8, 8.1 Hz), 7.36 (1H, app. t, J=7.9 Hz), 6.89 (1H, dd, J=0.7, 7.5 Hz), 4.41 (2H, q, J=7.1 Hz), 3.20 (4H, m), 2.71 (4H, m), 2.45–2.40 (2H, m), 1.62–1.54 (2H, m), 1.42 (3H, t, J=7.1 Hz), 0.95 (3H, t, J=7.1 Hz) ppm. $^{13}$C NMR (CDCl$_3$): 162.91, 150.20, 143.75, 133.33, 131.87, 128.61, 127.87, 116.79, 112.64, 61.48, 60.71, 53.47, 52.37, 20.05, 14.33, 11.97 ppm. IR(KBr): 2959, 1713, 1252, 1235, 1180, 1155, 1070, 754 cm$^{-1}$. CIMS (methane): 333 (100%), 332 (71%).

Anal. Calc. for C$_{18}$H$_{24}$N$_2$O$_2$S: C, 65.03: H, 7.28; N, 8.43. Found: C, 65.28; H, 7.23; N, 8.56.

Melting point: 57°–61° C.

A portion (0.50 g, 1.5 mmol) is dissolved in ethanol (20 mL) and treated with 1.0M aqueous hydrochloric acid (0.55 mL) and concentrated in vacuo to a light yellow solid. This is triturated with acetonitrile and dried in vacuo to give the title compound (0.43 g). $^1$H NMR (d$_6$-DMSO): 11.14 (1H, bs), 8.10 (1H, s), 7.76 (1H, d, J=8.1 Hz), 7.50 (1H, app. t, J=8.0 Hz), 7.06 (1H, d, J=7.5 Hz), 4.37 (2H, q, J=7.0 Hz), 3.61–3.51 (4H), 3.34 (8H, m), 3.10 (2H, m), 1.79 (2H, m), 1.35 (3H, t, J=7.1 Hz), 0.95 (3H, t, J=7.3 Hz) ppm. $^{13}$C NMR (d$_6$-DMSO): 161.88, 148.27, 142.81, 132.60, 131.95, 128.3 4, 127.85, 117.97, 113.63, 61.50, 57.01, 50.94, 48.71, 16.58 , 14.17, 10.97 ppm. IR (KBr): 3428, 2969, 2582, 2515, 1717, 1462, 1251. 754 cm$^{-1}$. CIMS (methane): 333 (100%), 332 (71%). IC$_{50}$=104 nM (5-HT$_{1A}$ Binding Affinity) IC$_{50}$=416 nM (5-HT$_{1D}$ Binding Affinity) pA$_2$=6.78 (12%) (blocking of 5-HT$_1$-like-mediated contraction in canine saphenous vein)

Anal. Calc. for C$_{18}$H$_{24}$N$_2$O$_2$S•HCl: C, 58.60; H, 6.83; N, 7.59. Found: C, 58.56; H, 6.94; N, 7.47.

Melting point: 242°–244° C. (decomposes).

EXAMPLE 35

4-[(4-propyl)-1-piperazinyl]benzo[b]thiophene-2-methanol hydrochloride

To a magnetically stirred solution of ethyl 4-[(4-propyl)-1-piperazinyl]benzo[b]thiophene-2-carboxylate (1.10 g, 3.30 mmol, Example 34) in anhydrous tetrahydrofuran (33 mL) under nitrogen is added lithium aluminum hydride (0.150 g, 3.96 mmol) After 3 h at 20° C. the reaction is treated carefully and sequentially with water (0.15 mL), 10% aqueous sodium hydroxide (0.22 mL), and water (0.45 mL). After filtering through coarse filter paper, the filtrate is treated with water (50 mL), and extracted with a 20:80 2-propanol:dichloromethane mixture (3×50 mL). The extracts are dried (sodium sulfate) and concentrated in vacuo to a wet solid which was triturated with acetonitrile to give an off-white solid (0.72 g). This solid was dissolved in ethanol (20 mL), treated with 1.0M aqueous hydrochloric acid, concentrated in vacuo, reconcentrated from ethanol (20 mL), then 4:1 acetonitrile:ethanol (20 mL) and the resulting solid triturated with acetonitrile to give the title compound as a white solid (0.73 g). $^1$H NMR (d$_6$-DMSO): 11.12 (1H, bs), 7.62 (1H, d, J=8.0 Hz), 7.31 (1H, s), 7.27 (1H, d, J=7.8 Hz), 6.93 (1H, d, J=7.6 Hz), 5.70 (1H, bs), 4.75 (2H, s), 3.59 (2H, bd, J=8.6 Hz), 3.50 (2H, bd, J=8.6 Hz), 3.27 (4H, m), 3.11 (2H, m), 1.79 (2H, m), 0.96 (3H, t, J=7.2 Hz) ppm. $^{13}$C NMR (d$_6$-DMSO): 146.63, 146.10, 140.27, 133.23, 124.61, 117.77, 117.60, 112.52, 58.84, 56.94, 51.08, 48.27, 16.60, 10.98 ppm. IR (KBr): 3250, 1570, 1462, 1418, 1012, 964, 777 cm$^{-1}$. CIMS (methane): 291 (83%), 290 (100%), 273 (100%), 261 (60%). IC$_{50}$=34 nM (5-HT$_{1A}$ Binding Affinity) IC$_{50}$=66 nM (5-HT$_{1D}$ Binding Affinity)

Anal. Calc. for C$_{16}$H$_{22}$N$_2$OS•HCl: C, 58.79; H, 7.09; N, 8.57. Found: C, 58.85; H, 7.14; N, 8.56. Melting point: 221°–223° C.

EXAMPLE 36

4-[4-(2-phenylethyl)-1-piperazinyl]-benzo[b]thiophene-2-(N-ethyl)carboxamide hydrochloride The title compound was made following the procedure and scale as in Example 10 except using ethylamine hydrochloride as the amine. Chromatography using ethyl acetate gave a component with an R$_f$=0.4 (streaking) which was isolated as a slightly yellow solid (1.17 g). This was converted to the hydrochloride salt by dissolving in ethanol (50 mL), treating with 1.0M aqueous hydrochloric acid, concentrating in vacuo, then reconcentrating from acetonitrile (3×50 mL) which caused the title product to precipitate. The product was vacuum dried a 60° C. for 8 h (1.21 g). $^1$H NMR (d$_6$-DMSO): 11.32 (1H, bs), 9.03 (1H, m), 8.19 (1H, s), 7.68 (1H, d, J=8.1 Hz), 7.42–7.26 (6H), 7.00 (1H, d, J=7.6 Hz), 3.73 (2H, m), 3.63 (2H, bd), 3.47–3.31(9H), 3.17 (2H, m), 1.17 (3H, t, J=7.2 Hz)ppm. $^{13}$C NMR (d$_6$-DMSO): 161.13, 147 .54, 141.61, 139.18, 137.02, 133.16, 128.67, 126.85, 126.82, 122.15, 117.56, 112.92, 56.08, 51.27, 48.39, 34.01, 2 9.38, 14.92 ppm. IR (KBr): 3432, 3271, 2378, 1647, 1458 , 1439, 1283, 959, 752 cm$^{-1}$. CIMS (methane): 394 (100%), 302 (45%).

Anal. Calc. for C$_{23}$H$_{27}$N$_3$OS•HCl: C, 64.25; H, 6.56; N, 9.77. Found: C, 64.05, H, 6.70, N, 9.63.

EXAMPLE 37

4-[4-(2-phenylethyl)-1-piperazinyl]-benzo[b]thiophene-2-(O-methyl)-methanol hydrochloride To a stirred suspension of 4-[4-(2-phenylethyl)-1-piperazinyl]-benzo[b]thiophene-2-methanol (725 mg, 2.06 mmol) in anhydrous dimethylformamide (10 mL) under nitrogen is added sodium hydride (60% in oil dispersion, unwashed, 124 mg, 3.1 mmol). After 10 minutes, methyl iodide (0.145 mL, 2.3 mmol) is added. Thirty minutes later the reaction is quenched by addition to water (80 mL) and extracted with ether (1.0 mL). The extract is washed with water (50 mL), then brine (50 mL), then dried with magnesium sulfate/sodium sulfate and concentrating in vacuo to a solid. Chromatography (50:50 ethyl acetate:hexane) gives a component with an R$_f$=0.5 isolated as a somewhat glassy solid (630 mg). This is converted into the hydrochloride salt by concentrating in vacuo a solution of 600 mg of this product in ethanol (20 mL) and 1.0M aqueous hydrochloric acid (1.9 mL). Recrystallization from acetonitrile gives the title compound as a light yellow solid (455 mg). $^1$H NMR (d$_6$-DMSO): 11.44 (1H, bs), 7.62 (1H, d, J=8.1 Hz), 7.43 (1H, d, J=0.6 Hz), 7.40–7.28 (7H), 6.97 (1H, d, J=7.2 Hz), 4.71 (2H, d, J=0.6 Hz), 3.70 (2H, bd), 3.55 (2H, bd), 3.43–3.27 (9H), 3.17 (2H, m) ppm. $^{13}$C NMR (d$_6$-DMSO): 146.35, 141.33, 140.74, 137.06, 132.93, 128.67, 128.65, 126.80, 125.14, 120.49, 117.60, 112.74, 68.85, 57.41, 56.12, 51.13, 48.36, 29.28 ppm. IR (KBr): 3437, 2434, 1464, 1370, 1132, 1092, 963. 702 cm$^{-1}$. CIMS (methane): 367 (100%), 366 (74%) 335 (86%), 275 (86%). IC$_{50}$=5nM (5-HT$_{1A}$ Binding Affinity) IC$_{50}$=9nM (5-HT$_{1D}$ Binding Affinity) pA$_2$=8.03 (0%) (blocking of 5-HT$_1$-like-mediated contraction in canine saphenous vein)

Anal. Calc. for C$_{22}$H$_{26}$N$_2$OS•HCl: C, 65.57; H, 6.75; N, 6.95. Found: C, 65.84; H, 6.73; N, 7.07.

Melting point: 235°–237° C.

EXAMPLE 38

4-[4-propyl-1-piperazinyl]-benzo[b]thiophene-2-[N-methyl]carboxamide hydrochloride 0.4 hydrate The title compound is made following the procedure and scale (3.3 mmol of ester) as in Example 10, except using methylamine hydrochloride as the amine and ethyl 4-[4-propyl-1-piperazinyl]benzo[b]thiophene-2-carboxylate as the starting ester. The extractive workup is performed using 20:80 2-propanol:dichloromethane. Chromatography using 20:80 ethanol:ethyl acetate gives a component with an R$_f$=0.2 (streaking) which is isolated as a slightly yellow solid (0.96 g). This is converted to the hydrochloride salt by dissolving in ethanol (50 mL), treating with 1.1 equivalents of 1.0M aqueous hydrochloric acid, concentrating in vacuo, then reconcentrating from acetonitrile (3×50 mL). Recrystallization from ethanol/acetonitrile with acetonitrile trituration and vacuum drying at 70° C. for 8 h affords the title product as white crystals (1.03 g). $^1$H NMR (d$_6$-DMSO): 10.96 (1H, b), 8.98 (1H, m), 8.19 (1H, m), 7.67 (1H, d, J=8.0 Hz), 7.39 (1H, d, J=7.8 Hz), 6.98 (1H, d, J=7.7 Hz), 3.61 (4H, appt. J=12 Hz), 3.37–3.24 (4H), 3.14 (2H, m), 2.83 (3H, m), 1.80 (2H, m), 0.96 (3H, t, J=7.4 Hz) ppm. $^{13}$C NMR (d$_6$-DMSO): 161.77, 161.69, 147.50, 141.55, 138.87, 138.81, 133.09, 126.85, 122.27, 117.50, 112.80, 56.92, 51.20, 26.20, 16.67, 10.97 ppm. IR (KBr): 3441, 3270, 1640, 1626, 1551, 972 cm$^{-1}$. CIMS (methane): 318 (100%), 317 (40%).

Anal. Calc. for C$_{17}$H$_{23}$N$_3$OS•HCl 0.4 H$_2$O: C, 56.54; H, 6.92; N, 11.64. Found: C, 56.71; H, 7.05; N, 11.55.

EXAMPLE 39

4-[4-methyl-1-piperazinyl]-benzo[b]thiophene-2-methanol hydrochloride

A stirred solution of ethyl 4-[4-methyl-1-piperazinyl]-benzo[b]thiophene-2-carboxylate (1.04 g, 3.20 mmol) in dry tetrahydrofuran (32 mL) under nitrogen is treated with lithium aluminum hydride (242 mg, 6.4 mmol). After 1 h, water (30 mL), sodium chloride and 20:80 2-propanol:dichloromethane (60 mL) are added and the reaction stirred 1 h. The reaction is extracted with 2 more portions of 2-propanol:dichloromethane, dried with sodium sulfate, and concentrated. Chromatography with 0:50:50, then 5:50:50 diethylamine:ethanol:ethyl acetate gives an oil solidifying overnight (0.75 g). Reconcentration from ethanol several times followed by dissolving in ethanol (30 mL), treating with 1.0M hydrochloric acid (3 mL), and concentrating in vacuo gives the title compound. Recrystallization from acetonitrile:methanol gives a white solid (0.66 g). $^1$H NMR (d$_6$-DMSO): 11.19 (1H, bs), 7.62 (1H, d, J=8.0 Hz), 7.31 (1H, d, J=0.9 Hz), 7.26 (1H, t, J=7.9 Hz), 6.94 (1H, dd, J=0.7, 7.6 Hz), 5.70 (1H, bm), 4.75 (3H, s), 3.54–3.15 (8H), 2.85 (3H, s) ppm. $^{13}$C NMR (d$_6$-DMSO): 146.60, 146.08, 140.25, 133.2 5, 124.59, 117.75, 117.59, 112.60, 58.85, 52.69, 48.37, 42.02 ppm. IR (KBr): 3327, 2444, 1570, 1456, 1248, 1014, 781 cm$^{-1}$. CIMS (methane): 263 (62%), 262 (70%), 245,(100%). IC$_{50}$=16 nM (5-HT$_{1D}$ Binding Affinity)

Anal. Calc. for C$_{14}$H$_{18}$N$_2$OS•HCl: C, 56.27, H, 6.41; N, 9.37. Found: C, 56.15; H, 6.43; N, 9.34.

Melting point: 204°–205° C.

EXAMPLE 40

4-[4-(2-phenylethyl)-1-piperazinyl]-benzo[b]thiophene-2-(N-methyl-N-methoxy)-carboxamide hydrochloride The title compound is made following the procedure and scale as in Example 10 except using 5 equivalents of N,O-dimethylhydroxyl amine hydrochloride as the amine with 5 equivalents of trimethylaluminum and using tetrahydrofuran as the solvent. The reaction is stirred for 22 h at ca. 20° C. Chromatography using 50:50, then 0:100 hexane ethyl acetate gives a component with a R$_f$=0.4 (ethyl acetate) which was isolated as a slightly yellow solid (0.88 g). $^1$H NMR (CDCl$_3$): 8.33 (1H, d, J=0.7 Hz), 7.51 (1H, d, J=8.1 Hz), 7.37 (1H, t, J=7.8 Hz), 7.35–7.20 (5H), 6.91 (1H, dd, J=0.7, 7.7 Hz), 3.84 (3H, s), 3.44 (3H, s), 3.26 (4H, m) 2.92–2.71(8H) ppm. $^{13}$C NMR (CDCl$_3$): 162.61, 149.83, 144.30, 132.35, 131.07, 129.70, 128.68, 128.38, 127.52, 126.04, 116.34, 112.32, 61.85, 60.48, 53.43, 52.27, 33.60, 33.13 ppm. IR (KBr): 3009, 2940, 2824, 1620, 1454, 1383 cm$^{-1}$. CIMS (methane): 410 (100%), 318 (48%).

Anal. Calc. for C$_{23}$H$_{27}$N$_3$O$_2$S. C, 67.45; H, 6.65; N, 10.26. Found: C, 67.05; H, 6.62; N, 10.12.

Melting Point: 130°–131° C.

This was converted to the hydrochloride salt by dissolving in ethanol, treating with 1.0M aqueous hydrochloric acid, concentrating in vacuo, then reconcentrating from hot ethanol by slow concentration under nitrogen stream to give a white solid (0.83 g). $^1$H NMR (d$_6$-DMSO): 11.45 (1H, bs), 8.13 (1H, bs), 7.73 (1H, d, J=8.1 Hz), 7.46 (1H, t, J=7.9 Hz), 7.41–7.26 (5H), 7.05 (1H, d, J=7.5 Hz), 3.84 (3H, s), 3.7 2 (2H, bd, J=11.1 Hz), 3.59 (2H, bd, J=11.2 Hz) , 3.47–3. 28 (9H), 3.17 (2H, m) ppm. $^{13}$C NMR (d$_6$-DMSO): 161.09, 147. 81, 143.24, 137.10, 132.24, 131.75, 128.66, 127.91, 127.75, 12 6.79, 117.49, 113.18, 61.81, 56.23, 51.06, 48.77, 32.8 5, 29.27 ppm. IR (KBr): 3437, 2934, 2425, 1632, 1458, 1379, 966 cm$^{-1}$. CIMS (methane): 410 (100%), 380 (40%) 18 (40%). IC$_{50}$=2.4 nM (5-HT$_{1A}$ Binding Affinity) IC$_{50}$=16 nM (5-HT$_{1D}$ Binding Affinity) pA$_2$=8.50 (3%) (blocking of 5-HT$_1$-like-mediated contraction in canine saphenous vein)

Anal. Calc. for C$_{23}$H$_{27}$N$_3$O$_2$S•HCl: C, 61.94; H, 6.33; N, 9.42. Found: C, 62.03; H, 6.41; N, 9.43.

Melting point: 250°–252° C. (dec).

EXAMPLE 41

2-[4-[4-(2-phenylethyl)-1-piperazinyl]benzo[b]thiophene-2-]-(2-propanol) hydrochloride hemihydrate To a stirred solution of ethyl 4-[4-(2-phenylethyl)-1-piperazinyl]benzo[b]thiophene-2-carboxylate (1.24 g, 3.14 mmol) in anhydrous tetrahydrofuran (15 mL) at 0° C. under nitrogen is added 3M methyl magnesium chloride in tetrahydrofuran (2.2 mL). After 5 minutes, the reaction is allowed to warm to ca. 20° C. After 6 h, water (100 mL) is added and the reaction is extracted with dichloromethane (2×100 mL). The extracts are dried with sodium sulfate, concentrated in vacuo to an oil, and chromatographed with 50:50 ethyl acetate:hexanes. The hydrochloride salt is formed by dissolving in acetonitrile (50 mL) and treating with 1.1 equivalents of 1.0M hydrochloric acid, causing the hydrochloride to precipitate as a white solid (0.865 g). $^1$H NMR (d$_6$-DMSO): 11.37 (1H, bs), 7.58 (1H, d, J=8.0 Hz), 7.40–7.19 (7H), 6.95 (1H, d, J=7.7 Hz), 5.65 (1H, s), 3.69 (2H, bm), 3.54–3.12 (10H), 1.59 (s, 6H) ppm. $^{13}$C NMR (d$_6$-DMSO): 156.56, 146.01, 139.69, 137.11, 133.63, 128.68, 128.65, 126.77, 124.33, 117.49, 115.13, 112.50, 70.46, 56.22, 51.22, 48.41, 39.51, 32.17 ppm. IR (KBr): 3389, 2972, 2558, 1570, 1456, 959 cm$^{-1}$. CIMS (methane): 381 (100%), 363 (100%), 289 (75%). IC$_{50}$=4 nM (5-HT$_{1A}$ Binding Affinity) IC$_{50}$=16 nM (5-HT$_{1D}$ Binding Affinity) pA$_2$=7.44 (16%) (blocking of 5-HT1-like-mediated contraction in canine saphenous vein)

Anal. Calc. for C$_{23}$H$_{28}$N$_2$OS•HCl•0.5H$_2$O: C, 64.72; H, 7.08; N, 6.56. Found: C, 64.84; H, 7.05; N, 6.50.

Melting point: 193°–195° C.

EXAMPLE 42

1-[4-(4-phenethyl-piperazin-1-yl)-benzo[b]thiophen-2-yl]ethanone hydrochloride

To a solution of 4-[4-(2-phenylethyl)-1-piperazinyl]-benzo[b]thiophene-2-(N-methyl-N-methoxy)carboxamide (Example 40, 2.15 g, 5.25 mmol) in dry tetrahydrofuran (25 mL) at 0° C. under nitrogen is added 3.0M methyl magnesium chloride in tetrahydrofuran (3.5 mL). A tan precipitate is formed. After 0.5 h, the cold bath is removed. After 3 h total time, the reaction is acidified with 1.0M aqueous hydrochloric acid, stirred 0.33 h, made basic with saturated aqueous sodium bicarbonate, and extracted with dichloromethane (2×100 mL). After drying with sodium sulfate and concentrating in vacuo, the yellow product is chromatographed with 50:50, then 100:0 ethyl acetate:hexanes isolating the component with an R$_f$ of 0.3 in the first system. This yellow solid is the free amine of the title compound (1.90 g). CIMS (methane): 365 (100%), 273 (43%).

Anal. Calc. for C$_{22}$H$_{24}$N$_2$OS: C, 72.49, H, 6.64: N, 7.69. Found: C, 72.22; H, 6.70, N, 7.58.

Melting point: 131°–132° C.

A 0.94 g portion of the above is dissolved in ethanol (50 mL), treated with 1.0M hydrochloric acid (2.3 mL), concentrated in vacuo, reconcentrated from acetonitrile (2×50 mL), and vacuum dried at 70° C. for 9 h to give the title compound (0.98 g). $^1$H NMR (d$_6$-DMSO): 11.19 (1H, bs), 8.22 (1H, s), 7.74 (1H, d, J=8.1 Hz), 7.49 (1H, t, J=8.0 Hz), 7.41–7.26 (5H), 7.07 (1H, d, J=7.5 Hz), 3.74–3.62 (4H), 3.51–3.27 (6H), 3.17 (2H, m), 2.71 (3H, s) ppm. $^{13}$C NMR (d$_6$-DMSO): 192.45, 148.69, 143.19, 142.49, 137.01, 133.12, 128.69, 128.34, 126.83, 117.99, 113.53, 56.14, 51.12, 48.67, 29.34, 26.66 ppm. IR (KBr): 3435, 2922, 2668, 1460, 1277, 962 cm$^{-1}$. CIMS (methane): 365 (100%), 273 (32%). IC$_{50}$=22 nM (5-HT$_{1D}$ Binding Affinity) pA$_2$=7.87 (1%) (blocking of 5-HT$_1$-like-mediated contraction in canine saphenous vein)

Anal. Calc. for C$_{22}$H$_{24}$N$_2$OS•HCl: C, 65.90; H, 6.28; N, 6.99. Found: C, 65.79, H, 6.31; N, 7.34.

Melting point: 269°–272° C. (dec).

EXAMPLE 43

1-[4-(4-phenethyl-piperazin-1-yl)-benzo[b]thiophen-2-yl]ethanol hydrochloride

To partially dissolved 1-[4-(4-phenethyl-piperazin-1-yl)benzo[b]thiophen-2-yl]-ethanone hydrochloride (0.92 g, 2.5 mmol, product from Example 42) in methanol (70 mL) is added sodium borohydride (0.19 g, 5.0 mmol). After 0.33 h, the reaction is clear and homogeneous. The reaction is worked up after 2 h by pouring into water (10 mL), extracting with dichloromethane (3×75 mL), and concentrating the sodium sulfate dried extracts in vacuo. The product (R$_f$ of 0.3 in ethyl acetate) is dissolved in acetonitrile (50 mL), treated with 1.0M hydrochloric acid (2.5 mL), concentrated in vacuo, then reconcentrated from acetonitrile:methanol to give a white solid. After vacuum drying for 9 h at 70° C., the title compound is isolated as a white solid (0.865 g). $^1$H NMR (d$_6$-DMSO): 11.48 (1H, bs), 7.61 (1H, d, J=8.0 Hz), 7.40–7.23 (7H), 6.95 (1H, d, J=7.6 Hz), 5.76 (1H, bs), 5.07 (1H, q, J=6.2 Hz), 3.69 (2H, bd, J=10.6 Hz), 3.53 (2H, m), 3.45–3.25(6H), 3.17 (2H, m), 1.50 (3H, d, J=6.4 Hz) ppm. $^{13}$C NMR (d$_6$-DMSO): 152.13, 146.05, 139.74, 137.10, 133.35, 128.67, 126.79, 124.47, 117.62, 116.20, 112.54, 64.86, 56.19, 51.18, 48.45, 48.24, 29.29, 25.68 ppm. IR (KBr): 3351, 2575, 2554, 2446, 1570 cm$^{-1}$. CIMS (methane): 367 (92%), 349 (100%), 275 (82%).

IC$_{50}$=0.5 nM (5-HT$_{1A}$ Binding Affinity)
IC$_{50}$=3nM (5-HT1D Binding Affinity)

Anal. Calc. for C$_{22}$H$_{26}$N$_2$OS•HCl: C, 65.57; H, 6.75; N, 6.95. Found: C, 65.33; H, 6.81, N, 6.87. Melting point: 165°–167° C.

EXAMPLE 44

4-[4-phenylmethyl-1-piperazinyl]-benzo[b]thiophene-2-methoxymethyl hydrochloride To a solution of 4-[4-phenylmethyl-1-piperazinyl]-benzo[b]thiophene-2-methanol (2.33 g, 6.88 mmol) (from Example 2) in dry dimethylsulfoxide (30 mL) under nitrogen is added 60% sodium hydride in an oil dispersion (0.413 g, 10.3 mmol). After 0.16 h, methyl iodide (0.57 mL, 8.3 mmol) is added. After 1 h. water (100 mL) is added and the reaction is extracted with ether (2×100 mL). The ether extracts are combined, washed with water, then brine (50 mL each), then dried with magnesium sulfate, and concentrated in vacuo, to a viscous oil. Chromatography (50:50 ethyl acetate:hexanes) gave a component with an R$_f$ of 0.6 as an oil (1.84 g). The oil was dissolved in acetonitrile (50mL), treated with 1.0M hydrochloric acid (2.5 mL) and concentrated in vacuo. then reconcentrated from acetonitrile (50 mL) to give the title compound as an off-white solid (0.94 g). $^1$H NMR (d$_6$-DMSO): 11.57 (1H, bs), 7.74–7.71 (2H), 7.63 (1H, d, J=8.2 Hz), 7.51–7.46 (3H), 7.42 (1H, s), 7.28 (1H, t, J=7.9 Hz), 6.93 (1H, d, J=7.7 Hz), 4.70 (2H, s), 4.42 (2H, bd, J=5.3 Hz), 3.52 (2H, bd, J=9.6 Hz), 3.43–3.24 (6H), 3.30 (3H, s) ppm. $^{13}$C NMR (d$_6$-DMSO): 146.37, 141.26, 140.74, 132.87, 131.58, 129.60, 129.46, 128.73, 125.11, 120.57, 117.54, 112.65, 68.83, 58.53, 5 7.38, 50.84, 48.15 ppm. IR (KBr): 3432, 2924, 2532, 2452, 1126, 954 cm$^{-1}$. CIMS (methane): 353 (100%), 352 (99%), 321 (87%).

Anal. Calc. for C$_{21}$H$_{24}$N$_2$OS•HCl: C, 64.85; H, 6.48; N, 7.20. Found: C, 65.05; H. 6.51; N, 7.36. Melting point: 216°–218° C.

EXAMPLE 45

4-(1-piperazinyl)-benzo[b]thiophene-2-methoxymethyl hydrochloride hemihydrate

The reaction is carried out by N-debenzylation as in Example 5 using 1.0 g of 4-[4-phenylmethyl-1-piperazinyl]benzo[b]thiophene-2-methanol prepared in Example 44 as starting material. The crude product is triturated with 35:65 ethyl acetate:hexane, then heated at reflux with a 1:1 mixture of acetonitrile:methanol (30 mL) and filtered to remove insoluble material. Cooling, concentration to about 10 mL under a nitrogen stream, and addition of acetonitrile (20 mL) gave a tan solid. After vacuum drying at 70° C. for 4 h, an off-white solid remained (0.77 g). 1H NMR (d$_6$-DMSO): 9.55 (2H, bs), 7.63 (1H, d, J=8.0 Hz), 7.48 (1H, d, J=0.7 Hz), 7.29 (1H, t, J=7.9 Hz), 6.94 (1H, dd, J=0.7, 8.0 Hz), 5.49 (1H, bs), 4.71 (2H, bs), 3.33 (3H, s), 3.29 (8H, bs) ppm. $^{13}$C NMR (d$_6$-DMSO): 146.92, 141.29, 140.77, 133.04, 125.14, 120.75, 117.53, 112.65, 68.85, 57.40, 48.46, 43.07 ppm. IR (KBr): 3434, 2930, 2818, 2795, 2712, 1454, 1375, 1253, 1136, 959 cm$^{-1}$. CIMS (methane): 263 (96%), 262 (70%), 231 (100%).

IC$_{50}$ 4nM (5-HT$_{1D}$ Binding Affinity)

Anal. Calc. for C$_{14}$H$_{18}$N$_2$OS•HCl•0.5H$_2$O: C, 54.62; H, 6.55; N, 9.10. Found: C, 54.50; H, 6.29; N, 9.06. Melting point: 246°–254° C., darkens >230° C.

EXAMPLE 46

4-[4-(2-(4-fluorophenyl)-ethyl)-1-piperazinyl]benzo[b]thiophene 2-methoxymethyl hydrochloride, 0.2 hydrate The compound is prepared as in Example 44 except 4-[4-[2-(4-fluorophenyl)-ethyl]-1-piperazinyl]-benzo[b]-thiophene-2-methanol (1.48 g, 4 mmol) is used as the starting alcohol. The crude product is chromatographed in 50:50 ethyl acetate:hexanes (R$_f$ of 0.6) to give a yellow solid (1.10g) of which a portion (1.02 g) is dissolved in acetonitrile (50mL), treated with 1.0M hydrochloric acid (2.9 mL), concentrated in vacuo, and vacuum dried (70° C. 9h) to a white solid (1.08 g). $^1$H NMR (d$_6$-DMSO): 11.56 (1H, bs), 7.65 (1H, d, J=8.0 Hz), 7.44 (1H, s), 7.39–7.32 (2H), 7.30 (1H, t, J=7.7 Hz), 7.20 (2H, t, J=8.8 Hz), 6.97 (1H, d, J=7.7 Hz). 4.71 (2H, s), 4.11 (1H, bs), 3.68 (2H, bd, J=11.2 Hz), 3.55 (2H, bd, J=10.7 Hz), 3.44–3.25 (6H), 3.33 (3H, s), 3.17 (2H, m) ppm. $^{13}$C NMR (d$_6$-DMSO): 162.75, 159.53, 146.37, 141.33, 140.75, 133.29, 133.25, 132.93 130.63, 130.52, 125.14, 120.49, 117.60, 115.54, 115.27, 112.74, 68.86, 57.41, 56.10, 51.15, 48.33, 28.43 ppm (includes extra peaks due to fluorine coupling). $^{19}$F NMR (d$_6$-DMSO): -115.66 ppm. IR (KBr): 3434, 2928, 2542, 2442, 1510, 1462, 1223, 1086, 959 cm$^{-1}$. CIMS (methane): 385 (100%), 384 (52%), 353 (90%), 275 (50%).

IC$_{50}$=4 nM (5-HT$_{1A}$ Binding Affinity)
IC$_{50}$=17 nM (5-HT1D Binding Affinity)
pA$_2$=7.98 (5%) (blocking of 5-HT1-like-mediated contraction in canine saphenous vein)

Anal. Calc. for C$_{22}$H$_{25}$N$_2$OS•HCl•0.2H$_2$O: C, 62.24; H, 6.27; N, 6.60. Found: C, 62.23; H, 6.18; N, 6.63. Melting point: 211°–213° C.

EXAMPLE 47

4-[4-(2-phenylethyl)-1-piperazinyl]-benzo[b]thiophene-2-carboxaldehyde

To a stirred solution of 4-[4-(2-phenylethyl)-1-piperazinyl]-benzo[b]thiophene-2-(N-methyl-N-methoxy)-carboxamide (1.81 g. 4.42 mmol), from Example 40, in dry tetrahydrofuran (15 mL) cooled in an ice bath, under nitrogen, is added lithium aluminum hydride (0.338 g, 8.9 mmol). After 2.5 h the reaction is carefully treated with aqueous 1.0M potassium hydrogen sulfate (20 ml), then water (20 mL), and saturated sodium bicarbonate (until basic, >30 mL). The product is extracted with ether (2×50 mL), the combined ether layers washed with brine (20 mL), dried with magnesium sulfate, and concentrated in vacuo. Chromatography (40:60, then 60:40, then 100:0 ethyl acetate:hexanes) gives a bright yellow-orange compound with R$_f$ of 0.35 in second solvent system (1.01 g). This is recrystallized from hexane with a little dichloromethane by slow evaporation to give an orange solid (0.67 g). $^1$H NMR (CDCl$_3$): 10.10 (1H, s), 8.11 (1H, d, J=0.8 Hz), 7.54 (1H, d, J=8.1 Hz), 7.43 (1H, d, J=8.0 Hz), 7.35–7.20 (5H), 6.94 (1H, dd, J=0.8, 7.6Hz), 3.26 (4H, m), 2.92–2.71 (8H) ppm. $^{13}$C NMR (CDCl$_3$): 184.48, 150.87, 144.43, 141.68, 140.17, 133.33, 132.76, 129.30, 128.70, 128.45, 126.14, 117.38, 113.08, 60.48, 53.43, 52.47, 33.66 ppm. IR (CHCl$_3$ solution): 28.24, 1674, 1564, 1456, 1136 cm$^{-1}$. CIMS (methane): 351 (100%), 259 (34%).

Anal. Calc. for C$_{21}$H$_{22}$N$_2$OS: C, 71.97; H, 6.33; N, 7.99. Found: C, 71.80; H, 6.27, N, 8.26. Melting point: 99°–100° C.

EXAMPLE 48

4-[4-(4-phenylcarbamoyl-butyl)-piperazin-1-yl-]benzo[b]thiophen-2-carboxylic acid ethyl ester hydrochloride To a solution of ethyl-4-(1-piperazinyl)-benzo[b]thiophene-2-carboxylate monohydrochloride prepared in Example 5 (2.00 g, 6.12 mmol) in dry N,N-dimethylformamide (31 mL) was added sodium bicarbonate (1.03 g, 12.2 mmol) and 5-iodo-N-phenylpentanamide (1.86 g, 6.12 mmol). The mixture was heated at 80° C. under nitrogen for 24 h, cooled to 20° C., treated with saturated aqueous sodium bicarbonate (50 mL) and water (100 mL), and extracted with 2:1 ether:dichloromethane (4×75 mL). The combined extracts were diluted with ethanol (50 mL) washed with water (50 mL), brine (50 mL) dried over magnesium sulfate/sodium sulfate, filtered, and concentrated in vacuo. The crude product was chromatographed using 20:80 ethanol:ethyl acetate isolating the component with an R$_f$ of ca. 0.5 (2.20 g). A solution of the product (0.20 g) in 5:2 ethanol:dichloromethane was treated with an equivalent of 1.0M hydrochloric acid and concentrated in vacuo. Recrystallization from 3:2 methanol:acetonitrile (10 mL) gave the title compound as a white solid (0.19 g).

Anal. Calc. for C$_{26}$H$_{31}$N$_3$O$_3$S•HCl: C, 62.20; H, 6.44; N, 8.37. Found: C, 62.22; H, 6.32; N, 8.31. IR(KBr): 1709, 1678, 1443, 1254 cm$^{-1}$. CIMS (methane): 466 (100%) Melting Point: 246°–248° C. (decomposition).

EXAMPLE 49

4-(1-piperazinyl)benzol[b]-thiophene-2-(N-methyl)carboxamide dihydrochloride hydrate To a solution of 4-[4-(2,2-dimethyl ethyl carboxylate)-1-piperazinyl]benzo[b]thiophene-2-(N-methyl) carboxamide (0.81 g, 2.2 mmol) in anhydrous 1,4-dioxane (20 mL) was treated with 4N hydrochloric acid/1,4-dioxane and allowed to stir for 30 min. The reaction was diluted with acetonitrile and concentrated in vacuo to a solid. The solid was recrystallized from methanol (10 mL) and acetonitrile (5 mL) with ether. The fluffy solid was suction filtered to yield product (0.2380 g). $^1$H NMR (DMSO-d$_6$): 9.61 (1H, bs), 9.53 (1H, bs), 9.07 (1H, bd, J=3.8 Hz), 8.27 (1H,s), 7.67 (1H, d, J=7.6 Hz), 7.37 (1H, t, J=7.6 Hz), 6.98 (1H, d, J=7.6 Hz), 5.02 (2H, bs), 3.34 (8H,bs), 2.84–2.83 (3H) ppm. $^{13}$C NMR (DMSO-d$_6$): 161.82, 148.14, 141.58, 139.05,133.43, 126.89, 122.33, 117.52, 112.84, 48.56, 43.18, 25.96 ppm. IR(KBr): 3451, 3422, 1632, 1553 cm$^{-1}$. CIMS (methane): 276 (100%). Melting point: 291°–294° C. (decomposition).

IC$_{50}$=8.4 nM (5-HT$_{1D}$ Binding Affinity)
Anal. Calc. for C$_{14}$H$_{17}$N$_3$OS•2HCl•0.5H$_2$O; C, 47.19; H, 5.66; N, 11.79. Found: C, 47.48; H, 5.74; N, 11.75.

EXAMPLE 50

4-[4-[2-(4-nitrophenyl)ethyl]-1-piperazinyl]-benzo[b]-thiophene-2-methanol hydrochloride To a solution of the ester product of Example 52 (1.10 g, 2.50 mmol) in anhydrous tetrahydrofuran (25 mL) was added lithium aluminum hydride (0.095 g, 2.50 mmol). The reaction stirred at room temperature under nitrogen for 0.5h additional tetrahydrofuran (25 mL) was added and stirring continued for 2 h. The reaction was treated with water (0.95 mL) then 10% aqueous sodium hydroxide (1.5 mL) then additional water (3 mL), diluted with water (0.95 mL) then 10% aqueous sodium hydroxide (1.5 mL) then additional water (3 mL), diluted with water (50 mL) and extracted with dichloromethane (3×50 mL). The combined extracts were washed with brine (50 mL), dried over magnesium sulfate/sodium sulfate, filtered and concentrated in vacuo. The crude product was chromatographed using 50:50 ethyl acetate:hexane then ethyl acetate. The component with R$_f$ of 0.8 in ethyl acetate was isolated. A solution of product (0.43 g, 1.08 mmol) in a mixture of ethanol (50 mL) and dichloromethane (20 mL) was treated with 1.0M aqueous hydrochloric acid (1.3 mL) and concentrated in vacuo. The resulting solid was recrystallized from a mixture of methanol (8 mL) and acetonitrile (15 mL) to yield yellow crystals (0.42 g). $^1$H NMR (DMSO-d$_6$): 11.69 (1H, bs), 8.26 (2H, d, J=8.9 Hz), 7.63 (3H, m), 7.32 (1H, s), 7.27 (1H, t, J=7.9 Hz), 6.96 (1H, d, J=7.6 Hz), 5.69 (1H, bs), 4.76 (2H, s), 3.70 (2H, bm), 3.53 (4H, bm), 3.32 (6H, bm) ppm. $^{13}$C NMR (DMSO-d$_6$); 146.56, 145.99, 145.20, 140.24, 133.22, 130.08, 124,56, 123.70, 119.27, 117.61, 112.62, 58.82, 55.19, 51.28, 48.33, 29.08 ppm. IR (KBr): 3266, 2373, 1516, 1343 cm$^{-1}$. CIMS (methane): 397 (30%), 380 (55%), 261 (100%).

IC$_{50}$=1 nM (5-HT$_{1A}$ Binding Affinity)
IC$_{50}$=6 nM (5-HT$_{1D}$ Binding Affinity)
Anal. Calc. for C$_{21}$H$_{23}$N$_3$O$_3$S•HCl: C, 58.13; H, 5.59; N, 9.68. Found: C, 58.20; H, 5.59; N, 9.57. Melting point: 237°-240° C. (decomposition).

EXAMPLE 51

4-(1-piperazinyl)benzo[b]thiophene-2-methanol hydrochloride

To 4-[4-(2,2-dimethyl ethyl carboxylate)-1-piperazinyl]benzo[b]thiophene-2-methanol (2.48 g, 7.12 mmol) was added 4N hydrochloric acid in 1,4-dioxane (20 mL) under nitrogen and allowed to stir for 3 h. The reaction was concentrated in vacuo. Several attempts at recrystallization failed to give analytically pure material. The final product was pale yellow in color (0.64 g). $^1$H NMR (DMSO-d$_6$): 9.54 (1H, bd), 7.61 (1H, d, J=8.0 Hz), 7.35 (1H, s), 7.25 (1H, t, J=8.0 Hz) 6.93 (1H, d, J=8.0 Hz), 4.76 (2H, s), 4.14 (2H, bs), 3.29 (8H, s) ppm. $^{13}$C NMR (DMSO-d$_6$): 146.62, 140.29, 133.36, 124.61, 117.97, 117.54, 112.50, 58.59, 48.42, 43.07 ppm. IR(KBr): 2940, 2826, 2797, 2716, 1456 cm$^{-1}$. CIMS (methane): 249 (65%), 231 (100%). Melting point: >300° C. (decomposition).

EXAMPLE 52

Ethyl 4-[4-[2-(4-nitrophenyl)ethyl]-1-piperazinyl]-benzo[b]-thiophene-2-carboxylate hydrochloride To a solution of ethyl 4-(1-piperazinyl)-benzo[b]thiophene-2-carboxylate (Example 5) (6.00 g, 18.4 mmol) in anhydrous N,N-dimethylformamide (90 mL) was added sodium bicarbonate (3.08 g, 36.7 mmol) and 2-(4-nitrophenyl) ethyl bromide (4.22 g, 18.4 mmol) and heated at 80° C. under nitrogen for 24.5 h. The reaction was allowed to stir at room temperature for 64 h. More 2-(4-mitrophenyl) ethyl bromide (4.22 g, 18.4 mmol) was added to the reaction and heated at 80° C. for 8 h. The reaction was cooled to room temperature, treated with saturated aqueous sodium bicarbonate (400 mL), diluted with water (800 mL) and extracted with ether (5×200 mL). The combined extracts were washed with water (200 mL), brine (200 mL), dried over magnesium sulfate/sodium sulfate, filtered and concentrated in vacuo. The crude product was chromatographed using ethyl acetate. The component with R$_f$ of ca. 0.9 in 20:80 ethanol:ethyl acetate was isolated (4.57 g). To a solution of product (0.10 g, 0.23 mmol) in a mixture of ethanol (10 mL) and dichloromethane (10 mL) was treated with 1M aqueous hydrochloric acid (0.25 mL) and concentrated in vacuo. The resulting solid was recrystallized from a mixture of methanol (5 mL) and acetonitrile (3 mL) to yield a tan solid (98 mg). $^1$H NMR(DMSO-d$_6$): 11.5 (1H, bs), 8.26(1H, d, J=8.7Hz), 8.10 (1H, s), 7.77 (1H, d, J=8.2 Hz), 7.64(2H, d, J=8.6 Hz), 7.50(1H, t, J=8.0Hz), 7.09 (1H, d, J=7.7 Hz), 4.37 (2H,q, J=7.2 Hz), 3.71 (2H, bm), 3.59 (2H, bm), 3.55-3.20 (8H), 1.35 (3H, t, J=7.2 Hz) ppm. $^{13}$C NMR (DMSO-d$_6$): 161.86, 148.22, 146.49, 145.33, 142.81, 132.60, 131.96, 130.08, 128.33, 127.81, 123.75, 117.99, 113.69, 61.48, 55.28, 51.11, 48.77, 29.05, 14.15 ppm. IR (KBr): 1711, 1522, 1348, 1256, 1246 cm$^{-1}$. CIMS (eE=70eV): 303 (100%).

Anal. Calc. C$_{23}$H$_{25}$N$_3$O$_4$S•HCl: C, 58.04; H, 5.52; N, 8.83. Found: C, 57.99; H, 5.43; N, 8.70. Melting Point: 252°-254° C. (decomposition).

EXAMPLE 53

5-[4-(2-Hydroxymethyl-benzo[b]thiophen-41-yl)-piperazin-1-yl]-pentanoic acid phenyl amide hydrochloride A suspension of 4-[4-(4-phenylcarbamoyl-butyl)-piperazin-1-yl]-benzo[b]thiophen-2-carbozylic acid ethyl ester (1.20 g, 2.58 mmol from Example 48) in dry tetrahydrofuran was treated with a molar equivalent of lithium aluminum hydride under nitrogen at room temperature for 18 h, then treated sequentially with water (0.10 mL), 10% aqueous sodium hydroxide (0.15 mL), and water (0.3 mL). The reaction was filtered, concentrated in vacuo, and chromatographed using 0:100, then 20:80 ethanol:ethyl acetate, isolating the component with an R$_f$ of ca. 0.4 in the latter system to give 0.93 g (2.20 mmol). This was dissolved in 5:2 ethanol:dichloromethane (70 mL), treated with 1.0M hydrochloric acid (2.3 mL), concentrated in vacuo, and recrystallized from methanol:acetonitrile to give the title compound as a dark tan solid (0.86 g).

Anal. Calc. for C$_{24}$H$_{29}$N$_3$O$_2$S•HCl•0.4H$_2$O: C, 61.70; H, 6.64; N, 8.99. Found: C, 61.91; H, 6.64; N, 9.00. IR (KBr): 3408, 1599, 1541, 1443 cm$^{-1}$. CIMS (methane): 424 (100%). Melting Point: 118°-121° C. (decomposition).

EXAMPLE 54

2-[4-(4-phenethyl-piperazin-1-yl)-benzo[b]thiophen-2-ylmethyl]-isoindole-1,3-dione hydrochloride Anhydrous tetrahydrofuran (30 mL) was added to a flask containing 4- [4- (2-phenylethyl ) -1-piperazinyl]-benzo[b]thiophene-2-methanol (3.20 g, 9.08 mmol), triphenylphosphine (2.50 g, 9.53 mmol) and phthalimide (1.40 g, 9.53 mmol). The reaction was cooled to 0° C. in an ice bath and diethyl azodicarboxylate (1.5 mL, 9.53 mmol) was added over 3 min. The bath was removed after stirring under nitrogen for 20 min and allowed to stir at room temperature for 15.5 h. The reaction was concentrated in vacuo and the crude product was chromatographed using 40:60 ethyl acetate:hexane. The component with $R_f$ of ca. 0.4 was isolated. The compound was rechromatographed to remove a by product using 95:5 dichloromethane:acetone, then using 5:95 acetic acid: ethyl acetate. the component with $R_f$ of ca. 0.3 was isolated (3.26 g), along with acetic acid. The compound was dissolved in dichloromethane (75 mL), washed with saturated aqueous sodium bicarbonate (50 mL), dried over magnesium sulfate/sodium sulfate, filtered and concentrated in vacuo (2.80 g). A solution of product (1.00 g, 2.08 mmol) in a mixture of ethanol (50 mL) and dichloromethane (50 mL) was treated with 1.0M aqueous hydrochloric acid (2.10 mL) and concentrated in vacuo. The resulting solid was recrystallized from a mixture of methanol (50 mL), dichloromethane (80 mL) and water (8 drops) to yield the title compound (0.87 g). $^1$H NMR (DMSO-$d_6$+CD$_3$OD+D$_2$O): 7.85 (4H, m), 7.54 (1H, d, J=7.8 Hz), 7.45 (1H, s), 7.31 (6H, m), 6.96 (1H, d, J=7.8 Hz), 5.04 (2H, s), 3.60-3.10 (10H), 3.01 (2H, m) ppm. $^{13}$C NMR (DMSO-$d_6$+CD$_3$OD+D$_2$O): 168.56, 147.08, 141.37, 139,90, 135.89, 133.75, 131.94, 129.64, 127.93, 126.53, 124.35, 122.11, 118.74, 114.07, 57.78, 52.51, 49.74, 37.49, 30.53 ppm. IR (KBr): 2456, 2434, 1769, 1719, 1427, 1393, 1356 cm$^{-1}$. CIMS (methane): 482 (100%).

Anal. Calc. for C$_{29}$H$_{27}$N$_3$O$_2$S•HCl: C, 67.24; H, 5.46; N, 8.11. Found: C, 67.01; H, 5.48; N, 7.93. Melting Point: 297°-300° C. (decomposition).

EXAMPLE 55

4-[4-(2-phenylethyl)-1-piperazinyl]-benzo[b]thiophene-2-methanamine dihydrochloride To a suspension of 2-[4-(4-phenethyl-piperazin-1-yl)benzo[b]thiophen-2-ylmethyl]-isoindole-1,3-dione (Example 54) (1.80 g, 3.74 mmol) in ethanol (16 mL) was added hydrazine monohydrate (0.58 mL, 12 mmol). The reaction was heated at reflux for 30 min under nitrogen. Additional ethanol (16 mL) was added and reflux was continued for 45 min. The reaction stirred at room temperature for 15 h then reflux was resumed for 6 h. The reaction was cooled to room temperature, diluted with ether (100 mL) and suction filtered with ether washes. The filtrate was concentrated in vacuo and the crude product was chromatographed using ethyl acetate then 20:80 ethanol: ethyl acetate then 50:50 ethanol:ethyl acetate. The component with $R_f$ of ca. 0.1 in the first solvent system was isolated. A solution of product (1.23 g, 3.50 mmol) in a mixture of ethanol (50 mL) and dichloromethane (50 mL) was treated with 1.0M aqueous hydrochloric acid (7.0 mL) and concentrated in vacuo. The resulting oily solid was reconcentrated form acetonitrile and vacuum dried with heat to yield a tan solid (1.12 g). $^1$H NMR (DMSO-$d_6$): 11.66 (1H, bs), 8.88 (2H, bs), 7.78 (1H, s), 7.68 (1H, d, J=8.0 Hz), 7.62 (6H, m), 6.98 (1H, d, J=8.0 Hz), 4.33 (2H, s), 3.64 (4H, bm), 3.50-3.20 (7H), 3.17 (2H, m) ppm. $^{13}$C NMR (DMSO-$d_6$): 146.44, 140.87,137.11, 135.17, 132.73, 128.64, 126.76, 125.63, 123.52, 117.39, 112.71, 56.01, 51.22, 48.24, 37.39, 29.35 ppm. IR (KBr): 3426, 2930, 2899, 2874, 2839, 1456 cm$^{-1}$. CIMS (methane): 352 (76%), 260 (100%).

IC$_{50}$=3 nM (5-HT$_{1A}$ Binding Affinity)
IC$_{50}$=12 nM (5-HT$_{1D}$ Binding Affinity)

Anal. Calc. for C$_{21}$H$_{25}$N$_3$S•HCl•0.7H$_2$O: C, 57.72; H, 6.55; N, 9.61. Found: C, 57.61; H, 6.38; N, 9.54. Melting Point: 189°-193° C. (decomposition).

EXAMPLE 56

[4-(4-phenethyl-piperazin-1-yl)-benzo[b]thiophen-2-yl]-piperidin-1-yl methanone hydrochloride To a solution of piperidine (1.13 mL, 1.41 mmol) in anhydrous toluene (40 mL,) was added 2.0M trimethylaluminum in toluene (6.0 mL, 11.41 mmol). The reaction was allowed to stir for 5 min, then added ethyl-4-[4-(2-phenylethyl)-1-piperazinyl]-benzo[b]thiophene-2-carboxylate, from Example 6, (1.50 g, 3.80 mmol) and heated at 60° C. under nitrogen for 23 h. The reaction was cooled to room temperature, poured into water (150 mL) and extracted with dichloromethane (4×100 mL). The combined extracts were washed with brine (100 mL), dried over magnesium sulfate/sodium sulfate, filtered and concentrated in vacuo. The crude product was chromatographed using ethyl acetate. the component with $R_f$ of ca. 0.5 was isolated. To a solution of product (1.57 g, 3.62 mmol) in a mixture of ethanol (50 mL) and dichloromethane (10 mL) was treated with 1M aqueous hydrochloric acid (3.65 mL) and concentrated in vacuo. The resulting solid was recrystallized from a mixture of methanol (15 mL) and acetonitrile (10 mL) to yield an off-white solid (1.47 g). $^1$H NMR (DMSO-$d_6$): 11.24 (H, bs), 7.72 (1H, d, J=7.9 Hz), 7.63 (1H, s), 7.36 (6H, m), 7.04 (1H, d, J=7.9 Hz), 3.62 (8H, m), 3.50-3.20 (6H), 3.15 (2H, m), 1.65 (2H,m), 1.57 (4H, m) ppm. $^{13}$C NMR (DMSO-$d_6$): 162.34, 147.28,140.54, 137.04, 136.05, 132.36, 128.74, 128.67, 126.80, 126.59, 122.26, 117.53, 113.24, 56.13, 51.12, 48.57, 29.29, 25.72, 25.63, 23.96 ppm. IR (KBr): 1618, 1452, 1433, 1267, 1258 cm$^{-1}$. CIMS (methane): 434 (100%).

IC$_{50}$=135 nM (5-HT$_{1D}$ Binding Affinity)
pA$_2$=6.95 (2%) (blocking of 5-HT1-like-mediated contraction in canine saphenous vein)

Anal. Calc. C$_{26}$H$_{31}$N$_3$OS•.HCl: C, 66.43; H. 6.88; N, 8.94. Found: C, 66.48; H, 6.73; N, 8.92. Melting Point: 248°-252° C. (decomposition).

EXAMPLE 57

[4-(4-phenethyl-piperazin-1-yl)-benzo[b]thiophen-2-yl]-pyrrolidin-1-yl methanone hydrochloride To a solution of pyrrolidine (1.0 mL, 11.4 mmol) in anhydrous toluene (40 mL) was added 2.0M trimethyl aluminum in toluene (6.0 mL, 12.0 mmol) under nitrogen and allowed to stir at room temperature for 15 min. To this solution was added ethyl-4-[4-2-phenylethyl)-1-piperazinyl]benzo[b]thiophene-2-carboxylate from Example 6 (1.5 g, 3.8 mmol). The reaction was heated at 60° C. for 26.5 h. The reaction was cooled to room temperature, poured into water (150 mL) and extracted with dichloromethane (4×100 mL). The combined extracts were washed with brine (100 mL), dried over magnesium sulfate/sodium sulfate and concentrated in vacuo. The crude product was chromatographed using ethylacetate. The component with $R_f$ of ca. 0.5 was isolated. To a solution of product (1.52 g, 3.62 mmol) in a mixture of ethanol (50 mL) and dichloromethane (10 mL) was treated with 1.0M aqueous hydrochloric acid (3.65 mL) and concentrated in vacuo. The resulting solid was recrystallized from a mixture of methanol (20 mL) and acetonitrile (20 mL) to yield offwhite crystals (1.56 g). 1H NMR (DMSO-$d_6$): 10.71 (1H, bs), 7.82 (1H, s), 7.71 (1H, d, J=8.5 Hz), 7.35 (6H, m), 7.04 (1H, d, J=8.5 Hz), 3.84 (2H, t, J=5.8 Hz), 3.64 (6H, m), 3.50–3.05 (8H), 2.48 (4H, m) ppm. $^{13}$C NMR (DMSO-$d_6$): 160.95, 147.57, 141.04, 136.94, 132.92, 128.68, 127.00, 126.85, 123.25, 117.51, 113.19, 56.18, 51.23, 48.71, 47.18, 29.23, 26.23, 23.64 ppm. IR (KBr): 1603, 1522, 1452, 1418 cm$^{-1}$. CIMS (methane): 420 (100%).

$IC_{50}$=25 nM (5-HT$_{1D}$ Binding Affinity)

$pA_2$=8.37 (0%) (blocking of 5-HT1-like-mediated contraction in canine saphenous vein)

Anal. Calc. for $C_{25}H_{29}N_3OS\bullet HCl$: C, 65.84; H, 6.65; N, 9.21. Found: C, 65.82; H, 6.87; N, 9.36. Melting Point: 269°–275° C. (decomposition).

EXAMPLE 58

3-[4-(4-phenethyl-piperazin-1-yl)-benzo[b]thiophen-2-yl]acrylic acid ethyl ester hydrochloride Triethylphosphonoacetate (0.57 mL, 2.85 mmol) was added to a suspension of sodium hydride (0.11 g, 2.85 mmol) in anhydrous tetrahydrofuran (4.0 mL) under nitrogen at room temperature. After stirring 30 minutes, 4-[4-(2-phenylethyl)-1-piperazinyl]-benzo[b]thiophene-2-carboxaldehyde (Example 47) (1.00 g, 2.85 mmol) was added. Additional tetrahydrofuran (4.0 mL) was added and the reaction was heated at reflux for 17 h, then poured into water (100 mL) and extracted with ether (3×100 mL). The combined extracts were washed with brine (100 mL), dried over magnesium sulfate/sodium sulfate, filtered and concentrated in vacuo. The crude product was chromatographed using 30:70 ethyl acetate:hexane. The component with Rf of ca. (40:60 ethyl acetate:hexane) was isolated (0.71 g). A solution of product (0.71 g, 1.69 mmol) in ethanol (50 mL) and dichloromethane (10 mL) was treated with 1.0M aqueous hydrochloric acid (1.75 mL) and concentrated in vacuo. The resulting solid was recrystallized from a mixture of methanol and dichloromethane to yield the title compound as a yellow solid (0.55 g). $^1$H NMR (DMSO-$d_6$): 11.30 (1H, bs), 8.02 (1H, s), 7.97 (1H, d, J=15.6 Hz), 7.66 (1H, d, J=7.8 Hz), 7.42–7.26 (6H), 6.99 (1H, d, J=7.7 Hz), 6.33 (1H, d, J=15.6 Hz), 4.21 (2H, q, J=7.2 Hz), 3.77–3.56 (4H), 3.52–3.21 (6H), 3.21–3.10 (2H) 1.27 (3H, t, J=7.2 Hz) ppm. $^{13}$C NMR (DMSO-$d_6$): 165.63, 147.26, 141.16, 137.69,137.52, 137.06, 133.05, 128.69, 127.98, 127.45, 126.81, 118.58, 117.43, 113.17, 60.23, 56.11, 51.16, 48.35, 29.34, 14.16 ppm. IR (KBr): 1079, 1624, 1458, 1262, 1165 cm$^{-1}$. CIMS (methane): 421 (100%).

Anal. Calc. for $C_{25}H_{28}N_2O_2S\bullet HCl$: C, 65.70; H, 6.41; N, 6.31. Found: C, 65.42; H, 6.53; N, 6.14.

EXAMPLE 59

3-[4-(4-phenethyl-piperazin-1-yl)-benzo[b]thiophen-2-yl]-prop-2-en-1-ol hydrochloride The 3-[4-(4-phenethyl-piperazin-1-yl)-benzo[b]thiophen-2-yl]-acrylic acid ethyl ester (Example 58) (1.25 g, 2.97 mmol) was added to a solution of diisobutyl aluminum hydride (15 mL of 1.0M in toluene, 15.0 mmol) in dichloromethane cooled to 78° C. (30 mL). The reaction stirred for 1.75 h, quenched with methanol (30 mL) and warmed to room temperature. The reaction was diluted with ether, filtered through Celite and the filtrate was concentrated in vacuo. The crude product was chromatographed using 40:60 ethyl acetate:hexane then ethyl acetate. The component with $R_f$ of ca. 0.1 (40:60 ethyl acetate:hexane) was isolated. A solution of product (0.87 g, 2.30 mmol) in ethanol (50 mL) and dichloromethane (1.0 mL) was treated with 1.0 m aqueous hydrochloric acid (2.40 mL) and concentrated in vacuo. The resulting solid was recrystallized form methanol to yield solid (0.86 g). $^1$H NMR (DMSO-$d_6$): 10.90 (1H, bs), 7.59 (1H, d, J=8.0 Hz), 7.43–7.25 (7H), 6.91 (2H, m), 6.25 (1H, dt, J=15.8, 4.8 Hz), 5.02 (1H, bs), 4.15 (2H, bs), 3.75–3.51 (4H), 3.51–3.27 (4H), 3.27–3.08 (4H) ppm. $^{13}$C NMR (DMSO-$d_6$): 146.23, 141.14, 139.26, 137.10, 133.61, 133.50 128.65, 128.63, 126.76, 125.43, 122.23, 120.27, 117.32, 112.90, 60.85, 56.19, 51.18, 48.31, 29.32 ppm. IR (KBr): 3395, 2581, 1568, 1458, 959 cm$^{-1}$. CIMS (methane): 379 (100%), 361 (75%), 287 (92%) . Melting Point: 201°–204° C. (decomposition). $pA_2$=9.26 ( 0% ) (blocking of 5-HT1-like-mediated contraction in canine saphenous vein)

Anal. Calc. for $C_{23}H_{26}N_2OS\bullet HCl$: C, 66.57; H, 6.57; N, 6.75. Found: C, 66.42; H, 6.51; N, 6.70.

EXAMPLE 60

A)

3-[4-(4-phenethyl-piperazin-1-yl)-benzo[b]thiophen-2-yl]-acrylonitrile hydrochloride

B)

3-[4-(4-phenethyl-piperazin-1-yl)-benzo[b]thiophen-2-yl]-acrylamide hydrochloride hydrate To ammonium chloride (0.61 g, 11.41 mmol) was added anhydrous dichloromethane (95 mL) and 2.0M trimethyl aluminum in toluene (5.7 mL, 11.4 mmol). After stirring for 15 minutes, 3-[4-(4-phenethyl-piperazin-1-yl)benzo[b]thiophen-2-yl]-acrylic acid ethyl ester (Example 58) (1.60 g, 3.80 mmol) was added. The reaction was heated at reflux under nitrogen for 21.5 h. The reaction was cooled to room temperature, poured into water (200 mL) and extracted with dichloromethane (4×100 mL). The combined extracts were washed with brine (100 mL), dried over magnesium sulfate/sodium sulfate, filtered and concentrated in vacuo. The crude product was chromatographed using 60:40 ethyl acetate:hexane, then ethyl acetate, then 20:80 ethanol: ethyl acetate. Two components were isolated: A ($R_f$of ca. 0.4 in 40:60 ethyl acetate:hexane) and B ($R_f$ of ca. 0.1 in 40:60 ethyl acetate:hexane).

A solution of component A (0.14 g, 0.37 mmol) in ethanol (50 mL) and dichloromethane (10 mL) was treated with 1.0M aqueous hydrochloric acid (0.40 mL) and concentrated in vacuo. The resulting solid was recrystallized from methanol and dichloromethane to yield the title compound A as yellow crystals (0.13 g). $^1$H NMR (DMSO-$d_6$): 11.30 (1H, bs), 7.92 (2H, d, J=16.7 Hz), 7.69 (1H, d, J=8.0 Hz), 7.44–7.25 (6H), 7.01 (1H, d, J=7.8 Hz), 6.24 (1H, d, J=16.5 Hz),3.78–3.65 (2H), 3.65–3.52 (2H), 3.51–3.21 (6H), 3.21–3.09 (2H) ppm. $^{13}$C NMR (DMSO-$d_6$): 147.50,143.51, 141.24, 137.09, 132.89, 128.68, 127.77, 127.56, 126.81, 118,37, 117.58, 113.44, 97.19, 56.14, 51.14, 48.46, 29.38 ppm. IR (KBr): 2212, 1607, 1456, 959 cm$^{-1}$. CIMS (methane): 374 (100%). Melting Point: 285°–289° C. (decomposition).

Anal. Calc. for C$_{23}$H$_{23}$N$_3$S•HCl: C, 67.37; H, 5.91; N, 10.25. Found: C, 67.27; H, 5.96; N, 10.31.

A solution of component B (1.12 g, 2.86 mmol) in ethanol (50 mL) and dichloromethane (25 mL) was treated with 1.0M aqueous hydrochloric acid (3.0 mL) and concentrated in vacuo. The resulting solid was recrystallized from methanol and dichloromethane to yield title compound B as a yellow solid (0.85 g). $^1$H NMR (DMSO-d$_6$): 11.18 (1H, bs), 7.82 (1H, s), 7.74 (1H, d, J=15.4 Hz), 7.6 (1H, s, 7.64 (1H, d, J=8.2 Hz), 7.40–7.27 (6H), 7.17 (1H, s), 6.98 (1H, d, J=7.6 Hz), 6.44 (1H, d, J=15.4 Hz), 3.75–3.65 (2H), 3.65–3.55 (H), 3.49–3.21 (9H), 3.19–3.10 (3H) ppm. $^{13}$C NMR (DMSO-d$_6$): 165.91, 146.91, 140.31, 138.76, 137.04, 133.26, 132.82, 128.68, 126.86, 126.80, 126.23, 126.42, 117.4, 113.12, 56.13, 51.18, 48.37, 29.35 ppm. IR (KBr): 1667, 1622, 1601, 1458, 1381 cm$^{-1}$. CIMS (methane): 392 (100%). Melting Point: 165°–170° C. (decomposition).

Anal. Calc. for C$_{23}$H$_{25}$N$_3$OS•HCl•H$_2$O: C, 61.94; H, 6.34; N, 9.42. Found: C, 62.18; H, 6.29; N, 9.35.

EXAMPLE 61

3-[4-(4-phenethyl-piperazin-1-yl)-benzo[b]thiophen-2-yl]-propionic acid ethyl ester hydrochloride Zinc dust (5.72 g, 87.51 mmol) was added to a suspension of 3-[4-(4-phenethyl-piperazin-1-yl)-benzo[b]thiophen-2-yl]-acrylic acid ethyl ester (Example 58) (4.60 g, 10.94 mmol) and nickel (II) chloride hexahydrate (5.20 g, 21.88 mmol) in ethanol (100 mL). The reaction was heated at reflux for 21 h under nitrogen. The reaction was cooled to room temperature, filtered through Celite with ether washes and the filtrate was concentrated in vacuo. The crude product was chromatographed using 40:60 with acetate:hexane then ethyl acetate. The component with R$_f$ of ca. 0.5 in 40:60 ethyl acetate:hexane was isolated to give the free amine of the tile compound (3.39 g). A solution of product (0.89 g, 2.11 mmol) in ethanol (50 mL) was treated with 1.0M aqueous hydrochloric acid (2.2 mL) and concentrated in vacuo. The resulting solid was recrystallized from methanol and ether to yield a white solid (0.68 g). $^1$H NMR (DMSO-d$_6$): 11.38 (1H, bs), 7.59 (1H, d, J=8.1 Hz), 7.41–7.22 (7H), 6.94 (1H, d, J=7.6 HZ), 4.09 (2H, q, J=7.1 Hz), 3.75–3.64 (2H), 3.58–3.48 (2H), 3.47–3.23 (10H), 3.23–3.10 (2H), 2.76 (2H, t, J=7.3 Hz), 1.18 (3H, t, J=7.1 Hz) ppm. $^{13}$C NMR (DMSO-d$_6$): 171.71, 145.80, 143.30, 139.97, 137.09, 133.44, 128.67, 126.80, 124.52, 119.14, 117.38, 112.65, 60.04, 56.17, 51.20, 48.28, 34.82, 29.32, 25.43, 14.07 ppm. IR (KBr): 1732, 1456, 1250, 1202, 1118 cm$^{-1}$. CIMS (methane): 423 (100%), 331 (70%). Melting Point: 175°–178° C. (decomposition).

Anal. Calc. for C$_{25}$H$_{30}$N$_2$O$_2$S•HCl: C, 65.41; H, 6.82; N, 6.10. Found: C, 65.51; H, 6.91; N, 6.12.

EXAMPLE 62

3.-[4-(4-phenethyl-piperazin-1-yl)-benzo[b]thiophen-2-yl]-propan-1-ol hydrochloride Lithium aluminum hydride (0.22 g, 5.68 mmol) was added to a solution of 3-[4-(4-phenethyl-piperazin-1-yl)benzo[b]thiophen-2-yl]-propionic acid ethyl ester (from Example 61) (1.20 g, 2.84 mmol) in anhydrous tetrahydrofuran (28 mL). The reaction stirred at room temperature for 1.5 h under nitrogen. The reaction was treated with H$_2$O (0.22 mL), 10% aqueous sodium hydroxide (0.33 mL), additional H$_2$O (0.66 mL), then diluted with H$_2$O (50 mL) and extracted with ether (3×100 mL). The combined extracts were washed with brine (100 mL), dried over magnesium sulfate/sodium sulfate, filtered and concentrated in vacuo. The crude product was chromatographed using 60:40 ethyl acetate:hexane. The component with R$_f$ of ca. 0.1 in 40:60 ethyl acetate:hexane was isolated. A solution of product (1.03 g, 2.71 mmol) in ethanol (50 mL) and dichloromethane (10 mL) was treated with 1.0M aqueous hydrochloric acid (2.75 mL) and concentrated in vacuo. The resulting solid was recrystallized from methanol and ether to yield white crystals (0.95 g). $^1$H NMR (DMSO-d$_6$): 11.35 (1H, bs), 7.58 (1H, d, J=8.4 Hz), 7.39–7.19 (7H), 6.93 (1H, d, J=7.6 Hz), 4.60 (1H, bs), 3.75–3.60 (2H), 3.59–3.09 (12H), 2.95 (2H, t, J=7.5 Hz), 1.84 (2H, m) ppm. $^{13}$C NMR (DMSO-d$_6$): 145.69, 145.33, 139.87, 137.09, 133.64, 128.68, 126.80, 124.29, 118.58, 117.41, 112.64, 59.75, 56.20, 51.22, 48.34, 34.11, 29.30, 26.76 ppm. IR (KBr): 3364, 2924, 2581, 1462, 1420, 959 cm$^{-1}$. CIMS (methane): 381 (100%). Melting Point: 227°–229° C. (decomposition).

Anal. Calc. for C$_{23}$H$_{28}$N$_2$OS•HCl: C, 66.25; H, 7.02; N, 6.72. Found: C, 66.44; H, 7.12; N, 6.76.

EXAMPLE 63

A)
3-[4-(4-phenethyl-piperazin-1-yl)-benzo[b]thiophen-2-yl]-propionitrile hydrochloride B) 3-[4-(4-phenethyl-piperazin-1-yl)-benzo[b]thiophen-2-yl]propionamide hydrochloride To ammonium chloride (0.49 g, 9.23 mmol) was added dichloromethane (75 mL) and 2.0M trimethyl aluminum in toluene (4.6 mL, 9.23 mmol). After stirring for 15 minutes under nitrogen, 3-[4-(4-phenethyl-piperazin-1-yl)benzo[b]thiophen-2-yl]-propionic acid ethyl ester (from Example 61) was added (1.30 g, 3.08 mmol) and the reaction was heated at reflux for 21 h. The reaction was cooled to room temperature, poured into ether (200 mL) and extracted with dichloromethane (4×100 mL). The combined extracts were washed with brine (100 mL), dried over magnesium/sodium sulfate, filtered and concentrated in vacuo. The crude product was chromatographed using 40:60 ethyl acetate:hexane, then ethyl acetate, then 20:80 ethanol:ethyl acetate. Two components were isolated: A (R$_f$ of ca. 0.4 in 40:60 ethyl acetate:hexane) and B (R$_f$ of ca. 0.1). Component B was rechromatographed using 5:95 ethanol:ethyl acetate.

A solution of component A (0.33 g, 0.88 mmol) in ethanol (50 mL) and dichloromethane (10 mL) was treated with 1.0M aqueous hydrochloric acid (0.9 mL) and concentrated in vacuo. The resulting solid was recrystallized from methanol and acetonitrile to yield the first tile compound as a tan solid (0.31 g). $^1$H NMR (DMSO-d$_6$): 11.40 (1H, bs), 7.63 (1H, d, J=7.9 Hz), 7.40–7.26 (7H), 6.97 (1H, d, J=7.5 Hz), 3.75–3.64 (2H), 3.61–3.50 (2H), 3.48–3.09 (10H), 2.98 (2H, t, J=7.1 Hz) ppm. $^{13}$C NMR (DMSO-d$_6$): 145.99, 141.28, 140.21, 137.10, 133.29, 128.67, 126.80, 124.85, 120.16, 119.88, 117.54, 112.76, 56.16, 51.17, 48.29, 29.33, 25.93, 18.37 ppm. IR (KBr): 3434, 2415, 1454, 1248, 957, 779 cm$^{-1}$. CIMS (methane): 376 (100%). Melting Point: 196°–198° C. (decomposition).

Anal. Calc. for C$_{23}$H$_{25}$N$_3$S•HCl: C, 67.07; H, 6.38; N, 10.20. Found: C, 67.25; H, 6.38; N, 9.96.

A solution of rechromatographed B (0.71 g, 1.8 mmol) in ethanol (50 mL) and dichloromethane (40 mL) was treated with 1.0M aqueous hydrochloric acid (1.85 mL and concentrated in vacuo. The resulting solid was recrystallized from methanol and acetonitrile to yield the second title compound as an off-white solid (0.56 g). $^1$H NMR (DMSO-d$_6$): 11.32 (1H, bs), 7.58 (1H, d, J=8.0 Hz), 7.43–7.22 (8H), 6.94 (1H, d, J=7.5 Hz), 6.87 (1H, bs), 3.75–3.64 (2H), 3.59–3.48 (2H), 3.47–3.20 (8H), 3.20–3.07 (4H), 2.53–2.48 (2H) ppm. $^{13}$C NMR (DMSO-d$_6$): 172.74, 145.72, 144.44, 140.00, 137.08, 133.49, 128.69, 126.81, 124.38, 118.81, 117.38, 112.61, 56.20, 51.22, 48.32, 36.28, 29.32, 25.99 ppm. IR (KBr): 3416, 1670, 1456, 1422, 1404 cm$^{-1}$. CIMS (methane): 394 (100%). Melting Point: 211°–213° C. (decomposition).

The compounds of Formula I are serotonin 5HT1A receptor agents and are therefore useful in the treatment of anxiety, hypertension, and depression. The affinity of the compounds for the 5HT$_{1A}$ receptor can be demonstrated by receptor binding assay procedures such as described by Gozlan et al. in *Nature*, Volume 305, at pages 140–142 (1983). The procedure of Sleight et al., as reported in the *European Journal of Pharmacology*, Volume 154, pages 255–261 (1988) can be utilized to show that this affinity results in an agonistic effect upon the receptor.

The compounds slow the firing of neurons in the dorsal raphe nucleus which contains one of the highest densities of 5HT$_{1A}$ receptors in the CNS. Inhibition of cell firing results in a reduction in the amount of serotonin released in brain regions receiving input from the dorsal raphe, thereby altering serotonin tone in the system. A slowing of the firing rate can be demonstrated by applying the compounds to rodent brain slices containing the dorsal raphe and measuring the activity of individual neurons. This procedure has been described by Sprouse et al., in the *European Journal of Pharmacology*, Vol. 167, pp 375–383 (1989). Other 5HT$_{1A}$ agonists such as buspirone have been shown to inhibit raphe cell firing, an effect apparently common to all members of this pharmacologic class (Vandermaelen et al., *European Journal of Pharmacology*, Vol. 129, pp 123–130 (1986)).

It has been reported that 5HT$_{1A}$ receptor agents are effective in the treatment of depression. The 5HT$_{1A}$ agonist, 8-hydroxy-2-(di-N-propylamino) tetralin (8-OH DPAT) was shown to be effective in rodent models for depression. *European Journal of Pharmacology*, Vol 144., pages 223–229 (1987), Ceroo et al. and *European Journal of Pharmacology*, Vol. 158, pages 53–59 (1988), Ceroo et al. Schweizer et al. reported that buspirone, a partial 5HT$_{1A}$ agonist, was useful in the treatment of depression. *Pharmacology Bulletin*, Vol. 22, No. 1 (1986). Since the compounds of the instant invention are 5HT$_{1A}$ receptor agents, they will be useful in the treatment of depression.

In order to exhibit an antidepressant effect, it is necessary that the compounds be administered to the patient in an effective amount. The dosage range at which these compounds exhibit this antidepressant effect can vary widely depending upon the severity of the patient's depression, the particular compound being administered, the route of administration, the co-administration of other therapeutic agents, and the presence of other underlying disease states. Typically, the compounds will be administered at a dosage range of from 0.5 mg/kg/day to about 100 mg/kg/day. Repetitive daily administration may be desirable and will vary with the conditions described above. However, the compounds are typically administered from 1 to 4 times daily.

The compounds of Formula I will elevate the patient's mood if they are suffering from depression and either relieve or alleviate the physical complaints which the patient is experiencing.

As noted above, the compounds of Formula I are serotonin 5HT$_{1A}$ agonists. Compounds producing this effect at the 5HT$_{1A}$ receptor have also been found to exhibit anxiolytic properties. *European Journal of Pharmacology*, Vol. 88, pages 137–138 (1983) Gloser et al. and *Drugs of the Future* Vol. 13 pages 429–439 (1988) Glaseat. A 5HT$_{1A}$ partial agonist known as buspirone is currently being marketed as an anxiolytic agent. Since the compounds of the instant invention are are 5HT$_{1A}$ agonists, they will be useful in the treatment of anxiety.

It is also possible to demonstrate the anxiolytic activity of these compounds by their ability to block distress vocalizations in rat pups. This test is based upon the phenomenon that when a rat pup is removed from its litter, it will emit an ultrasonic vocalization. It was discovered that anxiolytic agents block these vocalizations. The testing method has been described by Gardner, C. R., Distress vocalization in rat pups: a simple screening method for anxiolytic drugs., *J. Pharmacol. Methods* 14:181–1879 (1985), and Insel et al., Rat pup ultrasonic isolation calls: Possible mediation by the benzodiazepine receptor complex, *Pharmacol. Biochem. Behav.*, 24:1263–1267 (1986).

Alternatively, the following methodology can be utilized to demonstrate their utility. Animals were trained and tested for tear-potentiated startle in a modification of the methods reported in Hitchcock and Davis (1991). Briefly, rats first were given a matching session consisting of 30 startle stimuli. This data was used to match rats into groups with similar baseline startle amplitudes. A training session took place one to two days later in which the rats were given 10 paired trials consisting of a visual conditioned stimulus (a light) immediately followed by an unconditioned stimulus (footshock). The test session took place two days later. The product of Example No. 15 was administered s.c. in the flank and fifteen minutes later, the rats were given startle stimuli in the absence of the conditioned stimulus (baseline startle measurement; Noise-Alone trials) or in the presence of the conditioned stimulus (fear-potentiated startle measurement; Light-Noise trials). Fear-potentiated startle was defined as higher startle in the presence of the conditioned fear stimulus than in its absence.

Statistical analysis was done on the mean startle amplitudes on the Noise-Alone and Light-Noise trials, and the mean Difference scores (Light-Noise minus Noise-Alone means). One-way analysis of variance was run on the Difference scores and on the Noise-Alone scores. Multiple comparison test (Fisher PLSD) were used to compare each dose group to the vehicle control group. The following results were obtained:

This compound showed significant anxiolytic activity in the fear-potentiated startle test. This is a measure of conditioned fear in which rats exhibit an enhanced acoustic startle reflex in the presence of a cue that has previously been associated with shock. The fear-potentiated startle test is sensitive to anxiolytic properties of both 5-HT$_{1A}$ partial agonists and benzodiazepine agonists. This compound decreased fear-potentiated startle with statistically significant effects at doses of 2.5, 20.0, and 40.0 mg/kg s.c. The compound did not decrease the baseline startle reflex, indicating that it does not have muscle relaxant activity.

In order to exhibit this anxiolytic effect, it is necessary that the compounds be administered to the patient in an effective amount. The dosage range at which these compounds exhibit this anxiolytic effect can vary widely depending upon the severity of the patient's anxiety, the particular compound being administered, the route of administration, the co-administration of other therapeutic agents, and the presence of other underlying disease states. Typically, the compounds will be administered at a dosage range of from about 0.5 mg/kg/day to about 100 mg/kg/day. Repetitive daily administration may be desirable and will vary with the conditions described above. However, the compounds are typically administered from 1 to 4 times daily.

The compounds of Formula I exhibit a hypotensive effect and are therefore useful in the treatment of hypertension. Other $5HT_{1A}$ agonists such as 8-OH-DPAT and flesinoxan have been shown to be effective for the treatment of hypertension in rodent models *European Journal of Pharmacology*, Vol. 180, pages 339–349 (1990) and *European Journal of Pharmacology*, Vol. 182, pages 63–72 (1990). It is also possible to demonstrate the antihypertensive effects of these compounds using rodent models such as the spontaneously hypertensive rat. In this model, vehicle is administered to the rat orally or intravenously and a baseline blood pressure is established. The test compound is then administered by the same route and the decrease in blood pressure is noted. The compounds of Formula I produce a hypotensive effect.

In order to produce an antihypertensive effect, it is necessary that the compounds be administered to the patient in an effective amount. The dosage range at which these compounds exhibit this hypotensive effect can vary widely depending upon the severity of the patient's hypertension, the particular compound being administered, the route of administration, the co-administration of other therapeutic agents, and the presence of other underlying disease states. Typically, the compounds will be administered at a dosage range of from about 0.5 mg/kg/day to about 100 mg/kg/day. Repetitive daily administration may be desirable and will vary with the conditions described above. However, the compounds are typically administered from 1 to 4 times daily.

Serotonin $5HT_{1A}$ agonists, such as 8-OH DPAT, have also been shown to be effective as analgesics. Eide, Neuropharm. 31, 541 (1992). In addition to the literature precedence for this action, the compounds of Formula I demonstrate an analgesic effect is in-vivo models known in the art. One such model is the acetic acid writhing test. In this test, a group containing from 5–10 mice are administered the test compound subcutaneously. Thirty minutes after administration of the test compound, the mice are administered acetic acid intraperitoneally (0.25 % v/v, 0.4 ml). The mice are then observed for squirming and writhing. Analgesics block this squirming and writhing. The following results were obtained:

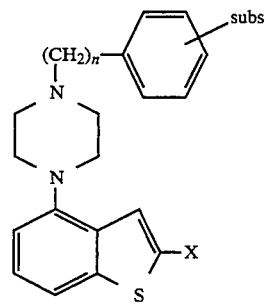

| n | Compound Subs. | X | $ED_{50}$ (mg/kg) |
|---|---|---|---|
| 2 | H | $CH_2OH$ | 0.61 |
| 2 | H | $CONH_2$ | 0.12 |
| 3 | H | $CH_2OH$ | 1.74 |
| 2 | 4-Cl | $CONH_2$ | 0.05 |
| 2 | $4\text{-}CH_3$ | $CONH_2$ | 0.03 |

The compounds will exhibit this analgesic effect at the same doses as described above for anxiety.

It has also been observed that the compounds of this invention are useful in the treatment of angina. Increased concentration of 5-HT have been found in coronary sinus of patients with complex coronary artery lesions. In unstable angina, transient reduction of coronary blood flow causes repetitive episodes of ischemia. This reduction of blood flow is caused by periodic platelet aggregation, thrombus formation or both at sites of eccentrically shaped coronary arterial stenosis and endothelial dysfunction. Platelet aggregation releases 5-HT which further accelerates aggregation and vasoconstriction. It has been reported that both $5\text{-}HT_1$ ($5\text{-}HT_{1D}$) and $5\text{-}HT_2$ receptors mediate vasoconstriction in human coronary artery. 5-HT also stimulates an endothelium-dependent vasodilation in normal coronary artery via $5\text{-}HT_{1D}$ receptor. However in endothelium damaged coronary artery, 5-HT has an unopposed vasoconstricting effect. Therefore, compounds which possess $5\text{-}HT_{1D}$ (see Saxena P. R. and Villalon, C. M.: 5-Hydroxytryptamine: a chameleon in the heart, *Trends in Pharmacological Sciences* 12:223–227, 1991) and $5\text{-}HT_2$ receptor antagonist activity may be beneficial for the treatment of angina. Since specific $5\text{-}HT_2$ receptor antagonists are available already, this research focuses on $5\text{-}HT_{1D}$ receptor antagonists only.

We have used canine saphenous vein for studying $5\text{-}HT_{1D}$ receptors which is similar, although not totally identical, to human coronary $5\text{-}HT_{1D}$ receptors (see Humphrey, P. P. A., Feniuk, W., Perren, M. J., Connor, H. E., Oxford, A. W., Coates, I. H. and Butina, D.: GR43175, a selective agonist for the $5\text{-}HT_1$-like receptor in dog isolated saphenous vein, *Br. J. Pharmacol.* 94:1123–1132, 1988; Kaumann, A. J.: Human heart 5-HT receptors, *Second international symposium on serotonin, from cell biology to pharmacology and therapeutics*, Houston, Sep. 15–18, 1992).

Methods

Mongrel dogs weighing 12–18 kg were killed by an intravenous injection of an overdose of sodium pentobarbitol. Saphenous veins were isolated, removed, cleaned of surrounding connective tissue, and cut into helical strips in a dish containing Krebs-Henseleit solution with the following composition in mM: NaCl, 110.0; KCl, 4.8; CaCl$_2$, 2.5; KH$_2$PO$_4$, 1.2; EDTA(Na-EDTA), 0.027; and was constantly bubbled with 95% O$_2$-5% CO$_2$. Unless otherwise specified, the endothelium of the carotid arteries was removed by rubbing with a metal rod. The intactness or absence of functional endothelium was checked by the presence or absence of a relaxant effect of acetycholine (10$^{-5}$M) in phenylephrine-contracted tissues (see Furchgott, R. F. and Zawadzki, J. V.: The obligatory role of endothelial cells in the relaxtion of arterial smooth muscle by acetycholine, *Nature* 288:373–376, 1980). Each muscle strip (3×30 mm) was set up in a tissue bath at 37° C. and loaded with 2 gram tension. Contractility of the tissues was measured isometrically with a Grass FT03 force-displacement transducer and recorded on a Strip chart recorder. The tissues were allowed to stabilize for 2 hours before the experiment was started, during which time they were washed repeatedly. Tissues were contracted with 3.162×10$^{-6}$M phenylephrine and 40 mM KCl, which produced 60–70% of their maximum contractile responses, to condition the tissue. 5-HT dose response experiment was conducted. Test compounds were then incubated with the tissue before a second 5-HT dose response experiment was performed. Data are expressed as the pA$_2$ value, the negative logarithm of the molar concentration of antagonist which produced a 2 fold shift in ED$_{50}$ values of 5-HT dose response curves (see Van Rossum, J. M.: Cumulative dose-response curve: Technique for the making of dose-response curves in isolated organs and the evaluation of drug parameters, *Arch. Int. Pharmacodyn. Ther.* 143:299–330, 1963).

The compounds of the present invention may be administered by a variety of routes. They are effective if administered orally. The compounds may also be administered parenterally (i.e. subcutaneously, intravenously, intramuscularly, or intraperitoneally).

As used in this application:

a) the term "patient" refers to warm blooded animals such as, for example, guinea pigs, mice, rats, cats, rabbits, dogs, monkeys, chimpanzees, and humans;

b) the term "treat" refers to the ability of the compounds to either relieve, alleviate, or slow the progression of the patient's disease.

c) the term "anxiety" refers to the unpleasant emotional state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension.

d) the term "depression" should be construed as encompassing those conditions which the medical profession have referred to as major depression, endogenous depression, psychotic depression, involutional depression, involutional melancholia, etc. These conditions are used to describe a condition in which patients typically experience intense sadness and despair, mental slowing, loss of concentration, pessimistic worry, despair, and agitation. The patients often experience physical complaints such as insomnia, anorexia, decreased energy, decreased libido, etc.

Serotonin 5HT$_{1A}$ agonists have also been shown to be useful in the treatment of stroke. It has been discovered that these compounds exhibit a neuroprotective effect and will either relieve or inhibit the CNS damage that typically accompanies a stroke. This neuroprotective effect is believed to be due to serotonin's inhibitory effect upon excitatory neurotransmission. For example, Bielenberg et al showed that the 5HT$_{1A}$ agonists 8-OH-DPAT, buspirone, gepirone, ipsapirone, and Bay R 1531 inhibited or decreased neuronal destruction in rodent models of stroke. *Stroke Supplement IV*, Volume 21, No. 12 (December, 1990). Since the compounds of Formula I are serotonin 5HT$_{1A}$ agonists, they will be useful in the treatment of stroke.

In order to exhibit this neuroprotective effect, it is necessary that the compounds be administered to the patient in an effective amount. The dosage range at which these compounds exhibit this effect can vary widely depending upon the severity of the patient's condition, the particular compound being administered, the route of administration, the co-administration of other therapeutic agents, and the presence of other underlying disease states. Typically, the compounds will be administered at a dosage range of from 0.01 mg/kg/day to about 100 mg/kg/day. Repetitive daily administration may be desirable and will vary with the conditions described above. However, the compounds are typically administered from 1 to 4 times daily or as a continuous intravenous infusion.

Stroke is a condition in which injury to the brain results due to either ischemic or hemorrhagic lesions. It is also commonly referred to as a cerebrovascular accident. The compounds of Formula I can be used to treat any of these conditions. As used herein, the phrase "treating stroke" refers to the ability of the compounds to either inhibit or decrease the CNS damage that typically accompanies a stroke.

As is readily apparent to those skilled in the art, the compounds of Formula I will not correct any CNS damage that has already occurred as the result of the cerebrovascular accident. The compounds should be administered at the initiation of the cerebrovascular accident, or soon thereafter, prior to the occurrence of extensive CNS damage.

The compounds of Formula I are also serotonin 5HT$_{1D}$ receptor agents. The affinity of the compounds for the 5HT$_{1D}$ site can be demonstrated in binding procedures such as those described by Peroutka et al in *European Journal of Pharmacology*, Vol. 163 at pages 133–166 (1989).

It has been reported that 5HT$_{1D}$ agonists are effective in the treatment of migraine. The 5HT$_{1D}$ agonist, sumatriptan, was shown to produce antimigraine-like effects in animal models and to terminate acute migraine attacks in early clinical trials. Peroutka et al, id.; Saxena et al, TIPS- Vol. 10, page 200, May 1989; and Hamel et al, Br. J. Pharmacol. (1991) 102,227–223. Since the compounds of Formula I are serotonin 5HT$_{1D}$ agonists, they may be utilized to terminate migraine attacks.

Migraine attacks are associated with excessive dilation of the extracerebral cranial vasculature. Since serotonin 5HT$_{1D}$ agonists constrict these vessels, it is currently believed that this is the mechanism by which they terminate migraine attacks. Saxena et al, id. The ability of the compounds of Formula I to produce constriction of these extracerebral cranial vessels can be demonstrated using the method of Boer et al, Br. J. Pharmacol. (1991), 102, 323–330.

In addition to terminating acute migraine attacks, the compounds can be administered on a prophylactic basis to prevent the occurrence of migraines. In order to produce these anti-migraine effects, it is necessary that the compounds be administered to the patient in an effective amount. The dosage range at which these compounds exhibit these anti-migraine effects can vary widely depending upon the severity of the patient's migraine, the particular compound being administered, the route of administration, the co-administration of other therapeutic agents, and the presence of other underlying disease states. Typically, the compounds will be administered at a dosage range of from about 0.5 mg/kg/day to about 100 mg/kg/day. Repetitive daily administration may be desirable and will vary with the conditions described above. However, the compounds are typically administered from 1 to 4 times daily.

Pharmaceutical compositions can be manufactured utilizing techniques known in the art. Typically an antidepressant, anxiolytic, anti-hypertenisve, anti-stroke, or anti-migraine amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention.

The compounds of Formula I may also be admixed with any inert carrier and utilized in laboratory assays in order to determine the concentration of the compounds within the serum, urine, etc., of the patient as is known in the art.

What is claimed is:

1. A method for producing an agonist effect at the $5HT_{1A}$ or $5HT_{1D}$ receptor comprising administering a compound of the formula:

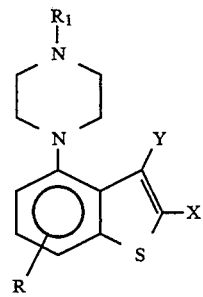

Formula I in which Y is represented by hydrogen or $C_{1-3}$ alkyl; R is represented by a substituent selected from the group consisting of hydrogen, $C_{1-4}$ alkyl, $C_{1-4}$ alkoxy, halogen, —$CF_3$, —$OCF_3$, and —OH; $R_1$ is represented by hydrogen, cycloalkyl, $C_{1-6}$ alkyl, phenyl optionally substituted, phenylalkyl, or phenylamidoalkyl; X is represented by hydrogen, —$(CH_2)_nX_1$, CH=$CHX_1$ or $CHX_2$-$(CH_2)_q$—$CH_3$; n is an integer from 0–2; q is either the integer 0 or 1; $X_1$ is represented by —OH—, —$OR_2$, —$NR_2R_3$, —$CO_2R_2$, —$CONR_2R_3$, —CN, or —$COR_2$; $R_2$ and $R_3$ are each independently represented by hydrogen, $C_{1-4}$ alkyl, phenyl optionally substituted, phenylalkyl, or $R_2$ and $R_3$ together form a $(CH_2)_m$ cycloalkyl, where m=2–6; $X_2$ is —$OR_4$ or —$NR_4R_5$ in which $R_4$ and $R_5$ are each independently hydrogen or $C_{1-4}$ alkyl; and the pharmaceutically acceptable addition salts thereof; with the proviso that when n is 0 or X is —CH=CHX$_1$, then X$_1$ is not OH, OR$_2$, or NR$_2$R$_3$; to a patient in need thereof.

2. A method for the treatment of angina comprising administering a compound of the formula:

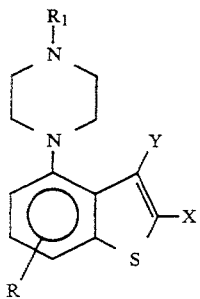

Formula I in which Y is represented by hydrogen or $C_{1-3}$ alkyl; R is represented by a substituent selected from the group consisting of hydrogen, $C_{1-4}$ alkyl, $C_{1-4}$ alkoxy, halogen, —CF$_3$, —OCF$_3$, and —OH; R$_1$ is represented by hydrogen, cycloalkyl, $C_{1-6}$ alkyl, phenyl optionally substituted, phenylalkyl, or phenylamidoalkyl; X is represented by hydrogen, —(CH$_2$)$_n$X$_1$, CH=CHX$_1$ or CHX$_2$-(CH$_2$)$_q$-CH$_3$; n is an integer from 0-2; q is either the integer 0 or 1; X$_1$ is represented by —OH—, —OR$_2$, —NR$_2$R$_3$, —CO$_2$R$_2$, —CONR$_2$R$_3$, —CN, or —COR$_2$; R$_2$ and R$_3$ are each independently represented by hydrogen, $C_{1-4}$ alkyl, phenyl optionally substituted, phenylalkyl, or R$_2$ and R$_3$ together form a (CH$_2$)$_m$ cycloalkyl, where m=2-6; X$_2$ is —OR$_4$ or —NR$_4$R$_5$ in which R$_4$ and R$_5$ are each independently hydrogen or $C_{1-4}$ alkyl; and the pharmaceutically acceptable addition salts thereof; with the proviso that when n is 0 or X is —CH=CHX$_1$, then X$_1$ is not OH, OR$_2$, or NR$_2$R$_3$; to a patient in need thereof.

* * * * *